US00RE49037E

(19) United States
(12) Reissued Patent
Burton et al.

(10) Patent Number: US RE49,037 E
(45) Date of Reissued Patent: Apr. 19, 2022

(54) BROADLY NEUTRALIZING ANTIBODY AND USES THEREOF

(71) Applicants: International AIDS Vaccine Initiative, New York, NY (US); The Scripps Research Institute, La Jolla, CA (US); Cornell University, Ithaca, NY (US)

(72) Inventors: Dennis R. Burton, La Jolla, CA (US); Marit J. Van Gils, La Jolla, CA (US); Wayne Koff, New York, NY (US); Pascal R. G. Poignard, New York, NY (US); Rogier W. Sanders, Ithaca, NY (US); Melissa D. J. S. Simek-Lemos, New York, NY (US); Devin Sok, La Jolla, CA (US)

(73) Assignees: International AIDS Vaccine Initiative, New York, NY (US); The Scripps Research Institute, La Jolla, CA (US); Cornell University, Ithaca, NY (US)

(21) Appl. No.: 16/726,453

(22) Filed: Dec. 24, 2019

Related U.S. Patent Documents

Reissue of:
(64) Patent No.: 10,093,720
Issued: Oct. 9, 2018
Appl. No.: 14/731,621
Filed: Jun. 5, 2015

U.S. Applications:
(60) Provisional application No. 62/074,963, filed on Nov. 4, 2014, provisional application No. 62/010,852, filed on Jun. 11, 2014.

(51) Int. Cl.
*C07K 16/10* (2006.01)

(52) U.S. Cl.
CPC ..... *C07K 16/1063* (2013.01); *C07K 2317/21* (2013.01); *C07K 2317/55* (2013.01); *C07K 2317/565* (2013.01); *C07K 2317/76* (2013.01)

(58) Field of Classification Search
CPC ..... C07K 16/1063; C07K 2317/21; C07K 2317/76
See application file for complete search history.

(56) References Cited

U.S. PATENT DOCUMENTS

| | | | |
|---|---|---|---|
| 10,093,720 | B2 | 10/2018 | Burton et al. |
| 2011/0044944 | A1 | 2/2011 | Chan-Hui et al. |
| 2011/0044994 | A1 | 2/2011 | Chan-Hui et al. |
| 2011/0212016 | A1 | 9/2011 | Lee et al. |
| 2013/0251726 | A1 | 9/2013 | Mascola et al. |
| 2014/0205607 | A1 | 7/2014 | Mascola et al. |
| 2014/0205612 | A1 | 7/2014 | Chan-Hui et al. |
| 2015/0218257 | A1 | 8/2015 | Chan-Hui et al. |
| 2015/0274813 | A1 | 10/2015 | Mouquet et al. |

FOREIGN PATENT DOCUMENTS

| | | | |
|---|---|---|---|
| WO | 2010/107939 | | 9/2010 |
| WO | 2010/107939 | A2 | 9/2010 |
| WO | 2011/092593 | | 8/2011 |
| WO | 2011/092593 | A2 | 8/2011 |
| WO | 2012/030904 | | 3/2012 |
| WO | 2012/030904 | A2 | 3/2012 |
| WO | 2012/040562 | | 3/2012 |
| WO | 2012/040562 | A2 | 3/2012 |
| WO | 2012/154311 | | 11/2012 |
| WO | 2012/154311 | A2 | 11/2012 |
| WO | 2014/063059 | | 4/2014 |
| WO | 2014/063059 | A1 | 4/2014 |

OTHER PUBLICATIONS

Xiang, J., et al., 1995, Framework residues 71 and 93 of the chimeric B72.3 antibody are major determinants of the conformation of heavy-chain hypervariable loops, J. Mol. Biol. 253:385-390.
Brown, M., et al., 1996, Tolerance to Single, but not multiple, amino acid replacements in antibody VH CDr2, J. Immunol. 156:3285-3291.
European Search Report dated Dec. 17, 2015, which issued during prosecution of European Application No. EP 15001720.0.
Sok, et al. "Recombinant HIV envelope trimer selects for quaternary-dependent antibodies targeting the trimer apex" PNAS, Dec. 2014, 111(49):17624-17629.

*Primary Examiner* — Bruce R Campell
(74) *Attorney, Agent, or Firm* — Nixon & Vanderhye, PC

(57) ABSTRACT

The present invention relates to an exceptionally broad and potent neutralizing antibody which may comprise cross-clade neutralizing coverage of 83% at a median $IC_{50}$ of 0.003 μg/ml, compositions containing the same and uses thereof.

23 Claims, 12 Drawing Sheets
(11 of 12 Drawing Sheet(s) Filed in Color)

Specification includes a Sequence Listing.

FIG. 2A

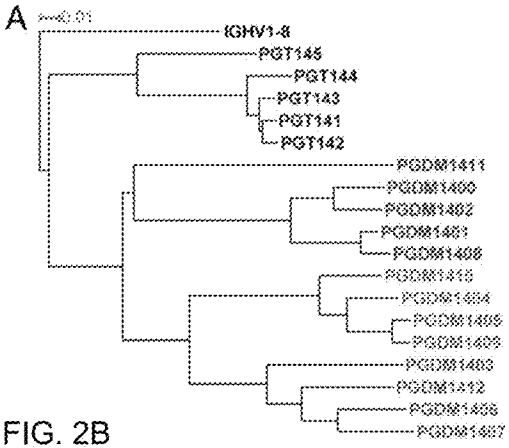

FIG. 2B

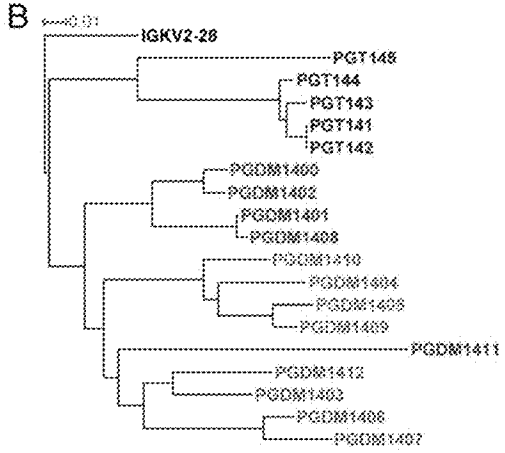

FIG. 2C

C

| Clade | n | PGDM1400 | PGDM1401 | PGDM1403 | PGDM1404 | PGDM1406 | PGDM1408 | PG9 | PGT143 | PGT145 |
|---|---|---|---|---|---|---|---|---|---|---|
| B | 11 | 73% | 64% | 0% | 9% | 0% | 0% | 45% | 45% | 64% |
| B (T/F) | 6 | 50% | 33% | 0% | 0% | 0% | 0% | 67% | 33% | 33% |
| C | 13 | 85% | 69% | 31% | 31% | 31% | 8% | 85% | 54% | 54% |
| C (T/F) | 8 | 88% | 63% | 50% | 25% | 38% | 25% | 88% | 38% | 63% |
| BC | 6 | 100% | 83% | 100% | 67% | 33% | 17% | 100% | 50% | 100% |
| A | 4 | 100% | 75% | 50% | 50% | 50% | 0% | 100% | 50% | 75% |
| A (T/F) | 1 | 100% | 100% | 100% | 100% | 100% | 100% | 100% | 100% | 100% |
| CRF02_AG | 6 | 100% | 83% | 67% | 50% | 17% | 0% | 83% | 17% | 33% |
| CRF01_AE | 10 | 100% | 70% | 40% | 80% | 10% | 0% | 80% | 70% | 100% |
| CRF01_AE (T/F) | 2 | 100% | 0% | 0% | 0% | 0% | 0% | 100% | 0% | 0% |
| G, D, CD, AC | 10 | 70% | 60% | 30% | 50% | 30% | 0% | 50% | 30% | 50% |
| **Total** | **77** | **83%** | **58%** | **36%** | **38%** | **22%** | **6%** | **81%** | **44%** | **64%** |
| % Neutralization breadth | | 100% | 80% | 60% | 40% | 20% | 0% | | | |

| Clade | n | PGDM1400 | PGDM1401 | PGDM1403 | PGDM1404 | PGDM1406 | PGDM1408 | PG9 | PGT143 | PGT145 |
|---|---|---|---|---|---|---|---|---|---|---|
| B | 11 | 0.550 | 0.017 | NA | 2.00 | NA | NA | 0.097 | 0.054 | 0.024 |
| B (T/F) | 6 | 1.05 | 0.102 | NA | NA | NA | NA | 0.723 | 0.274 | 0.051 |
| C | 13 | 0.001 | 0.005 | 0.102 | 1.00 | 0.006 | 2.00 | 0.064 | 0.242 | 0.042 |
| C (T/F) | 8 | 0.005 | 0.005 | 0.054 | 1.02 | 0.020 | 0.107 | 0.047 | 0.124 | 0.102 |
| BC | 6 | 0.001 | 0.001 | 0.022 | 1.00 | 0.002 | 0.031 | 0.049 | 0.006 | 0.097 |
| A | 4 | 0.001 | 0.001 | 0.023 | 0.003 | 0.003 | NA | 0.014 | 0.165 | 0.090 |
| A (T/F) | 1 | 0.002 | 0.006 | 0.023 | 0.006 | 0.162 | 0.819 | 0.023 | 0.023 | 0.028 |
| CRF02_AG | 6 | 0.015 | 0.015 | 0.012 | 0.044 | 0.006 | NA | 0.082 | 0.022 | 0.177 |
| CRF01_AE | 10 | 0.003 | 0.004 | 0.158 | 1.05 | 0.006 | NA | 0.079 | 0.070 | 0.055 |
| CRF01_AE (T/F) | 2 | 1.01 | NA | NA | NA | NA | NA | 1.00 | NA | NA |
| G, D, CD, AC | 10 | 0.003 | 0.003 | 0.093 | 1.06 | 0.006 | NA | 0.212 | 0.032 | 0.047 |
| **Total** | **77** | **0.003** | **0.005** | **0.041** | **0.044** | **0.006** | **0.173** | **0.074** | **0.040** | **0.042** |
| Median $IC_{50}$ (μg/mL) | | 1.00 | 0.100 | 0.010 | 0.001 | | | | | |

FIGURE 2

FIG. 3A
A
| | < 50 µg/mL | < 1.0 µg/mL | < 0.10 µg/mL | < 0.01 µg/mL |
|---|---|---|---|---|
| PGDM1400 + PGT121 | 98 | 98 | 92 | 58 |
| PGDM1400 | 93 | 76 | 66 | 51 |
| PGDM1401 | 82 | 64 | 53 | 36 |
| PGT151 | 84 | 58 | 50 | 35 |
| CAP256-VRC26.08 | 46 | 46 | 44 | 33 |
| CAP256-VRC26.09 | 47 | 47 | 42 | 23 |
| PGT121 | 86 | 52 | 44 | 22 |
| PGT145 | 75 | 55 | 33 | 15 |
| PGT128 | 59 | 49 | 44 | 14 |
| PG9 | 83 | 66 | 40 | 9 |
| PGV04 | 74 | 65 | 34 | 5 |
100-80 80-60 60-40 40-20 20-0
% Neutralization (n = 106)
FIG. 3B
B
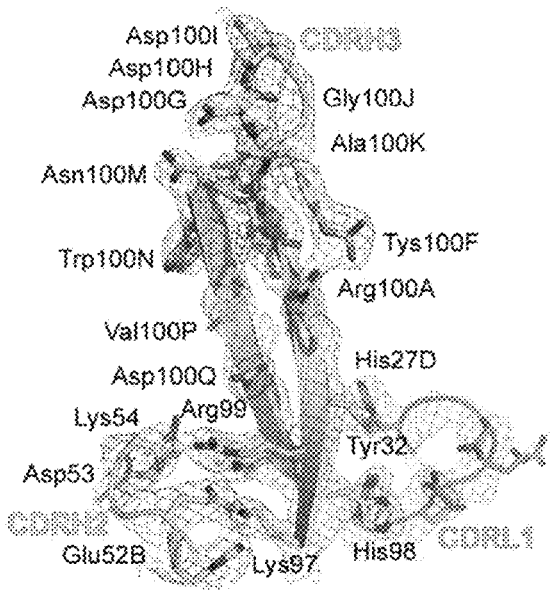
FIG. 3C
C
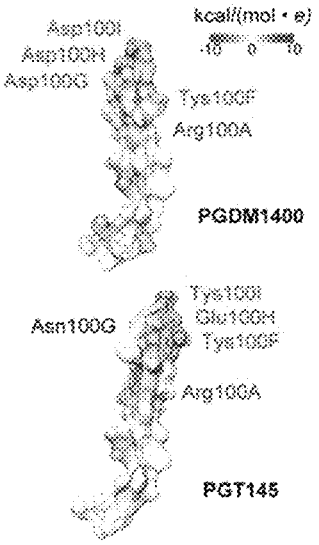
D
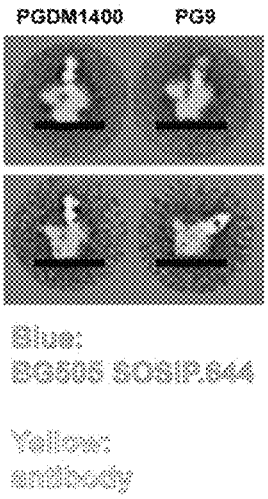
FIG. 3D
FIG. 3

FIG. 5A
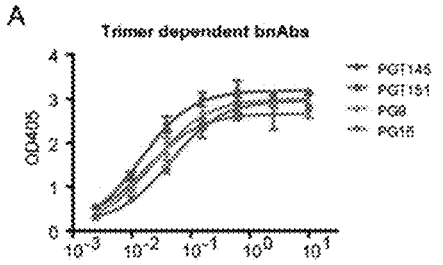
FIG. 5B
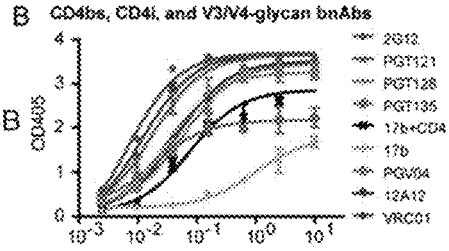
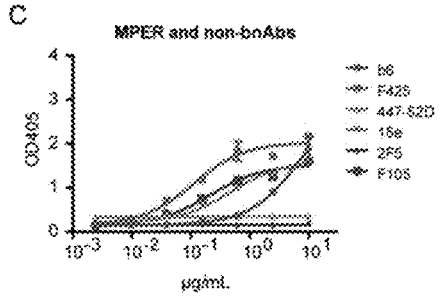
FIG. 5C
FIG. 5D
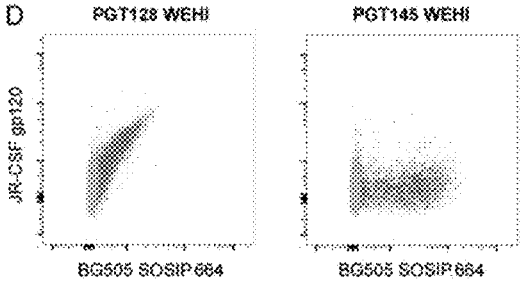
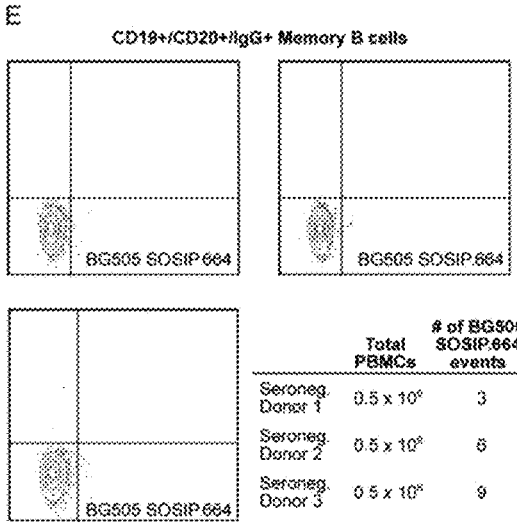
| | Total PBMCs | # of BG505 SOSIP.664 events |
|---|---|---|
| Seroneg. Donor 1 | $0.5 \times 10^6$ | 3 |
| Seroneg. Donor 2 | $0.5 \times 10^6$ | 6 |
| Seroneg. Donor 3 | $0.5 \times 10^6$ | 9 |
FIG. 5
FIG. 5E

| | mAb | V-GENE | J-GENE | CDRH3 Length (aa) | CDRH3 Sequence (aa) | $V_HJ_H$ % mut (nt) | Insertion/Deletions |
|---|---|---|---|---|---|---|---|
| HEAVY CHAIN | PGDM1400 | IGHV1-8 | IGHJ6 | 34 | CARGSRNRLRDYALYDRFGALWGAYDVDYLSNLEFW | 73% | |
| | PGDM1401 | | | 34 | CARGSRNRLRDYVKYDRYGALQWAYYVDYLSNLDYW | 73% | |
| | PGDM1402 | | | 34 | CARGSRNRLRDYALYDRYGALQWAYDVDYLSTLEFW | 73% | |
| | PGDM1403 | | | 33 | CVRGSKFRLWEWADYNEWGLVSAQWGDYYYQLGTW | 74% | |
| | PGDM1404 | | | 34 | CVRGAKFRLWWDATYDYWNDLLWADDRDYYYQYLDLW | 77% | |
| | PGDM1405 | | | 34 | CVRGAKFRLWWDATYDYYNDLLWADDRDYYYQYLDLW | 76% | |
| | PGDM1406 | | | 33 | CVRGQKFRLYEWADYNEFGLVAAQWGDYYYQLDYW | 76% | |
| | PGDM1407 | | | 33 | CVRGQKFRLYEWADYNEFGLVAAEWGDYYYQLDYW | 75% | |
| | PGDM1408 | | | 34 | CARGSRNRLRDYVNYDDYGALQWAYYVDYLANLDYW | 73% | |
| | PGDM1409 | | | 34 | CVRGAKFRLRWDATYDYWNDLLWADDRDYYYQYLDLW | 75% | |
| | PGDM1410 | | | 34 | CVRGSKFRLRWDAIYDYWNDLLWADDGDYYYKYLDLW | 75% | |
| | PGDM1411 | | | 33 | CARRTRKQLKAEYVLDQEDGFYRRKATYIYVLDYW | 76% | |
| | PGDM1412 | | | 33 | CVRGLKFRLRENSDYNEFGLVAAQWGDYYYQMEYW | 76% | |
| | PGT141 | | | 34 | CTRGSKNRLRDYVLYDDYGLINYQEWNDYLEFLDYW | 82% | |
| | PGT142 | | | 34 | CTRGSKNRLRDYVLYDDYGLINYQEWNDYLEFLDYW | 82% | |
| | PGT143 | | | 34 | CTRGSKNRLRDYVLYDDYGLINYQEWNDYLEFLDYW | 82% | |
| | PGT144 | | | 34 | CTRGSKNRLRDYVLYDDYGLINQQEWNDYLEFLDYW | 82% | |
| | PGT145 | | | 33 | CLTGSKNRLRDYFLYNETGFNYFEWGDYLATLDYW | 77% | |
| LIGHT CHAIN | PGDM1400 | IGKV2-28 | IGKJ1 | 9 | CMQGRESPWTF | 89% | |
| | PGDM1401 | | | 9 | CMQGRESPWTF | 89% | |
| | PGDM1402 | | | 9 | CMQGRESPWTF | 89% | |
| | PGDM1403 | | | 9 | CMQGLQSPYTF | 88% | +7 (CDR1) |
| | PGDM1404 | | | 9 | CMQGRRTPLTF | 85% | +3 (CDR1) |
| | PGDM1405 | | | 9 | CMQGRRTPLTF | 84% | +3 (CDR1) |
| | PGDM1406 | | | 9 | CMQGLRTPWTF | 84% | +7 (CDR1) |
| | PGDM1407 | | | 9 | CMQGLRTPWTF | 82% | +7 (CDR1) |
| | PGDM1408 | | | 9 | CMQGHESPWTF | 88% | |
| | PGDM1409 | | | 9 | CMQGHRTPLTF | 85% | +3 (CDR1) |
| | PGDM1410 | | | 9 | CMQGHRTPLTF | 86% | +3 (CDR1) |
| | PGDM1411 | | | 9 | CMQTLRPPSAF | 78% | -1 (CDR1) |
| | PGDM1412 | | | 9 | CMQGLQVPWTF | 88% | +7 (CDR1) |
| | PGT141 | | | 9 | CMQGLNRPWTF | 86% | |
| | PGT142 | | | 9 | CMQGLNRPWTF | 88% | |
| | PGT143 | | | 9 | CMQGLNRPWTF | 86% | |
| | PGT144 | | | 9 | CMQGLNRPWTF | 87% | |
| | PGT145 | | | 9 | CMQGLNSPWTF | 84% | |

FIG. 6

FIG. 7A
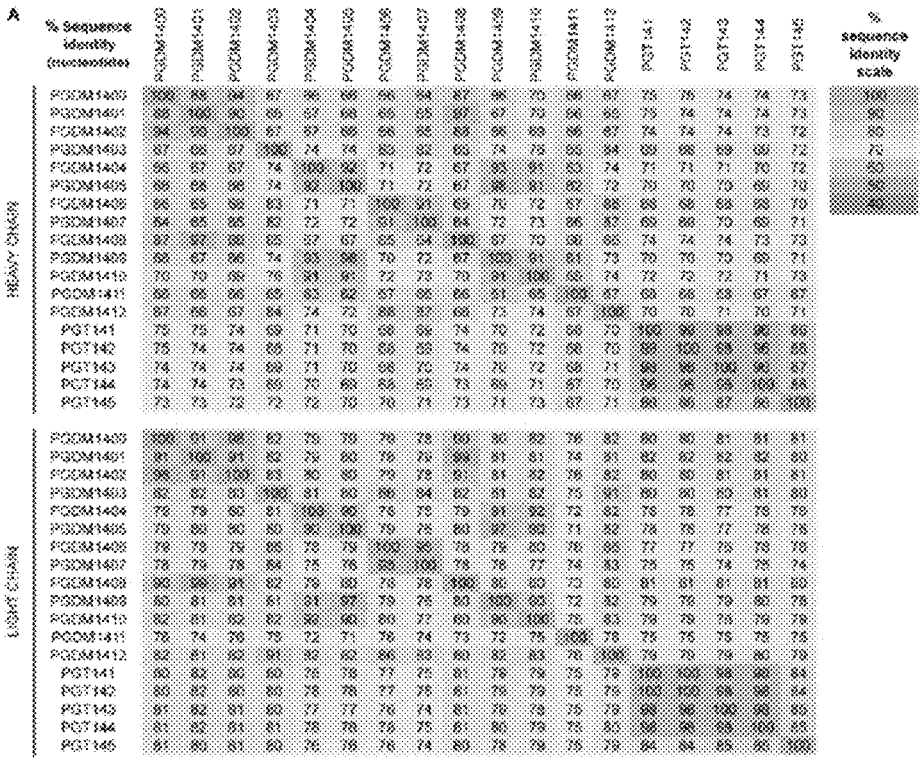
FIG. 7B
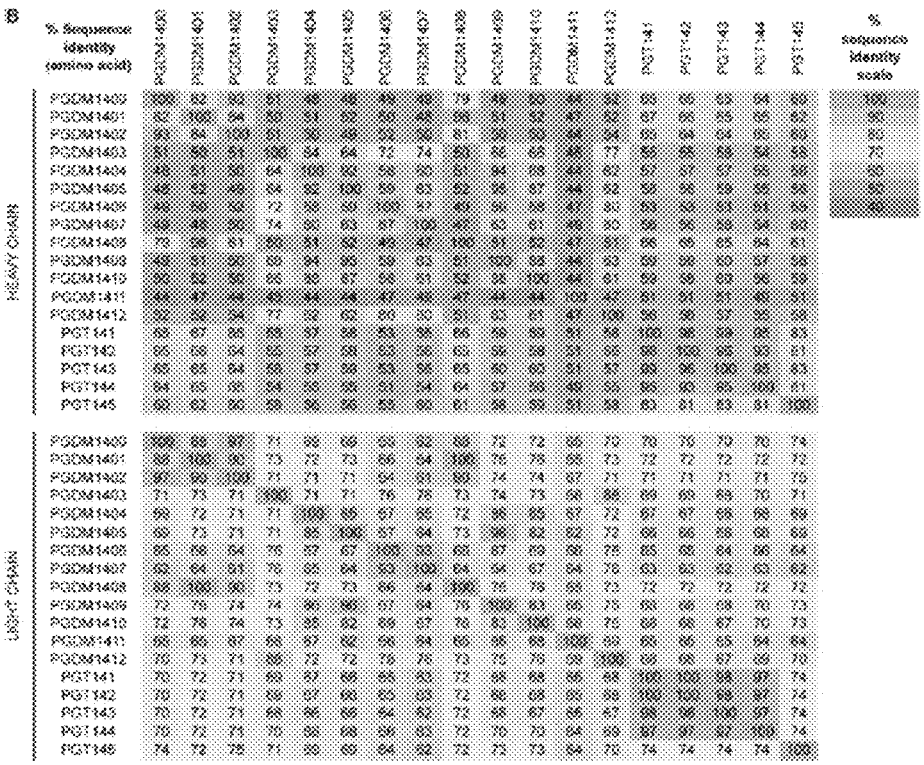
FIG. 7

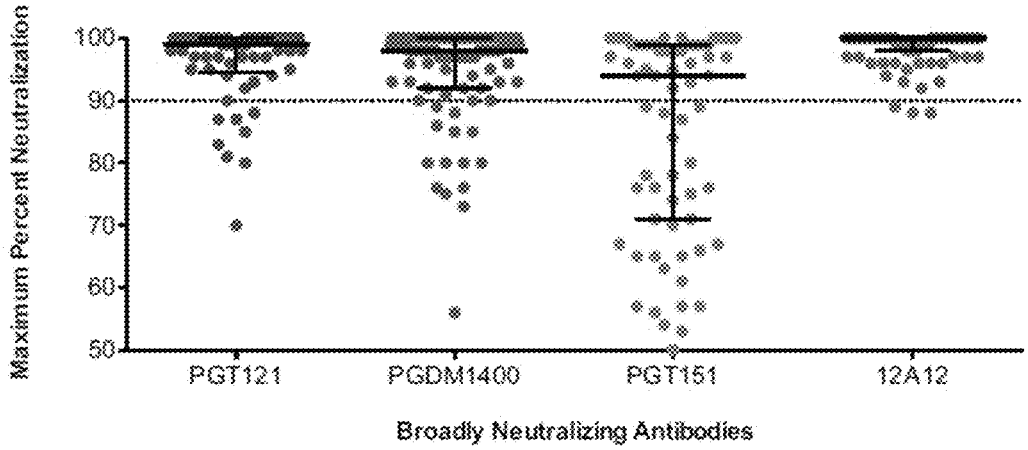
FIG. 10
FIG. 11A
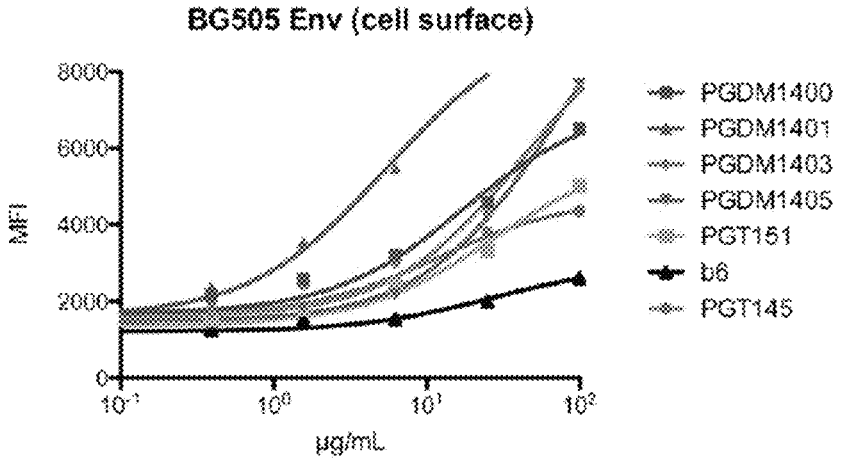
FIG. 11B
B
| $IC_{50}$ (μg/mL) | PGDM1400 | PGDM1401 | PGDM1403 | PGDM1404 | PGDM1405 | PGDM1406 | PGDM1407 | PGT145 |
|---|---|---|---|---|---|---|---|---|
| BG505 | [illegible] | [illegible] | > 10 | > 50 | > 50 | > 50 | > 50 | 0.027 |
FIG. 11

BROADLY NEUTRALIZING ANTIBODY AND USES THEREOF

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

RELATED APPLICATIONS AND INCORPORATION BY REFERENCE

This application *is a broadening reissue of U.S. Pat. No. 10,093,720, issued Oct. 9, 2018 from U.S. patent application Ser. No. 14/731,621 filed Jun. 5, 2016, which claims* benefit of and priority to U.S. provisional patent application Ser. No. 62/010,852 filed Jun. 11, 2014 and 62/074,963 filed Nov. 4, 2014.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FEDERAL FUNDING LEGEND

This invention was made with government support under NIH R01 AI033292, NIH R01 AI84817, NIH R37 AI36082 and NIH Interdisciplinary Training Program in Immunology 5T32AI007606-10 awarded by the NIH. This invention was made with government support under USAID Cooperative Agreement No. AID-OAA-A-11-00020 awarded by the USAID. The government has certain rights in the invention.

FIELD OF THE INVENTION

The present invention relates to an exceptionally broad and potent neutralizing antibody with cross-clade neutralizing coverage of, for example, 83% at a median $IC_{50}$ of 0.003 μg/ml, and uses thereof.

SEQUENCE LISTING

The instant application contains a Sequence Listing which has been submitted electronically in ASCII format and is hereby incorporated by reference in its entirety. Said ASCII copy, created on [Jun. 22, 2015] *Dec. 23, 2019*, is named [43094.02.2029_SL.txt] *6765.0700_Sequence_Listing.txt* and is [34,017] *34,127* bytes in size.

BACKGROUND OF THE INVENTION

Efforts towards an effective HIV vaccine have been greatly hampered by the high antigenic variability of the HIV envelope spike (Env). Despite this variability, an increasing number of monoclonal antibodies (mAbs) that are capable of recognizing a diversity of cross-clade isolates, termed broadly neutralizing antibodies (bnAbs), have been isolated from chronically infected donors (Walker, L. M. et al. Science 326, 285-289 (2009); Doria-Rose, N. A. et al. Nature (2014) doi:10.1038/nature13036; Kwong, P. D. & Mascola, J. R. Immunity 37, 412-425 (2012); Walker, L. M. et al. Nature 477, 466-470 (2011); Bonsignori, M. et al. J Virol 85, 9998-10009 (2011); Burton, D. R. et al. Cell Host Microbe 12, 396-407 (2012); Wu, X. et al. Science 329, 856-861 (2010); Huang, J. et al. Nature 491, 406-412 (2012); Scheid, J. F. et al. Science 333, 1633-1637 (2011); Mouquet, H. et al. Proc Natl Acad Sci USA 109, E3268-77 (2012); Klein, F. et al. J Exp Med 209, 1469-1479 (2012); Falkowska, E. et al. Immunity (2014) doi:10.1016/j.immuni.2014.04.009; Blattner, C. et al. Immunity (2014) doi: 10.1016/j.immuni.2014.04.008). However, even for a family of bnAbs targeting the same epitope region, substantial differences in potency and breadth are found, which likely reflect fine details in epitope recognition. The isolation of families of bnAbs with different neutralization profiles against each site then serves as powerful tools to decipher the epitope features that are most important for neutralization breadth and potency.

Multiple methods have been developed to isolate bnAbs. Hybridoma and phage display techniques were used to isolate the first generation of bnAbs including 2F5, b12, 2G12, 4E10 and Z13 (Burton, D. R. et al. Science 266, 1024-1027 (1994); Muster, T. et al. J Virol 68, 4031-4034 (1994); Burton, D. R. et al. Proc Natl Acad Sci USA 88, 10134-10137 (1991); Zwick, M. B. et al. J Virol 75, 10892-10905 (2001); Barbas, C. F. et al. Proc Natl Acad Sci USA 89, 9339-9343 (1992); Trkola, A. et al. J Virol 70, 1100-1108 (1996); Conley, A. J. et al. Proc Natl Acad Sci USA 91, 3348-3352 (1994); Buchacher, A. et al. AIDS Res Hum Retroviruses 10, 359-369 (1994)). These antibodies exhibit a range of neutralization breadth against primary isolates from 30-90%, but have moderate neutralization potency (median $IC_{50}$ of ~2-4 μg/mL), suggesting that the elicitation of relatively high serum titers would be required to afford sterilizing immunity in vivo, given the observed relationship between neutralization in vitro and protection in vivo (Parren, P. W. et al. J Virol 75, 8340-8347 (2001); Hessell, A. J. et al. PLoS Pathog 5, e1000433 (2009); Mascola, J. R. et al. J Virol 73, 4009-4018 (1999)). Access to infected donors who have high serum titers of bnAbs (Simek, M. D. et al. J Virol 83, 7337-7348 (2009); Gray, E. S. et al. J Virol 85, 4828-4840 (2011)) and the availability of newer approaches for isolating human mAbs have recently enabled the discovery of a new generation of more potent bnAbs (Walker, L. M. et al. Science 326, 285-289 (2009); Doria-Rose, N. A. et al. Nature (2014) doi:10.1038/nature13036; Walker, L. M. et al. Nature 477, 466-470 (2011); Bonsignori, M. et al. J Virol 85, 9998-10009 (2011); Wu, X. et al. Science 329, 856-861 (2010); Huang, J. et al. Nature 491, 406-412 (2012); Scheid, J. F. et al. Science 333, 1633-1637 (2011)).

The first of these newer approaches involves the sorting and activation of large numbers of memory B cells using cytokine-secreting feeder cells and the subsequent high throughput screening of supernatants for neutralization. This method led to the identification and characterization of the first of this new generation of bnAbs, PG9 and PG16 (Walker, L. M. et al. Science 326, 285-289 (2009)), and has since revealed several new sites of vulnerability to bnAb recognition on Env (Walker, L. M. et al. Science 326, 285-289 (2009); Doria-Rose, N. A. et al. Nature (2014) doi:10.1038/nature13036; Walker, L. M. et al. Nature 477, 466-470 (2011); Bonsignori, M. et al. J Virol 85, 9998-10009 (2011); Wu, X. et al. Science 329, 856-861 (2010); Huang, J. et al. Nature 491, 406-412 (2012)). One of these sites, targeted by the bnAbs PG9/PG16, PGT141-145, CH01-04, and CAP256-VRC26.01-12, is situated at the trimer apex and is centered around the glycan at position 160 on Env (Walker, L. M. et al. Science 326, 285-289 (2009); Doria-Rose, N. A. et al. Nature (2014) doi:10.1038/nature13036; Walker, L. M. et al. Nature 477, 466-470 (2011); Bonsignori, M. et al. J Virol 85, 9998-10009 (2011); Julien, J.-P. et al. Proc Natl Acad Sci USA 110, 4351-4356 (2013)). Indeed, recent structural analyses have revealed that these bnAbs bind to a conserved β-sheet structure located at the trimer apex, mainly in the V2 region, but also spanning V1 and V3 (Julien, J.-P. et al. Proc Natl Acad Sci USA 110, 4351-4356 (2013); Julien, J.-P. et al. Science (2013) doi: 10.1126/science.1245625; McLellan, J. S. et al. Nature 480, 336-343 (2011); Pancera, M. et al. Nat Struct Mol Biol 20, 804-813 (2013)). In light of these new structural findings, Applicants henceforth refer to the V2-glycan bnAbs as trimer-apex glycan-dependent bnAbs. Using this screening method, bnAbs targeting other sites of vulnerability on Env were found, including the PGT121-137 antibodies, which target the high-mannose patch epitope centered around the glycan at position N332 (Walker, L. M. et al. Nature 477, 466-470 (2011); Mouquet, H. et al. Proc Natl Acad Sci USA 109, E3268-77 (2012); Julien, J.-P. et al. Science (2013) doi:10.1126/science.1245625; Pejchal, R. et al. Science 334, 1097-1103 (2011); Kong, L. et al. Nat Struct Mol Biol (2013) doi:10.1038/nsmb.2594; Sok, D. et al. PLoS Pathog 9, e1003754 (2013)), the antibody 10E8, which targets the MPER site (Huang, J. et al. Nature 491, 406-412 (2012)), and finally the PGT151-158 antibodies, which target a region at the interface of gp41 and gp120 (Falkowska, E. et al. Immunity (2014) doi:10.1016/j.immuni.2014.04.009; Blattner, C. et al. Immunity (2014) doi:10.1016/j.immuni.2014.04.008).

An alternative method for bnAb isolation involves the use of soluble Env molecules or scaffold proteins as baits to select single IgG+ memory B cells of interest by cell sorting (Wardemann, H. et al. Science 301, 1374-1377 (2003); Scheid, J. F. et al. Nature 458, 636-640 (2009)). This method has cost advantages and does not demand the automated procedures associated with direct neutralization screening. Indeed, this antigen selection method successfully isolated a number of bnAbs from various donors against the CD4bs and the supersite surrounding the N332 glycan (Wu, X. et al. Science 329, 856-861 (2010); Scheid, J. F. et al. Science 333, 1633-1637 (2011); Mouquet, H. et al. Proc Natl Acad Sci USA 109, E3268-77 (2012)). Soluble baits have not, however, been successful at isolating antibody responses targeting quaternary epitopes, including the site surrounding the N160 glycan, as the protein constructs used to date have not properly mimicked native Env trimers. To address this problem, GFP-labeled 293T cells that express cell surface Env for sorting, called GFP-293T$^{BaL}$, have been used recently to isolate antibodies 3BC176 and 3BC315 (Klein, F. et al. J Exp Med 209, 1469-1479 (2012); Gaebler, C. et al. J Immunol Methods 397, 47-54 (2013)). These antibodies do not bind soluble monomeric gp120 but do bind Env trimer, demonstrating utility of the approach, but the method was described to be inefficient compared to the use of soluble protein baits (Klein, F. et al. J Exp Med 209, 1469-1479 (2012); Gaebler, C. et al. J Immunol Methods 397, 47-54 (2013)).

The recently developed soluble BG505 SOSIP.664 gp140 trimer is a largely faithful antigenic mimic of native Env, as indicated by the strong binding of multiple bnAbs, including to quaternary-structure epitopes, and the very weak or absent binding of non-neutralizing antibodies (Sanders, R. W. et al. PLoS Pathog 9, e1003618 (2013)). The favorable antigenic profile of these trimers opens the possibility of their use for isolating quaternary-specific antibodies by single-cell sorting.

Citation or identification of any document in this application is not an admission that such document is available as prior art to the present invention.

SUMMARY OF THE INVENTION

Applicants have used BG505 SOSIP.664 to select for memory B cells from a donor from whom Applicants previously isolated the trimer-specific bnAbs PGT141-145 (Walker, L. M. et al. Nature 477, 466-470 (2011); Simek, M. D. et al. J Virol 83, 7337-7348 (2009)). This approach resulted in the isolation of novel somatic variants that are highly divergent from the PGT145 antibody family and display a range of neutralization breadth and potency, with some being more broad and potent than the previously described PGT145 family members. Overall, the results describe a mosaic of antibody responses against the trimer-apex site of vulnerability that have important implications for immunogen design in general, as well as for the future optimization of BG505 SOSIP.664 and related native-like trimers as vaccine candidates.

The present invention relates to an isolated fully human anti-HIV-1 monoclonal antibody, designated PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412. In an advantageous embodiment, the antibody is PGDM 1400.

The present invention relates to compositions which may comprise the above antibodies, including pharmaceutical compositions which may comprise pharmaceutical acceptable carriers.

The present invention also relates to a method of inhibiting HIV in a host which may comprise administering PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412 to the host, combinations thereof, or a composition which may comprise the same.

The present invention also relates to an expression vector that encodes and stably expresses in vivo an antibody which may comprise each of a heavy chain sequence of PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412 and a light chain sequence of PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412.

The present invention relates to compositions which may comprise the above expression vectors, including pharmaceutical compositions which may comprise pharmaceutical acceptable carriers. The expression vector may comprise a viral based vector or the vector may be viral based. In an advantageous embodiment, the virus may be an adeno-associated virus (AAV).

The present invention also relates to a method of inhibiting HIV in a host which may comprise administering an expression vector expressing PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412 to the host, combinations thereof, or a composition which may comprise the same.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following detailed description, given by way of example, but not intended to limit the invention solely to the specific embodiments described, may best be understood in conjunction with the accompanying drawings.

FIG. 1A—PBMCs from the PGT141-145 donor were sorted using BG505 SOSIP.664-AviB and JR-CSF gp120-AviB. Events that are BG505 SOSIP.664-AviB positive are labeled red and events that are JR-CSF gp120-AviB positive are labeled blue. FIG. 1B—A total of 62 productive heavy chain sequences were obtained, with a large enrichment of the PGT145 antibody gene family $V_H$1-8. A total of 158 productive light chain sequences were obtained, with a large enrichment for the PGT145 antibody gene family $V_K$2-28. FIG. 1C—The heavy chain sequences that were obtained are heavily mutated, with the majority having a mutation frequency of 20-30% from the inferred germline. FIG. 1D—The light chains are also mutated, with the majority having a mutation frequency of 10-20% from the inferred germline.

FIGS. 2A-C. Newly selected PGDM somatic variants display a range of neutralization breadth and potencies. FIG. 2A—Heavy chain phylogenetic tree of newly isolated somatic variants rooted at the $V_H$1-8 germline gene. New broadly neutralizing somatic variants cluster separately from the PGT141-145 antibodies, and form four clusters distinct from the PGT141-145 cluster. FIG. 2B—Kappa chain phylogenetic tree of isolated somatic variants rooted at the $V_K$2-28 germline gene. The new somatic variants cluster separately from the PGT141-145 antibodies and match the clusters formed by the heavy chain sequences shown in (A). Phylogenetic trees were generated using Clustal Omega (Sievers F et al. (2011) Mol Syst Biol 7:539). FIG. 2C—Percent neutralization breadth and median $IC_{50}$ values of somatic variants PGDM1400-1406 against a 77-virus panel are listed by clade and colored according to the legend. PG9 and the previously reported somatic variants PGT143 and PGT145 are listed for comparison. Somatic variants PGDM1402, PGDM1407-PGDM1412 were not included because of low antibody yield.

FIGS. 3A-D. PGDM1400 shows exceptional neutralization breadth and potency. FIG. 3A—Percent neutralization breadth values on a cross-clade 106-virus panel at different $IC_{50}$ cut-offs are listed for somatic variants PGDM1400 and PGDM1401 in comparison to previously reported bnAbs. Neutralization breadth and potency of a combination of PGDM1400+PGT121 was experimentally evaluated to show coverage obtained by targeting two different sites of vulnerability on Env. Listed percent breadth values are colored according to the listed legend. FIG. 3B—Crystal structure of the PGDM1400 Fab. CDRH2, H3 (yellow) and L1 (green) are shown as a secondary structure cartoon with side chains depicted as sticks. The 2Fo-Fc electron density map is a blue mesh contoured at 1.0 σ. The figure was made using Pymol (Schrodinger, LLC (2010) The PyMOL Molecular Graphics System, Version 1.3r1). FIG. 3C—Comparison between the elongated β-hairpin CDRH3s of PGDM1400 and PGT145. Key residues, including sulfated tyrosines, are shown as sticks. The transparent surface is colored as electrostatic potential according to Coulomb's law in UCSF Chimera (Pettersen E F et al. (2004) J Comput Chem 25:1605-1612). The CDRH3 orientations result from the structures being aligned on the entire Fab. FIG. 3D—Reference-free 2D class averages of PGDM1400 Fab in complex with BG505 SOSIP.664. PG9 Fab found to BG505 SOSIP.664 was included for comparison. The region corresponding to the trimer and Fab are colored in blue and yellow, respectively.

FIG. 4A—The somatic variants PGDM1400-1407 all bind to the BG505 SOSIP.664-AviB construct by ELISA. With the exception of PGDM1401, and to a lesser extent PGDM1400 and PGDM1405, the same somatic variants do not bind BG505 SOSIP.664-AviB produced with kifunensine (SOSIP+kif), or to BG505 gp120 produced recombinantly in 293F cells (r_gp120) or to BG505 gp120 monomers from lysed virions (lv_gp120). The bnAbs PGT145, PG9, VRC01, PGT121, and F425 were included for comparison. Antibodies PGDM1408-1412 were not included because of low yield. FIG. 4B-Viruses that are potently neutralized by the somatic variants PGDM1400-1406 were tested for binding by ELISA to corresponding gp120 monomers from lysed virions. Values represent neutralization $IC_{50}$ or binding $EC_{50}$ in μg/mL and colored according to the legend. PGDM1402 was excluded because of low yield. FIG. 4C—The somatic variants PGDM1400, 1401, 1405, and 1403 were evaluated for competition with PGDM1400-1407 (PGDM1402 was excluded because of low yield) for binding to BG505 SOSIP.664 trimers in competition binding ELISAs. Listed values are percent maximum competition as measured by ELISA and colored according to the legend. Antibodies targeting the trimer apex (PGT145, PG9, PG16) and those that do not (PGT121, PGT151, 2G12, and VRC01) were included for comparison. FIG. 4D—Somatic variants PGDM1400-1407 (PGDM1402 was excluded because of low yield) were tested for neutralization against the T250-4 isolate, T250-4 N160K, and T250-4+kifunensine. PG9 and PGT128 were included for comparison. FIG. 4E—Antibodies PGT145, PGDM1400, and PGDM1403 were measured for binding to BG505 SOSIP.664-AviB by Octet. Black curves represent measured data points and red curves represent best-fit lines following analysis.

FIGS. 5A-E. BG505 SOSIP.664-AviB is an appropriate probe for bnAbs. FIG. 5A-C—Biotinylated BG505 SOSIP.664-Avi (BG505 SOSIP.664-AviB) was tested in a streptavidin-capture ELISA against trimer-dependent bnAbs (A); CD4bs, CD4i, and V3/V4-glycan bnAbs (B); and MPER and non-bnAbs (C). FIG. 5D—Binding of BG505 SOSIP.664-AviB and JR-CSF gp120-AviB to PGT128 and PGT145 WEHI mouse B-cell lines (Ota T, et al. (2012) J Immunol 189(10):4816-4824.) was detected via flow cytometry using streptavidin-PE and streptavidin-Alexa 488, respectively. Values are presented in mean fluorescence intensity (MFI). FIG. 5E—PBMCs from HIV-seronegative donors were isolated by Ficoll gradient, and IgG+ memory B cells were stained with BG505 SOSIP.664-AviB and streptavidin-PE to evaluate the extent of nonspecific trimer binding.

FIG. 6. Summary of mutation frequency and gene family of newly isolated somatic variants. PGDM1400-1412 were analyzed for germline gene, CDRH3 length, CDRH3 sequence, percent identity (in nucleotides), and possible insertions or deletions. Genetic analyses were performed using the IMGT system (Lefranc M-P, et al. (2009) Nucleic Acids Res 37(Database issue):D1006-D1012). Figure discloses SEQ ID NOS 40-75, respectively, in order of appearance.

FIGS. 7A-B. Newly isolated somatic variants are highly divergent from the PGT141-145 sequences. A sequence identity matrix was created using the somatic variants PGDM1400-1412 and PGT141-145. Values listed are FIG. 7A: nucleotide percent identity and FIG. 7B: amino acid percent identity colored according to the key. Sequence identities were calculated using Clustal Omega (Sievers F, et al. (2011) Mol Syst Biol 7:539).

FIG. 10. PGDM1400 neutralizes viruses to completion as much as PGT121. MPNs were determined for PGDM1400 on a 106-virus panel (FIG. 9). For comparison, PGT151, which was reported to exhibit incomplete neutralization activity (Falkowska E, et al. (2014) Broadly neutralizing HIV antibodies define a glycan-dependent epitope on the prefusion conformation of gp41 on cleaved envelope trimers. Immunity 40(5):657-668), and PGT121 and 12A12, which have been shown to achieve generally complete neutralization for the majority of viruses, were measured in parallel. Each data point represents a different virus on a cross-clade 106-virus panel (FIG. 9). The median MPN with interquartile range is shown for each antibody.

FIGS. 11A-B. Somatic variants bind to cell-surface BG505 Env despite not neutralizing the BG505 pseudovirus. FIG. 11A—Somatic variants were tested for binding to BG505 Env expressed on the surface of 293T cells. Antibody PGT151, which binds specifically to cleaved Env, and antibody b6, which binds to uncleaved Env, were included for comparison. FIG. 11B—Antibodies also were tested for neutralization against the BG505 pseudovirus. Values shown are neutralization IC50 in micrograms per milliliter.

DETAILED DESCRIPTION OF THE INVENTION

Figures 1, 1A, 1B, 1C, 1D:
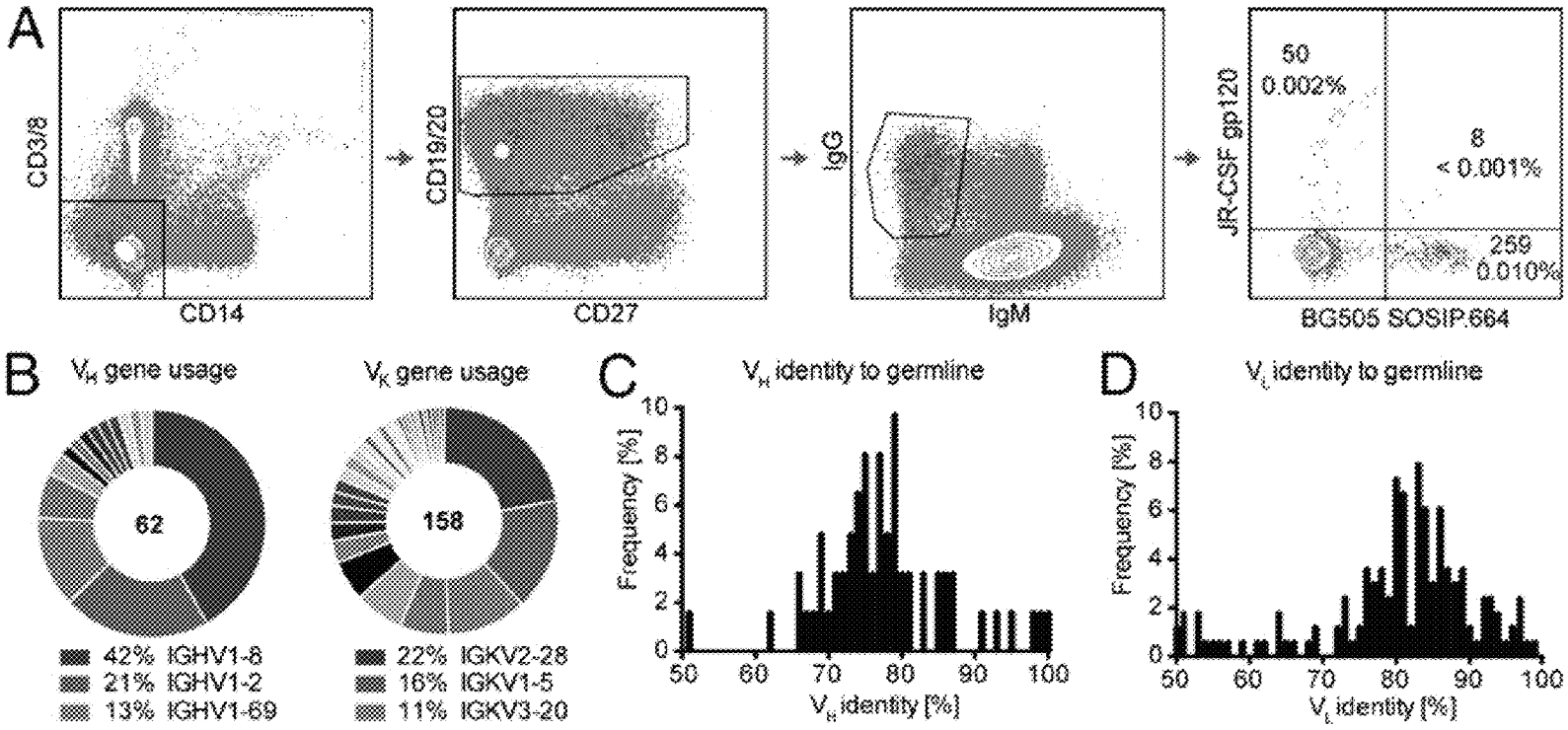
FIGS. 1A-D. BG505 SOSIP.664-AviB selects memory B cells expressing bnAbs from the PBMCs of the PGT141-145 donor.

Broadly neutralizing antibodies (bnAbs) targeting the trimer apex of HIV envelope (Env) are favored candidates for vaccine design and immunotherapy because of their high neutralization breadth and potency. Methods to isolate bnAbs against this site, however, have been limited due to the quaternary nature of the epitope region. Here Applicants report the use of a recombinant HIV envelope trimer, BG505 SOSIP.664 gp140, as an affinity reagent to isolate quaternary-dependent bnAbs from the peripheral blood of a chronically infected donor. The new bnAbs, named PGDM1400-1412, show a wide range of neutralization breadth and potency. One of these variants, PGDM1400, is exceptionally broad and potent with cross-clade neutralization coverage of 83% at a median IC50 of 0.003 μg/mL. Overall, Applicants' results highlight the utility of BG505 SOSIP.664 gp140 as a tool for the isolation of quaternary-dependent antibodies and reveal a mosaic of antibody responses against the trimer apex within a clonal family.

Broadly neutralization antibodies (bnAbs) are widely considered a critical component of an HIV vaccine. Indeed, much progress has been made in the isolation of these bnAbs and the characterization of their epitopes has revealed potential advantages and disadvantages of different sites of vulnerability on the envelope spike (Env). One of the more promising epitopes targeted by bnAbs is situated at the trimer apex of Env. Antibodies targeting this region are typically less somatically hypermutated than bnAbs targeting other sites, which favors their elicitability through vaccination. Moreover, among broadly neutralizing antibody responses in chronically infected cohorts, antibodies targeting the trimer apex emerge more frequently, emerge relatively more quickly, and generally are both broad and highly potent in neutralization compared to bnAbs targeting other sites. The major difficulty in isolating additional antibodies of this class is the quaternary nature of their epitope, which has been exceptionally difficult to mimic until recently. The development of a native-like Env trimer, the BG505 SOSIP.664 gp140, is a major breakthrough in the HIV vaccine field (Sanders, et al. Plos Pathogens, 2013). Recent structural and biochemical analyses have provided critical insight into understanding different epitopes on Env for immunogen design (Julien, et al., Lyumkis et al., Science 2013). The impressive antigenicity of this protein construct also suggests that, for the first time, the isolation of quaternary-specific bnAbs from chronically infected donors by antigen selection may be capable.

To this end, Applicants have demonstrated the utility BG505 SOSIP.644 to efficiently isolate new somatic variants of the PGT141-145 antibody family (Walker et al, Nature, 2012), which target a quaternary epitope at the trimer apex. These new variants display a range of neutralization breadth and potencies, providing insight into the diversity of antibody response that are capable through natural infection. These new antibodies subsequently provide tools for the design of immunogens that would selectively elicit the antibodies with the most favorable neutralization profiles while limiting the elicitation of related variants with more limited activity. Additionally, Applicants have isolated a new bnAb, which Applicants have called PGDM1400, that demonstrates 83% breadth with an exceptional neutralization potency of 3 ng/mL in median $IC_{50}$, which is the most potent activity among bnAbs Applicants have observed at this level of neutralization breadth. Indeed, Applicants have demonstrated the utility of PGT121, which is over 70% broad with a median $IC_{50}$ of 30 ng/mL, to potently protect against SHIV challenge in macaques (Moldt, et al. PNAS, 2013) and to dramatically reduce viral load when delivered to macaques chronically infected with SHIV (Barouch, et al. Nature, 2013). The greater neutralization breadth and 10-fold higher neutralization potency for PGDM1400 favors its use in many future therapeutic and protection studies against more resistant isolates of HIV. Indeed, PGDM1400 is capable of neutralizing up to 82% of clade C transmitted viruses, while PGT121 is only capable of neutralizing up to 57%, which favors its elicitation and use in predominately clade C endemic regions.

Applicants finally note the potential of BG505 SOSIP.644 gp140 to isolate not only quaternary-specific bnAbs targeting the timer apex, but quaternary-specific bnAbs targeting other sites. Indeed, quaternary-specific epitopes have been mapped as a predominate response among elite neutralizers of various cohorts, but 30-50% of these quaternary-specific responses are not confirmed to target the trimer apex. One of these new quaternary-specific sites, targeted by bnAbs PGT151-158, has been mapped to the gp120-gp41 interface (Falkowska, et al., Blattner, et al., Immunity, 2014). This site is both present and accessible on the BG505 SOSIP.664 gp140 construct as demonstrated by high-affinity binding of PGT151, which therefore highlights the potential utility of this construct to isolate additional members of this new class of bnAbs. If other yet to be defined quaternary-specific sites on Env are present, sorting with BG505 SOSIP.664 gp140 would still serve as a potential approach for fishing out these antibodies, as other engineered baits have not been shown to fully recapitulate quaternary epitopes. The isolation of new bnAbs to fully define broadly neutralizing epitopes and to characterize new sites of vulnerability will continue to contribute immeasurable value to HIV vaccine design efforts.

The present invention relates to broadly neutralizing epitopes PGDM1400, PGDM1401, PGDM1402, PGDM1403, PGDM1404, PGDM1405, PGDM1406, PGDM1407, PGDM1408, PGDM1409, PGDM1410, PGDM1411 and PGDM1412. The amino acid sequences of the heavy and light chains, mutation frequency and gene family are presented in FIG. 6.

The nucleotide sequences of the heavy chains of the PGDM1400, PGDM1401, PGDM1402, PGDM1403, PGDM1404, PGDM1405, PGDM1406, PGDM1407, PGDM1408, PGDM1409, PGDM1410, PGDM1411 and PGDM1412, n are:

PGDM_1400_HC (SEQ ID NO: 1)

CAGGTGCATCTGACGCAGTCTGGGCCTGAGGTGAGGAAGCCTGGGACCTC

CGTAAAGGTCTCCTGCAAGGCCCCTGGAAACACATTGAAGACTTATGATC

TACACTGGGTGCGCAGCGTCCCTGGACAAGGCCTTCAGTGGATGGGATGG

ATAAGCCATGAGGGCGACAAGAAGGTCATTGTGGAAAGATTCAAGGCCAA

AGTCACCATTGATTGGGACAGGTCCACCAATACGGCCTATCTCCAACTGA

GCGGCCTCACATCTGGCGACACGGCCGTCTATTATTGTGCGAAAGGCTCA

AAACACAGGCTGCGAGATTACGCTCTCTACGACGACGACGGCGCATTGAA

TTGGGCTGTCGATGTTGACTACCTTTCGAACTTGGAATTCTGGGGCCAAG

GGACCGCCGTCACCGTCTCTTCA

PGDM_1401_HC (SEQ ID NO: 2)

CAGGCGCAACTGGTGCAGTCTGGGCCTGAGATGAGGAAACCTGGGGCCTC

CGTAAAGGTCTCCTGCAAGGCCCCTGGAAATACATTGAAGAATCATGATC

TACACTGGGTGCGCAACGTCCCTGGACAGGGGCTTGAGTGGGTGGGGTGG

GTGAGTCACGAGGGCGACAAAAAGGTCATTGTAGAGAAATTCAAGGCCAG

CGTCACCATTGATTGGGACAGGTCCCTGAATACGGCCTATCTTCAACTGC

GCGGCCTCAGGTCTGAAGACACGGCCGTCTATTATTGTGCGAGAGGGTCA

AAACACAGGCTGCGAGACTACGTTATGTACGACGACTACGGCGCATTGCA

GTGGGCTGTCTATGTTGACTATCTTTCGAACTTGGACGTCTGGGGCCAAG

GGACCGCCGTCACCGTCTCTCCA

PGDM_1402_HC (SEQ ID NO: 3)

CAGGTGCAACTGGCGCAGTCTGGGCCTGAGGTGAGGAAGCCTGGGGCCTC

CGTAAAGGTCTCCTGCAAGGCCCCTGGAAATACATTGAAGACTTATGATC

TACACTGGGTGCGAGACGTCCCTGGACAGGGCCTGCAGTGGATGGGATGG

GTGAGCCACGAGGGCGACAAGAAGGTCATTGTGGAGAGATTCAAGGCCAA

AGTCAGCATTGATTGGGACAGGTCCACAAATACGGCCTATCTACAACTGA

GCGGCCTCACATCTGAAGACACGGCCGTCTATTATTGTGCGAAAGGCTCA

AAACACAGGCTGCGAGACTACGCTCTGTACGACGACATCGGCGCATTGCA

ATGGGCTGTCGATGTTGACTACCTTTCGACCTTGGAATTTTGGGGCCAAG

GGACCGCCGTCACCGTCTCTTCA

PGDM_1403_HC (SEQ ID NO: 4)

GAGGTGCTTCTGGAGCAGTCCGGGGGTGAAGTGAAGCAGCCTGGGGCCTC

AGTGAAGATCTCCTGCAAAGCCTCTGGATTCAATTTTAACAATGAAGATG

TGCACTGGGTGCGACAGGCCGCTGGACAAGGTCTGGAGTGGATGGCATGG

TCGAAACATGACGATCAAAATGTTTTGTATGCACAAGAATTTAAGGACAG

-continued

GGTCACCGTGACGAGGGACACCGCCGCAAATACAGTCTACATTCAGATGA

CCGGTCTGAGATTTGAAGACACGGCCCTCTATTATTGTGTTAAGGGCTCA

AAGTTTAGGCTGAGGGAGTGGGCTGATTACAATGAATGGGGCCTAGTTTC

GGCTCAACATGGAGACTACGTGACGCAGTTGGGCATCTGGGGCCAGGGGA

CCGCGATCTACGTCTCGTCA

PGDM_1404_HC (SEQ ID NO: 5)

CAGGTGTTTTTGGAACAGTCTGGGGGTGAGGTGAGGAGGCCTGGGGCCTC

AGTGAAGGTCTCCTGCAAGGCCACTGGATTCACCTTCCGTAATGATGATG

TTCACTGGGTGCGACAGGCCACTGGCCAAGGGCCTGAGTGCGTGGCTTGG

ATGAAGCATGACGATCAAAGTACAGTCTTTCCAAAGAAGTTCCAGGGCAG

AGTCATCGTGACAACGGACACCTCCGCAACAACAGTCTACATGGAGATGG

GGGGCCTGATGCCTGAAGACACGGCCATTTATTACTGTGTAAGAGGCGCA

AAATTTCGGTTGAGACATGACGCCACTTATGATTACTGGAACGACTTACT

TTGGGCTGACGACCGTGACTACGTGACGCAGTTAGACCTTTGGGGCCCAG

GGACCGCTATCATTGTCTCCGCA

PGDM_1405_HC (SEQ ID NO: 6)

CAGGTGTTTTTGGAACAATCTGGGGGTGAAATAAAGAGGCCTGGGGCCTC

AGTGAAGGTCTCCTGCAAGGCCACTGGATTCACCTTCCATCACGATGATG

TTCACTGGGTGCGACAGGCCACTGGCCAAGGGCCTGAGTGCGTGGCTTGG

ATGAAACATGACGATCAAAGTACAGTCTATCCACAGAAGTTCCAGGGCAG

AGTCACCGTGACAAGCGACACCTCCGGTACAACAGTCTATATGGAGATGG

GGGGACTGATGCCTGAAGACACGGCCATTTATTACTGTGTCAGAGGCGCA

AAGTTCAGGTTGAGACATGACGCAACATATGATTACTACAATGACTTGCT

TTGGGCTGACGACCGTGACTACGTGACGCAGTTGGACCTTTGGGGCCAAG

GGACCGCGATCATCGTCTCCGCA

PGDM_1406_HC (SEQ ID NO: 7)

CAAGTCCAGGTGGACCAGTCCGGGGGTGAGGTGAAGAAGCCTGGGGCCTC

AGTGAGGGTCTCCTGCAAGGCCTCGGGATTCTCTTTTAAGAGTGAAGATA

TGCACTGGGTGCGACAGGCCGCTGGACGAGGGCTGGAGTGGATGGCATGG

GTAAAACATGACAGTGATGAAATATTATATTCAGAAAAGTTTAAGGACAG

GGTCATCGTGACCAGGAACACCGCCTCAAACACAATCTCCATGGACATGA

CCGGTCTGACATCTGAAGACACGGCCCGATATTATTGTGTGAAAGGCCAA

AAGTTCAGGCTGACAGAGTGGGCTGACTACAATGAATTCGGCCTAGTGGC

GGCTCAAAAAGGAGACTACGTGACACAGCTGGACGTCTGGGGCCAGGGGA

CCGACATCATCGTCTCGTCA

PGDM_1407_HC (SEQ ID NO: 8)

CAAGTCAAGTTGGACCAGTCCGGGGGTGAGGTGAAGAAGCCTGGGGCCTC

AGTGACGGTCTCCTGCAAGGCCTCTGGATTTAGTTTTGGAAGTGAAGATG

TACACTGGGTGCGACAGGCCGCTAGGGGAGGGCTGGACTGGATGGCATGG

GTGAAACATGACAGTCATGAAATTTTATACGCACAGAAATTTAAGGGCAG

GGTCACCGTGACCAGGAACACCGCCTCAAACACAGTCTTCATGGAGATGA

-continued

CCGGTCTGACATCTGAAGACACGGCCCGATATTATTGTGTGAAAGGTCAA

AAGTTTCGGCTGACAGAGTGGGCTGACTATAATGAATTCGGCCTGGTGGC

GGCTGAAAAAGGAGACTACGTGACACAACTGGACGTCTGGGGCCAGGGGA

CCGCGATCATCGTCTCGTCA

PGDM_1408_HC (SEQ ID NO: 9)

CAGGCGCAACTGGTACAGTCTGGGCCTGAGATGAGGAGTCCTGGGGCCTC

CGTAAAGGTCTCCTGCAAGGCCCCTGGAAATACATTGAAGAATCATGATC

TACACTGGGTGCGCAACGTCCCTGGACAGGGGCTTGAGTGGGTGGGGTGG

GTGAGTCACGAGGGCGACAAAAACGTCATTATAGAGAAATTCAAGGCCAG

AGTCACCATTGATTGGGACAGGTCCCTGAATACGGCCTATCTGCAACTGC

GCGGCCTCAGGTCTGAGGACACGGCCGTCTATTATTGTGCGAGAGGGTCA

AAACACAAGCTGCGAGACTACGTTATGTACGACGACTATGGCGCATTGCA

GTGGGCTGTTTATGTTGACTATCTTTCGAACTTGGACGTCTGGGGCCAGG

GGACCGCCGTCACCGTCTCTCCA

PGDM_1409_HC (SEQ ID NO: 10)

CAGGTGTTTTTGGAACAATCTGGGGGTGAAGTAAAGAGGCCTGGGGCCTC

AGTGAAGGTCTCCTGCAAGGCCACTGGATTCACCTTCCGTCAAAATGATG

TTCACTGGGTGCGACAGGCCACTGGCCAAGGGCCTGAGTGCGTGGCTTGG

ATGAAACATGACGATCAAAGTACAGTCCTTCCACAGAAGTTCCAGGGCAG

AGTCACCGTGACAAGCGACACCTCCGCTACAACAGTCTATATGGAGATGG

GGGGACTGATGCCTGAAGACACGGCCATTTATTACTGTGTCAGAGGCGCA

AAGTTCAGGTTGAGACATGACGCAACATATGATTACTGGAATGACTTGCT

TTGGGCTGACGACCGTGACTACGTGACGCAGTTGGACCTTTGGGGCCAAG

GGACCGCGATCATCGTCTCCGC

PGDM_1410_HC (SEQ ID NO: 11)

CAGGTGTTTTTGGAGCAGTCTGGGGGTGAGGTGAGGAGGCCTGGGGCCTC

AGTAAACGTCTCCTGCAAGGCCACTGGATTCACCTTCCATCATCATGATG

TTCATTGGGTGCGACAGGCCACTGGCCAAGGGCCTGAGTGTGTGGCGTGG

ATGAAACATGACGATCAAAGTACAGTCTTTCCACAGAAGTTCCAGGGCAG

AGTCACCGTGACAAGGGACACCTCCGCTAAAATAGTTTATATGCAGATGG

GGGGACTGATGCCTGAAGACACGGCCATATATTATTGTGTGAGAGGCTCA

AAATTTAGGTTGAGAAATGACGCTATCTACGATTATTGGAACGACTTACT

TTGGGCTGACGACGGTGACTACGTGACGAAGTTGGACCTTTGGGGCCATG

GGACCGCGATCATCGTCTCCTCA

PGDM_1411_HC (SEQ ID NO: 12)

CAGGTGCAATTGGTGCAGTCTGGAGCCGAGGTGAGGAAGCCTGGGACCTC

AGTGAAAATCTCCTGCACGACCTCTGGATATTCTTTCAACAGTCATCATA

TCCACTGGGTGCGACACGGCACCGGACAAGGACTTGAGTGGATTGGGTGG

GTGGACCCAAATAATGGTAATACAGGATATACACCAAAATTCAAGGACAG

AGTCACCTTTGTCAAGAATACCTCCACACAGACGGTGTTCATGGAAGTGA

-continued

CCAGTCTAAAATCTGAGGACACGGGCGTCTATTATTGTGCGAGACGGACA

GAAAAACAACTGAGAGCAGAGTATGTTCTGGACCAAGAAGACGGCTTTTA

TCGTGAAGAGGCCATTTACATCACAGTCCTGGACGTCTGGGGCCAAGGGA

CCGCGGTCGCCGTCTCCTCA

PGDM_1412_HC (SEQ ID NO: 13)

CAGGTACATCTGGAGCAGTCCGGGGGTGAGGTGAAGAAGCCTGGGGCGTC

GGTGAAGGTCTCCTGCAAGGCCTCTGGATTCACTTTTAGTAGTGATGATA

TGCACTGGGTGCGACAGGCCGCTGGACAAGGGCTGGAGTGGATGTCATGG

GTGAAACATGACAGTCATGAAATATTGGTTGGACAAAAGTTTAAGGACCG

GGTCATCGTGACCAGGAACACCGCCGCAAACACAGTCTACTTGGAAATGA

CCGGTCTGAGATCTGAAGACACGGCCACATATTATTGTGTAAAAGGTCTA

AAATTTAGGCTGAGAGAGTGGTCAGACTATAATGAATTCGGCCTAGTGGC

GGCTCAACATGGAGACTACGTGACACAAATGGAGGTCTGGGGCCAGGGGA

CCGCGATCAGCGTCTCCTCA

The nucleotide sequences of the light chains of PGDM1400, PGDM1401, PGDM1402, PGDM1403, PGDM1404, PGDM1405, PGDM1406, PGDM1407, PGDM1408, PGDM1409, PGDM1410, PGDM1411 and PGDM1412 are:

PGDM 1400 KC (SEQ ID NO: 14)

GATTTTGTCCTGACTCAGTCTCCACACTCTCTGTCCGTCACCCCTGGAGA

GTCGGCCTCCATCTCCTGCAAGTCTAGTCACAGCCTCATTCATGGTGATA

GGAACAATTATTTGGCTTGGTACGTACAGAAGCCAGGGCGGTCTCCACAA

CTCCTGATCTATTTGGCTTCCAGTCGGGCCTCCGGGGTCCCTGACAGGTT

CAGTGGCAGTGGATCGGACAAAGATTTTACACTGAAGATCAGCAGAGTGG

AGACTGAGGATGTTGGGACGTATTACTGCATGCAAGGTCGAGAAAGTCCC

TGGACGTTCGGCCAAGGGACCAAGGTGGACATCAAA

PGDM 1401 KC (SEQ ID NO: 15)

GATTTTGTCCTGACTCAGTCTCCACACTCTCTATCCGTCACCCCGGGAGA

GCCGGCCTCCATCTCCTGCAGGTCTAGTCAGAGCCTCCTTCATGGTGATA

AAAACAACTATTTGGCTTGGTATCTCCAGAAGCCAGGGCACTCTCCACAA

CTGCTGATCTATATGGCTTCTAGTCGGCCCTCAGGGGTCCCTGACAGGTT

CAGTGGCAGTGGCTCGGGCACACATTTTACACTGAAAATCAGTAGAGTGG

AGACTGAAGATGTTGGGATGTACTACTGCATGCAAGGTCGAGAAAGTCCC

TGGACGTTTGGCCAAGGGACCAAGGTGGAAATCAAA

PGDM 1402 KC (SEQ ID NO: 16)

GACTTTGTCCTGACTCAGTCTCCACACTCTCTGTCCGTCACCCCTGGAGA

GCCGGCCTCCATCTCCTGCAAGTCTAGTCACAGCCTCATTCATGGTGATA

AGAACAACTATTTGGCTTGGTACGTTCAGAAGCCAGGGCGGTCTCCACAA

CTCCTGATCTATTTGGCTTCCAGTCGGGCCTCCGGGGTCCCTGACAGGTT

CAGTGGCAGTGGATCGGACAAAGATTTTACACTGAAGATCAGCAGAGTGG

AGACTGAGGATGTTGGGACCTATTACTGCATGCAAGGTCGAGAAAGTCCC

TGGACGTTCGGCCAGGGGACCAAGGTGGAAATCAAA

-continued

PGDM 1403 KC (SEQ ID NO: 17)

AAAATTGCGTTGACTCAGTCTCCACTCTCCCTGGCCGTCACCCCTGGAGA

GCCGGCCTCCATTTCCTGCAGGTCAAGTCAGAGCCTCCTTTATAAGAATG

AACACAATGATGCATATATCGAATATACCTTCTTGAGTTGGTATCTGCAG

AGGCCAGGCCAGTCTCCACAACTCCTGATCTATTTGGGTTCTAAGCGGGC

CTCCGGGGTCCCTGGCAGGTTCAGTGGCGGTGGATCAGGCACAGATTTCA

CACTGAAAATCAGCAGAGTGGAGGCTGACGATGTGGGCACATATTACTGC

ATGCAAGGTCTACAAAGTCCCACGACGTTCGGCCAAGGGACCAAGTTGCA

GATCAAA

PGDM 1404 KC (SEQ ID NO: 18)

GATGTTGTGCTGACTCAATCTCCACTGTCCCTGTCCGTCAGTCCTGGAGA

GCCGGCCTCTATCTCCTGCAGGTCCAGTCAGAGTCTCCTGTGGAGTAAGG

ATGACACAAGATATGACTTTTTGGGATGGTATTTGCAGAAGCCTGGGCAG

CCTCCACGACTCCTCATCTATTTGGGTTCTCGTCGGGCCTCCGGGGTCCC

TGACAGGTTCAGCGCCAGTGGATCAGGCACAGACTTCACACTGAGAATTA

ACAGAGTGGAGGCTGCCGATTTCGGAACTTATTACTGCATGCAAGGGCGA

CACATTCCCTTGACGTTCGGCCAAGGGACCAGGGTGGAAATCAAT

PGDM 1405 KC (SEQ ID NO: 19)

GATGTTGTGCTGACTCAATCTCCACTCTCCCTGTCCGTTAGCCCTGGAGA

GCCGGCCTCGATCTCCTGCAGGTCCAGTCAGAGTCTCCTGTGGACTAAAG

ACCATCAAAGTTATAACTTTCTGGGATGGTATTTGCAGAAGCCTGGGCAG

CCTCCACGATTCCTAATTTCTTTGGGTTCTCGTCGGGCCAACGGGGTCCC

TGTCAGGTTCAGCGCCAGTGGATCAGGCACAGATTTCACACTGAAAATTA

GCAGAGTGCAGACTGACGATGTTGGAATTTACTACTGCATGCAAGGTCGA

CACATTCCCTTGACCTTCGGCCAAGGGACCAAGGTGGAAATCAAT

PGDM 1406 KC (SEQ ID NO: 20)

GAAATCGTGCTGACTCAGTCTCCACTCTCCCTGGGCGTCTCCCCTGGAGA

GGCGGCCTCCATCTCCTGCAGGTCTAATCAGGACCTCTTGTATAAGAATG

ACCACAATCAGGTTTATAAGGAATACACCTTTGTGAGTTGGTACGTGCAG

AGGCCGGGCCAGTCTCCACAACTCCTGATCTATTTGGCTTCTCAGCGGGC

CGCCGGGGTCCCTGACAGGTTCAGTGGCGGTGGATCAGGCACAAATTTCA

CTCTAAAGATCAACAAAGTGGAGGCTGACGATGTGGGCATTTACTACTGC

ATGCAAGGTCTGCGAACTCCCATGACGTTCGGCCGAGGGACCAAGGTGGA

CATCAGG

PGDM 1407 KC (SEQ ID NO: 21)

GAGATCGTCCTGACTCAGTCTCCGCTCTCCCTAGGCGTCTCCCCTGGAGA

GACGGCCACCATCTCCTGCAGGTCTAATCAGGACCTCTTGTATAAGAATA

ACCACAACCAGGTTTATAGGGAGTACACCTTTGTGAGTTGGTACCTGCAG

AGGCCGGGCCAGTCTCCACAACTCCTGATCTATTTGGCTTCTACGCGGGC

CGCCGGGGTCCCTGACAGGTTCAGTGGCGGTGGATCAGGCACAAATTTCA

-continued

CTCTAAAAATCAACAAGGTGGAGGCTGACGACGTGGGCATTTACTACTGC

ATGCAAGGTCTACGAACTCCCATGACGTTCGGCCGAGGGACCCAGCTGGA

CATCAGG

PGDM 1408 KC (SEQ ID NO: 22)

GATTTTGTCCTGACTCAGTCTCCACATTCTCTATCCGTCACCCCGGGAGA

GCCGGCCTCCATCTCCTGCAGGTCTAGTCAGAGCCTCCTTCATGGTGATA

AAAACAACTATTTGGCTTGGTATCTCCAGAAGCCAGGGCACTCTCCACAG

CTGCTGATCTATATGGCTTCTAGTCGGCCCTCAGGGGTCCCTGACAGGTT

CAGTGGCAGTGGCTCGGGCACACATTTTACACTGAAAATCAGTAGAGTGG

AGACTGAAGATGTTGGGATGTACTACTGCATGCAAGGTCGAGAAAGTCCC

TGGACGTTTGGCCAAGGGACCAAGGTGGAAATCAAA

PGDM 1409 KC (SEQ ID NO: 23)

GATGTTGTGCTGACTCAATCTCCACTCTCCCTGTCCGTTAGCCCTGGAGA

GCCGGCCTCGATCTCCTGTAGGTCCAGTCAGAGTCTCCTGTGGACTAAAG

ACCATCAAAGTTATAACTTTCTGGGATGGTATTTGCAGAAGCCTGGGCAG

CCTCCACGATTCCTAATCTCTTTGGGTTCTCATCGGGCCTCCGGAGTCCC

TGACAGGTTCAGCGCCAGTGGCTCAGGCACAGATTTCACACTGAAAATTA

GCAGAGTGCAGACTGACGATGTTGGAACTTATTACTGCATGCAAGGTCGA

CACATTCCCTTGACGTTCGGCCAAGGGACCAAGGTGGAAATCAAG

PGDM 1410 KC (SEQ ID NO: 24)

GATGTTGTGATGACTCAGTCTCCACTCTCCCTGTCCGTCACCCCTGGAGA

GCCGGCCTCTATCTCCTGCAGGTCCAGTCAGAGCCTCCTGTGGAATAAGG

GTGATCAAAGATATAATTTTCTGGGATGGTATTTGCAGAAGCCTGGGCAG

CCTCCACGACTCCTAATGTATTTGGCTTCCAGTCGGGCCTCCGGGGTCCC

TGACAGGTTCAGCGGCAGAGGATCAGGCACAGACTTCACACTGAAAATTA

ACAGAGTGGAGGCTGACGATGTCGGAACTTATTACTGCTTCCAAGGTCGA

CACACTCCCTTGACGTTCGGCCAAGGGACCAAGGTGGAAATCAAT

PGDM 1411 KC (SEQ ID NO: 25)

CAGACTGTTCTGACTCAGTCGCCACTCTCCCTGGCCGTCACCCCTGGCGA

GCCGGCCTCCATCTCCTGTAAGTGTTCTCAGAACTTAAACGTTCAGGGAT

ACGATTTTGTGAGTTGGTATGTACAGAAACCAGGCCAATCTCCACGTCTC

CTGATGTACTCGTCTTCCCTGCGGGCCTCCGGGGTCCCTGACAGATTTAG

TGGCAGTGGATCCGCCACATCTTTTACACTTAAAATCAAGAGAGTCGAGC

CGGAAGATCTGGGGACTTATTACTGCATGGACACTCTACGCCCTCCCTAC

GCCTTCGGCCAGGGGACCAAGCTGGAGATCAGA

PGDM 1412 KC (SEQ ID NO: 26)

GAGATTGTGCTGAGTCAGTCTCCACTCTCCCTGGCCGTCACCCCTGGAGA

GCCGGCCTCCATCTCCTGCAGGTCTAGCCAGAGCCTCCTCTATAAGAATG

AACACAATGGTGTGTACAAAGAATATACCTTTTTGAGCTGGTACTTGCAG

AAGCCAGGCCAGTCCCCACAACTCCTGATGTATTTGGGTTCTACGCGGGC

GTCCGGGGTCCCTGGCAGGTTCAGTGGCGGTGGATCAGGCACAGATTTCA

-continued

CACTGAAAATCAGCAGAGTGGAGGCTGACGATGTGGGCACTTATTTCTGC

ATGCAAGGTCTTCAGGTTCCCATGACGTTCGGCCAAGGGACCAAGGTGGA

GATCAAA

In a particularly advantageous embodiment, the neutralizing antibody of the present invention have about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99% or about 100% sequence identity to the nucleic acid and/or amino acid sequences of the present invention.

The present invention also encompasses combinations of broadly neutralizing antibodies. Other broadly neutralizing antibodies include, but are not limited to, PG16, PG20, PGG14, PGC14, PG9, PGT-121, PGT-122, PGT-123, PGT-125, PGT-126, PGT-127, PGT-128, PGT-130, PGT-131, PGT-135, PGT-136, PGT-141, PGT-137, PGT-142, PGT-143, PGT-144, PGT-145, PGT-124, PGT-133, PGT-134, PGT-132, PGT-138, PGT-139, PGT-151, PGT-152, PGT-153, PGT-154, PGT-155, PGT-156, PGT-157 and PGT-158. In an advantageous embodiment, the combination is PGT121 and PGDM 1400.

PGT121 and PGDM 1400 together

| | PGT121 | PGDM1400 | PGT121 + PGDM1400 |
|---|---|---|---|
| Median IC50, μg/ml | 0.015 | 0.005 | 0.007 |
| % breadth | 63 | 80 | 98 |

In another embodiment of the present invention, the neutralizing antibody of the present invention may be crystallized in the combination with a soluble BG505 SOSIP.664 gp140 trimer or with any other HIV trimer to determine the exact molecular surface where the neutralizing antibody binds to the trimer to design novel HIV-1 immunogens.

Crystals of the invention may be obtained by conventional means as are well-known in the art of protein crystallography, including batch, liquid bridge, dialysis, vapor diffusion and hanging drop methods (see, e.g., Johnson et al., Biochemistry. 1982 Sep. 28; 21(20):4839-43; Brayer & McPherson, J Biol Chem. 1982 Apr. 10; 257(7):3359-61; McPherson & Weickmann, J Biomol Struct Dyn. 1990 April; 7(5):1053-60; and Koszelak et al., J Mol Biol. 1989 Sep. 20; 209(2):323-5; Weber et al., Acta Crystallogr B. 1991 Feb. 1; 47 (Pt 1):116-27 and Weber, Methods Enzymol. 1991; 202:727-41).

Generally, the crystals of the invention are grown by dissolving a substantially pure neutralizing antibody and trimer in an aqueous buffer containing a precipitant at a concentration just below that necessary to precipitate the protein. Water is removed by controlled evaporation to produce precipitating conditions, which are maintained until crystal growth ceases.

The crystals of the invention, and particularly the atomic structure co-ordinates obtained therefrom, have a wide variety of uses. The crystals and structure co-ordinates are particularly useful for identifying compounds that bind to the neutralizing antibody and thus are useful to elicit anti-HIV antibodies. Such compounds may be useful in eliciting clade B and C anti-HIV antibodies, however variants may be useful in eliciting clade A, D or E anti-HIV antibodies.

The structure co-ordinates may be used as phasing models in determining the crystal structures the neutralizing antibody as well as the structures of co-crystals of such domains with ligands.

The provision of the crystal structure of a neutralizing antibody complexed with a trimer provide the skilled artisan with a detailed insight into the mechanisms of action of a neutralizing antibody. This insight provides a means to design compounds that bind to a neutralizing antibody and thus to certain anti-HIV antibodies, and therefore compounds that elicit anti-HIV antibodies, which are useful in diagnosis, treatment, or prevention of HIV in an individual in need thereof.

The provision of the crystal structure of a neutralizing antibody complexed with a trimer allows a novel approach for drug or compound discovery, identification, and design for compounds that bind to a neutralizing antibody and thus to anti-HIV antibodies, and therefore compounds that elicit anti-HIV antibodies, which are useful in diagnosis, treatment, or prevention of HIV in an individual in need thereof. Accordingly, the invention provides a computer-based method of rational drug or compound design or identification which comprises: providing the structure of a neutralizing antibody complex as defined by the co-ordinates or the identifying co-ordinates, providing a structure of a candidate compound; and fitting the structure of the candidate to the structure of a neutralizing antibody.

In an alternative aspect, the method may use the co-ordinates of atoms of interest of a neutralizing antibody which are in the vicinity of the active site or binding region in order to model the pocket in which the substrate or ligand binds. These co-ordinates may be used to define a space which is then screened "in silico" against a candidate molecule. Thus, the invention provides a computer-based method of rational drug or compound design or identification which comprises: providing the co-ordinates of at least selected co-ordinates; providing the structure of a candidate compound; and fitting the structure of the candidate to the selected co-ordinates.

In practice, it may be desirable to model a sufficient number of atoms of a neutralizing antibody as defined by its co-ordinates which represent the active site or binding region. Thus, there can be provided the co-ordinates of at least 5, advantageously at least 10, more advantageously at least 50 and even more advantageously at least 100 atoms of the structure.

Accordingly, the methods of the invention can employ a sub-domain of interest of a neutralizing antibody which is in the vicinity of the active site or binding region, and the invention can provide a computer-based method for identifying or rationally designing a compound or drug which comprises: providing the coordinates of at least a sub-domain of; providing the structure of a candidate modulator or inhibitor of a neutralizing antibody and fitting the structure of the candidate to the co-ordinates of the sub-domain provided.

The invention further provides a method for determining the structure of a binder of a neutralizing antibody bound to a neutralizing antibody comprising: providing a crystal of a neutralizing antibody e.g., according to the invention, soaking the crystal with the binder, and determining the structure of the neutralizing antibody-binder complex. Alternatively or additionally the neutralizing antibody and the binder may be co-crystallized.

The invention also provides a method of analyzing a complex of a neutralizing antibody and a potential binder comprising: employing X-ray crystallographic diffraction data from the complex and a three-dimensional structure of a neutralizing antibody or at least a sub-domain thereof, to generate a different Fourier electron density map of the complex; advantageously, the three-dimensional structure being as defined by its atomic co-ordinate data.

Such complexes can be crystallized and analyzed using X-ray diffraction methods, e.g., according to the approaches described by Greer et al., 1994, and difference Fourier electron density maps can be calculated based on X-ray diffraction patterns of soaked or co-crystallized neutralizing antibody, and the solved structure of an uncomplexed neutralizing antibody. These maps can then be used to determine whether and where a particular potential binder binds to a neutralizing antibody and/or changes the conformation of a neutralizing antibody. Electron density maps can be calculated using programs such as those from the CCP4 computer package (Collaborative Computing Project, No. 4. The CCP4 Suite: Programs for Protein Crystallography, Acta Crystallographica, D50, 1994, 760-763). For map visualization and model building programs such as "QUANTA" (1994, San Diego, Calif.: Molecular Simulations, Jones et al., 1991) can be used.

Determination of the 3D structure of a neutralizing antibody provides important information about the likely active/binding site(s) of a neutralizing antibody. This information may be used for rational design of neutralizing antibody binders, e.g., by computational techniques that identify possible binding ligands for the active site(s), by enabling linked-fragment approaches to drug design, and by enabling the identification and location of bound ligands using analyses such as X-ray crystallographic analysis.

The terms "protein", "peptide", "polypeptide", and "amino acid sequence" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

As used herein, the terms "antigen" or "immunogen" are used interchangeably to refer to a substance, typically a protein, which is capable of inducing an immune response in a subject. The term also refers to proteins that are immunologically active in the sense that once administered to a subject (either directly or by administering to the subject a nucleotide sequence or vector that encodes the protein) is able to evoke an immune response of the humoral and/or cellular type directed against that protein.

The term "antibody" includes intact molecules as well as fragments thereof, such as Fab, $F(ab')_2$, Fv and scFv which are capable of binding the epitope determinant. These antibody fragments retain some ability to selectively bind with its antigen or receptor and include, for example:

Fab, the fragment which contains a monovalent antigen-binding fragment of an antibody molecule can be produced by digestion of whole antibody with the enzyme papain to yield an intact light chain and a portion of one heavy chain;

Fab', the fragment of an antibody molecule can be obtained by treating whole antibody with pepsin, followed by reduction, to yield an intact light chain and a portion of the heavy chain; two Fab' fragments are obtained per antibody molecule;

$F(ab')_2$, the fragment of the antibody that can be obtained by treating whole antibody with the enzyme pepsin without subsequent reduction; $F(ab')_2$ is a dimer of two Fab' fragments held together by two disulfide bonds;

scFv, including a genetically engineered fragment containing the variable region of a heavy and a light chain as a fused single chain molecule.

General methods of making these fragments are known in the art. (See for example, Harlow and Lane, Antibodies: A Laboratory Manual, Cold Spring Harbor Laboratory, New York (1988), which is incorporated herein by reference).

A "neutralizing antibody" may inhibit the entry of HIV-1 virus F with a neutralization index >1.5 or >2.0. Broad and potent neutralizing antibodies may neutralize greater than about 50% of HIV-1 viruses (from diverse clades and different strains within a clade) in a neutralization assay. The inhibitory concentration of the monoclonal antibody may be less than about 25 mg/ml to neutralize about 50% of the input virus in the neutralization assay.

It should be understood that the proteins, including the antibodies of the invention may differ from the exact sequences illustrated and described herein. Thus, the invention contemplates deletions, additions and substitutions to the sequences shown, so long as the sequences function in accordance with the methods of the invention. In this regard, particularly preferred substitutions are generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the sequences illustrated and described but possessing minor amino acid substitutions that do not substantially affect the immunogenicity of the protein are, therefore, within the scope of the invention.

As used herein the terms "nucleotide sequences" and "nucleic acid sequences" refer to deoxyribonucleic acid (DNA) or ribonucleic acid (RNA) sequences, including, without limitation, messenger RNA (mRNA), DNA/RNA hybrids, or synthetic nucleic acids. The nucleic acid can be single-stranded, or partially or completely double-stranded (duplex). Duplex nucleic acids can be homoduplex or heteroduplex.

As used herein the term "transgene" may be used to refer to "recombinant" nucleotide sequences that may be derived from any of the nucleotide sequences encoding the proteins of the present invention. The term "recombinant" means a nucleotide sequence that has been manipulated "by man" and which does not occur in nature, or is linked to another nucleotide sequence or found in a different arrangement in nature. It is understood that manipulated "by man" means manipulated by some artificial means, including by use of machines, codon optimization, restriction enzymes, etc.

For example, in one embodiment the nucleotide sequences may be mutated such that the activity of the encoded proteins in vivo is abrogated. In another embodiment the nucleotide sequences may be codon optimized, for example the codons may be optimized for human use. In preferred embodiments the nucleotide sequences of the invention are both mutated to abrogate the normal in vivo function of the encoded proteins, and codon optimized for human use. For example, each of the Gag, Pol, Env, Nef, RT, and Int sequences of the invention may be altered in these ways.

As regards codon optimization, the nucleic acid molecules of the invention have a nucleotide sequence that encodes the antibodies of the invention and can be designed to employ codons that are used in the genes of the subject in which the antibody is to be produced. Many viruses, including HIV and other lentiviruses, use a large number of rare codons and, by altering these codons to correspond to codons commonly used in the desired subject, enhanced expression of the antigens can be achieved. In a preferred embodiment, the codons used are "humanized" codons, i.e., the codons are those that appear frequently in highly expressed human genes (Andre et al., J. Virol. 72:1497-1503, 1998) instead of those codons that are frequently used by HIV. Such codon usage provides for efficient expression of the antibodies in human cells. Any suitable method of codon optimization may be used. Such methods, and the selection of such methods, are well known to those of skill in the art. In addition, there are several companies that will optimize codons of sequences, such as Geneart (geneart.com). Thus, the nucleotide sequences of the invention can readily be codon optimized.

The invention further encompasses nucleotide sequences encoding functionally equivalent variants and derivatives of the antibodies of the invention and functionally equivalent fragments thereof. These functionally equivalent variants, derivatives, and fragments display the ability to retain antibody activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan. In one embodiment, the variants have at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98% or at least 99% homology or identity to the antigen, epitope, immunogen, peptide or polypeptide of interest.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

The various recombinant nucleotide sequences and antibodies of the invention are made using standard recombinant DNA and cloning techniques. Such techniques are well known to those of skill in the art. See for example, "Molecular Cloning: A Laboratory Manual", second edition (Sambrook et al. 1989).

The nucleotide sequences of the present invention may be inserted into "vectors." The term "vector" is widely used and understood by those of skill in the art, and as used herein the term "vector" is used consistent with its meaning to those of skill in the art. For example, the term "vector" is commonly used by those skilled in the art to refer to a vehicle that allows or facilitates the transfer of nucleic acid molecules from one environment to another or that allows or facilitates the manipulation of a nucleic acid molecule.

Any vector that allows expression of the antibodies of the present invention may be used in accordance with the present invention. In certain embodiments, the antigens and/or antibodies of the present invention may be used in vitro (such as using cell-free expression systems) and/or in cultured cells grown in vitro in order to produce the encoded HIV-antigens and/or antibodies which may then be used for various applications such as in the production of proteinaceous vaccines. For such applications, any vector that allows expression of the antigens and/or antibodies in vitro and/or in cultured cells may be used.

For applications where it is desired that the antibodies be expressed in vivo, for example when the transgenes of the invention are used in DNA or DNA-containing vaccines, any vector that allows for the expression of the antibodies of the present invention and is safe for use in vivo may be used. In preferred embodiments the vectors used are safe for use in humans, mammals and/or laboratory animals.

'Vector' includes shuttle and expression vectors. Typically, the plasmid construct will also include an origin of replication (e.g., the ColE1 origin of replication) and a selectable marker (e.g., ampicillin or tetracycline resistance), for replication and selection, respectively, of the plasmids in bacteria. An 'expression vector' refers to a vector that contains the necessary control sequences or regulatory elements for expression of the antibodies including antibody fragment of the invention, in bacterial or eukaryotic cells. Suitable vectors are disclosed below.

A number of viral-based expression systems are available for mammalian expression of polypeptides. For example, in cases where an adenovirus is used as an expression vector, sequences encoding a polypeptide of interest may be ligated into an adenovirus transcription/translation complex consisting of the late promoter and tripartite leader sequence. Insertion in a non-essential E1 or E3 region of the viral genome may be used to obtain a viable virus that is capable of expressing the polypeptide in infected host cells (Logan, J. and Shenk, T. (1984) Proc. Natl. Acad. Sci. 81:3655-3659). In addition, transcription enhancers, such as the Rous sarcoma virus (RSV) enhancer, may be used to increase expression in mammalian host cells.

A variety of expression vector/host systems are utilized to contain and express polynucleotide sequences. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

For long-term, high-yield production of recombinant proteins, stable expression is generally preferred.

For the antibodies of the present invention to be expressed, the protein coding sequence should be "operably linked" to regulatory or nucleic acid control sequences that direct transcription and translation of the protein. As used herein, a coding sequence and a nucleic acid control sequence or promoter are said to be "operably linked" when they are covalently linked in such a way as to place the expression or transcription and/or translation of the coding sequence under the influence or control of the nucleic acid control sequence. The "nucleic acid control sequence" can be any nucleic acid element, such as, but not limited to promoters, enhancers, IRES, introns, and other elements described herein that direct the expression of a nucleic acid sequence or coding sequence that is operably linked thereto. The term "promoter" will be used herein to refer to a group of transcriptional control modules that are clustered around the initiation site for RNA polymerase II and that when operationally linked to the protein coding sequences of the invention lead to the expression of the encoded protein. The expression of the transgenes of the present invention can be under the control of a constitutive promoter or of an inducible promoter, which initiates transcription only when exposed to some particular external stimulus, such as, without limitation, antibiotics such as tetracycline, hormones such as ecdysone, or heavy metals. The promoter can also be specific to a particular cell-type, tissue or organ. Many suitable promoters and enhancers are known in the art, and any such suitable promoter or enhancer may be used for expression of the transgenes of the invention. For example, suitable promoters and/or enhancers can be selected from the Eukaryotic Promoter Database (EPDB).

The vectors used in accordance with the present invention should typically be chosen such that they contain a suitable gene regulatory region, such as a promoter or enhancer, such that the antibodies of the invention can be expressed.

For example, when the aim is to express the antibodies of the invention in vitro, or in cultured cells, or in any prokaryotic or eukaryotic system for the purpose of producing the protein(s) encoded by that antibody, then any suitable vector can be used depending on the application. For example, plasmids, viral vectors, bacterial vectors, protozoal vectors, insect vectors, baculovirus expression vectors, yeast vectors, mammalian cell vectors, and the like, can be used. Suitable vectors can be selected by the skilled artisan taking into consideration the characteristics of the vector and the requirements for expressing the antibodies under the identified circumstances.

When the aim is to express the antibodies of the invention in vivo in a subject, for example in order to generate an immune response against an HIV-1 antigen and/or protective immunity against HIV-1, expression vectors that are suitable for expression on that subject, and that are safe for use in vivo, should be chosen. For example, in some embodiments it may be desired to express the antibodies of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. Any vectors that are suitable for such uses can be employed, and it is well within the capabilities of the skilled artisan to select a suitable vector. In some embodiments it may be preferred that the vectors used for these in vivo applications are attenuated to vector from amplifying in the subject. For example, if plasmid vectors are used, preferably they will lack an origin of replication that functions in the subject so as to enhance safety for in vivo use in the subject. If viral vectors are used, preferably they are attenuated or replication-defective in the subject, again, so as to enhance safety for in vivo use in the subject.

In preferred embodiments of the present invention viral vectors are used. Viral expression vectors are well known to those skilled in the art and include, for example, viruses such as adenoviruses, adeno-associated viruses (AAV), alphaviruses, herpesviruses, retroviruses and poxviruses, including avipox viruses, attenuated poxviruses, vaccinia viruses, and particularly, the modified vaccinia Ankara virus (MVA; ATCC Accession No. VR-1566). Such viruses, when used as expression vectors are innately non-pathogenic in the selected subjects such as humans or have been modified to render them non-pathogenic in the selected subjects. For example, replication-defective adenoviruses and alphaviruses are well known and can be used as gene delivery vectors.

The nucleotide sequences and vectors of the invention can be delivered to cells, for example if aim is to express and the HIV-1 antigens in cells in order to produce and isolate the expressed proteins, such as from cells grown in culture. For expressing the antibodies in cells any suitable transfection, transformation, or gene delivery methods can be used. Such methods are well known by those skilled in the art, and one of skill in the art would readily be able to select a suitable method depending on the nature of the nucleotide sequences, vectors, and cell types used. For example, transfection, transformation, microinjection, infection, electroporation, lipofection, or liposome-mediated delivery could be used. Expression of the antibodies can be carried out in any suitable type of host cells, such as bacterial cells, yeast, insect cells, and mammalian cells. The antibodies of the invention can also be expressed using including in vitro transcription/translation systems. All of such methods are well known by those skilled in the art, and one of skill in the art would readily be able to select a suitable method depending on the nature of the nucleotide sequences, vectors, and cell types used.

The present invention also relates to ex vivo activation and expansion of lymphocytes. In particular, B cells expressing the antibodies of the present antibody may be expanded by binding to an antigen, such as, but not limited to, the BG505 SOSIP.664 gp140 trimer. The amplified B cells may be amplified and introduced to a subject in need thereof. To elicit a robust neutralizing antibody response to HIV-1, an understanding of B-cell biology is required. Immunogens must engage the appropriate naïve B-cell receptors to induce antibodies of the appropriate specificity. In addition, autoreactive B cells will be eliminated by clonal deletion, and the process of immunization likely must drive somatic mutations that are required for affinity maturation and development of high-affinity antibodies with the appropriate specificity. Critical to the success of rational vaccine design is the ability to take advantage of these factors and address the basic aspects of B-cell development that control antibody specificity and synthesis. For example, immunogens will need to engage the low-affinity germline precursors in a way that facilitates the development of high-affinity antibodies (see, e.g., Kwong P D et al., Cold Spring Harb Perspect Med 2011; 1:a007278).

In preferred embodiments, the nucleotide sequences, antibodies of the invention are administered in vivo, for example where the aim is to produce an immunogenic response in a subject. A "subject" in the context of the present invention may be any animal. For example, in some embodiments it may be desired to express the transgenes of the invention in a laboratory animal, such as for pre-clinical testing of the HIV-1 immunogenic compositions and vaccines of the invention. In other embodiments, it will be desirable to express the antibodies of the invention in human subjects, such as in clinical trials and for actual clinical use of the immunogenic compositions and vaccine of the invention. In preferred embodiments the subject is a human, for example a human that is infected with, or is at risk of infection with, HIV-1.

For such in vivo applications the nucleotide sequences, antibodies of the invention are preferably administered as a component of an immunogenic composition comprising the nucleotide sequences and/or antigens of the invention in admixture with a pharmaceutically acceptable carrier. The immunogenic compositions of the invention are useful to stimulate an immune response against HIV-1 and may be used as one or more components of a prophylactic or therapeutic vaccine against HIV-1 for the prevention, amelioration or treatment of AIDS. The nucleic acids and vectors of the invention are particularly useful for providing genetic vaccines, i.e. vaccines for delivering the nucleic acids encoding the antibodies of the invention to a subject, such as a human, such that the antibodies are then expressed in the subject to elicit an immune response.

The compositions of the invention may be injectable suspensions, solutions, sprays, lyophilized powders, syrups, elixirs and the like. Any suitable form of composition may be used. To prepare such a composition, a nucleic acid or vector of the invention, having the desired degree of purity, is mixed with one or more pharmaceutically acceptable carriers and/or excipients. The carriers and excipients must be "acceptable" in the sense of being compatible with the other ingredients of the composition. Acceptable carriers, excipients, or stabilizers are nontoxic to recipients at the dosages and concentrations employed, and include, but are not limited to, water, saline, phosphate buffered saline, dextrose, glycerol, ethanol, or combinations thereof, buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

An immunogenic or immunological composition can also be formulated in the form of an oil-in-water emulsion. The oil-in-water emulsion can be based, for example, on light liquid paraffin oil (European Pharmacopea type); isoprenoid oil such as squalane, squalene, EICOSANE™ or tetratetracontane; oil resulting from the oligomerization of alkene(s), e.g., isobutene or decene; esters of acids or of alcohols containing a linear alkyl group, such as plant oils, ethyl oleate, propylene glycol di(caprylate/caprate), glyceryl tri (caprylate/caprate) or propylene glycol dioleate; esters of branched fatty acids or alcohols, e.g., isostearic acid esters. The oil advantageously is used in combination with emulsifiers to form the emulsion. The emulsifiers can be nonionic surfactants, such as esters of sorbitan, mannide (e.g., anhydromannitol oleate), glycerol, polyglycerol, propylene glycol, and oleic, isostearic, ricinoleic, or hydroxystearic acid, which are optionally ethoxylated, and polyoxypropylene-polyoxyethylene copolymer blocks, such as the Pluronic® products, e.g., L121. The adjuvant can be a mixture of emulsifier(s), micelle-forming agent, and oil such as that which is commercially available under the name Provax® (IDEC Pharmaceuticals, San Diego, Calif.).

The immunogenic compositions of the invention can contain additional substances, such as wetting or emulsifying agents, buffering agents, or adjuvants to enhance the effectiveness of the vaccines (Remington's Pharmaceutical Sciences, 18th edition, Mack Publishing Company, (ed.) 1980).

Adjuvants may also be included. Adjuvants include, but are not limited to, mineral salts (e.g., $AlK(SO_4)_2$, $AlNa(SO_4)_2$, $AlNH(SO_4)_2$, silica, alum, $Al(OH)_3$, $Ca_3(PO_4)_2$, kaolin, or carbon), polynucleotides with or without immune stimulating complexes (ISCOMs) (e.g., CpG oligonucleotides, such as those described in Chuang, T. H. et al, (2002) J. Leuk. Biol. 71(3): 538-44; Ahmad-Nejad, P. et al (2002) Eur. J. Immunol. 32(7): 1958-68; poly IC or poly AU acids, polyarginine with or without CpG (also known in the art as IC31; see Schellack, C. et al (2003) Proceedings of the 34$^{th}$ Annual Meeting of the German Society of Immunology; Lingnau, K. et al (2002) Vaccine 20(29-30): 3498-508), JuvaVax™ (U.S. Pat. No. 6,693,086), certain natural substances (e.g., wax D from Mycobacterium tuberculosis, substances found in Cornyebacterium parvum, Bordetella pertussis, or members of the genus Brucella), flagellin (Toll-like receptor 5 ligand; see McSorley, S. J. et al (2002) J. Immunol. 169(7): 3914-9), saponins such as QS21, QS17, and QS7 (U.S. Pat. Nos. 5,057,540; 5,650,398; 6,524,584; 6,645,495), monophosphoryl lipid A, in particular, 3-de-O-acylated monophosphoryl lipid A (3D-MPL), imiquimod (also known in the art as IQM and commercially available as Aldara®; U.S. Pat. Nos. 4,689,338; 5,238,944; Zuber, A. K. et al (2004) 22(13-14): 1791-8), and the CCR5 inhibitor CMPD167 (see Veazey, R. S. et al (2003) J. Exp. Med. 198: 1551-1562).

Aluminum hydroxide or phosphate (alum) are commonly used at 0.05 to 0.1% solution in phosphate buffered saline. Other adjuvants that can be used, especially with DNA vaccines, are cholera toxin, especially CTA1-DD/ISCOMs (see Mowat, A. M. et al (2001) J. Immunol. 167(6): 3398-405), polyphosphazenes (Allcock, H. R. (1998) App. Organometallic Chem. 12(10-11): 659-666; Payne, L. G. et al (1995) Pharm. Biotechnol. 6: 473-93), cytokines such as, but not limited to, IL-2, IL-4, GM-CSF, IL-12, IL-15 IGF-1, IFN-α, IFN-β, and IFN-γ (Boyer et al., (2002) J. Liposome Res. 121:137-142; WO01/095919), immunoregulatory proteins such as CD40L (ADX40; see, for example, WO03/063899), and the CD1a ligand of natural killer cells (also known as CRONY or α-galactosyl ceramide; see Green, T. D. et al, (2003) J. Virol. 77(3): 2046-2055), immunostimulatory fusion proteins such as IL-2 fused to the Fc fragment of immunoglobulins (Barouch et al., Science 290:486-492, 2000) and co-stimulatory molecules B7.1 and B7.2 (Boyer), all of which can be administered either as proteins or in the form of DNA, on the same expression vectors as those encoding the antigens of the invention or on separate expression vectors.

In an advantageous embodiment, the adjuvants may be lecithin combined with an acrylic polymer (Adjuplex-LAP), lecithin coated oil droplets in an oil-in-water emulsion (Adjuplex-LE) or lecithin and acrylic polymer in an oil-in-water emulsion (Adjuplex-LAO) (Advanced BioAdjuvants (ABA)).

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen and/or immunogenic composition. A controlled-release formulation can be prepared using appropriate macromolecules (for example, polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material such as, for example, polyesters, polyamino acids, hydrogels, polylactic acid, polyglycolic acid, copolymers of these acids, or ethylene vinylacetate copolymers. Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions. Such techniques are disclosed in New Trends and Developments in Vaccines, Voller et al. (eds.), University Park Press, Baltimore, Md., 1978 and Remington's Pharmaceutical Sciences, 16th edition.

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate.

Such techniques for measuring the immune response of the subject include but are not limited to, chromium release assays, tetramer binding assays, IFN-γ ELISPOT assays, IL-2 ELISPOT assays, intracellular cytokine assays, and other immunological detection assays, e.g., as detailed in the text "Antibodies: A Laboratory Manual" by Ed Harlow and David Lane.

When provided prophylactically, the immunogenic compositions of the invention are ideally administered to a subject in advance of HIV infection, or evidence of HIV infection, or in advance of any symptom due to AIDS, especially in high-risk subjects. The prophylactic administration of the immunogenic compositions can serve to provide protective immunity of a subject against HIV-1 infection or to prevent or attenuate the progression of AIDS in a subject already infected with HIV-1. When provided therapeutically, the immunogenic compositions can serve to ameliorate and treat AIDS symptoms and are advantageously used as soon after infection as possible, preferably before appearance of any symptoms of AIDS but may also be used at (or after) the onset of the disease symptoms.

The immunogenic compositions can be administered using any suitable delivery method including, but not limited to, intramuscular, intravenous, intradermal, mucosal, and topical delivery. Such techniques are well known to those of skill in the art. More specific examples of delivery methods are intramuscular injection, intradermal injection, and subcutaneous injection. However, delivery need not be limited to injection methods. Further, delivery of DNA to animal tissue has been achieved by cationic liposomes (Watanabe et al., (1994) Mol. Reprod. Dev. 38:268-274; and WO 96/20013), direct injection of naked DNA into animal muscle tissue (Robinson et al., (1993) Vaccine 11:957-960; Hoffman et al., (1994) Vaccine 12: 1529-1533; Xiang et al., (1994) Virology 199: 132-140; Webster et al., (1994) Vaccine 12: 1495-1498; Davis et al., (1994) Vaccine 12: 1503-1509; and Davis et al., (1993) Hum. Mol. Gen. 2: 1847-1851), or intradermal injection of DNA using "gene gun" technology (Johnston et al., (1994) Meth. Cell Biol. 43:353-365). Alternatively, delivery routes can be oral, intranasal or by any other suitable route. Delivery also be accomplished via a mucosal surface such as the anal, vaginal or oral mucosa.

Immunization schedules (or regimens) are well known for animals (including humans) and can be readily determined for the particular subject and immunogenic composition. Hence, the immunogens can be administered one or more times to the subject. Preferably, there is a set time interval between separate administrations of the immunogenic composition. While this interval varies for every subject, typically it ranges from 10 days to several weeks, and is often 2, 4, 6 or 8 weeks. For humans, the interval is typically from 2 to 6 weeks. The immunization regimes typically have from 1 to 6 administrations of the immunogenic composition, but may have as few as one or two or four. The methods of inducing an immune response can also include administration of an adjuvant with the immunogens. In some instances, annual, biannual or other long interval (5-10 years) booster immunization can supplement the initial immunization protocol.

The present methods also include a variety of prime-boost regimens, for example DNA prime-Adenovirus boost regimens. In these methods, one or more priming immunizations are followed by one or more boosting immunizations. The actual immunogenic composition can be the same or different for each immunization and the type of immunogenic composition (e.g., containing protein or expression vector), the route, and formulation of the immunogens can also be varied. For example, if an expression vector is used for the priming and boosting steps, it can either be of the same or different type (e.g., DNA or bacterial or viral expression vector). One useful prime-boost regimen provides for two priming immunizations, four weeks apart, followed by two boosting immunizations at 4 and 8 weeks after the last priming immunization. It should also be readily apparent to one of skill in the art that there are several permutations and combinations that are encompassed using the DNA, bacterial and viral expression vectors of the invention to provide priming and boosting regimens.

A specific embodiment of the invention provides methods of inducing an immune response against HIV in a subject by administering an immunogenic composition of the invention, preferably comprising an adenovirus vector containing DNA encoding one or more of the epitopes of the invention, one or more times to a subject wherein the epitopes are expressed at a level sufficient to induce a specific immune response in the subject. Such immunizations can be repeated multiple times at time intervals of at least 2, 4 or 6 weeks (or more) in accordance with a desired immunization regime.

The immunogenic compositions of the invention can be administered alone, or can be co-administered, or sequentially administered, with other HIV immunogens and/or HIV immunogenic compositions, e.g., with "other" immunological, antigenic or vaccine or therapeutic compositions thereby providing multivalent or "cocktail" or combination compositions of the invention and methods of employing them. Again, the ingredients and manner (sequential or co-administration) of administration, as well as dosages can be determined taking into consideration such factors as the age, sex, weight, species and condition of the particular subject, and the route of administration.

When used in combination, the other HIV immunogens can be administered at the same time or at different times as part of an overall immunization regime, e.g., as part of a prime-boost regimen or other immunization protocol. In an advantageous embodiment, the other HIV immunogen is env, preferably the HIV env trimer.

Many other HIV immunogens are known in the art, one such preferred immunogen is HIVA (described in WO 01/47955), which can be administered as a protein, on a plasmid (e.g., pTHr.HIVA) or in a viral vector (e.g., MVA-.HIVA). Another such HIV immunogen is RENTA (described in PCT/US2004/037699), which can also be administered as a protein, on a plasmid (e.g., pTHr.RENTA) or in a viral vector (e.g., MVA.RENTA).

For example, one method of inducing an immune response against HIV in a human subject may comprise administering at least one priming dose of an HIV immunogen and at least one boosting dose of an HIV immunogen, wherein the immunogen in each dose can be the same or different, provided that at least one of the immunogens is an epitope of the present invention, a nucleic acid encoding an epitope of the invention or an expression vector, preferably a VSV vector, encoding an epitope of the invention, and wherein the immunogens are administered in an amount or expressed at a level sufficient to induce an HIV-specific immune response in the subject. The HIV-specific immune response can include an HIV-specific T-cell immune response or an HIV-specific B-cell immune response. Such immunizations can be done at intervals, preferably of at least 2-6 or more weeks.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

A Recombinant HIV Envelope Trimer Selects for Quaternary-Dependent Antibodies Targeting the Trimer Apex Broadly neutralizing antibodies (bnAbs) targeting the trimer apex of HIV envelope (Env) are favored candidates for vaccine design and immunotherapy because of their great neutralization breadth and potency. Methods to isolate bnAbs against this site, however, have been limited due to the quaternary nature of the epitope region. Here Applicants report the use of a recombinant HIV envelope trimer, BG505 SOSIP.664 gp140, as an affinity reagent to isolate quaternary-dependent bnAbs from the PBMCs of a chronically infected donor. The new bnAbs, named PGDM1400-1412, show a wide range of neutralization breadth and potency. One of these variants, PGDM1400, is exceptionally broad and potent with cross-clade neutralization coverage of 83% at a median $IC_{50}$ of 0.003 μg/mL. Overall, Applicants' results highlight the utility of BG505 SOSIP.664 gp140 as a tool for the isolation of quaternary-dependent antibodies and reveal a mosaic of antibody responses against the trimer apex within a clonal family.

Despite the high antigenic diversity of HIV envelope (Env), broadly neutralizing antibodies (bnAbs) have identified conserved regions that serve as targets for vaccine design. One of these regions is located at the apex of the trimer and is only fully expressed in the context of the correctly folded trimer. This work describes the isolation of novel bnAbs that target the trimer apex using a recombinant native-like Env trimer as an affinity reagent to sort specific antibody-producing cells. Characterization of these antibodies reveals a highly diverse antibody response against the trimer apex and provides molecular information that will be useful in the design of immunogens to elicit bnAbs to the apex region of Env.

Multiple methods have been developed to isolate HIV broadly neutralizing antibodies (bnAbs) (1-12). Hybridoma and phage display techniques were used to isolate the first generation of bnAbs including b12, 2F5, 2G12, 4E10 and Z13 (13-20). These antibodies exhibit a range of neutralization breadth against primary isolates from 30-90%, but have moderate neutralization potency (median $IC_{50}$ of ~2-4 μg/mL). Access to infected donors who have high serum titers of bnAbs (21, 22) and the availability of newer approaches for isolating human mAbs have recently enabled the discovery of a new generation of more potent bnAbs (1-4, 6-8).

One of the newer approaches involves the sorting and activation of large numbers of memory B cells using cytokine-secreting feeder cells and the subsequent high-throughput screening of supernatants for neutralization. This method led to the identification and characterization of the first of the new generation of bnAbs, PG9 and PG16 (1), and has since revealed several new sites of vulnerability to bnAb recognition on Env (1-4, 6, 7). An alternative method for bnAb isolation involves the use of soluble Env molecules or scaffold proteins as baits to select single IgG+ memory B cells of interest by cell sorting (6, 8, 9, 23, 24). Soluble baits have not, however, been successful at isolating antibody responses targeting quaternary epitopes, including the trimer-apex site surrounding the N160 glycan, as the protein constructs used to date have not properly mimicked native Env trimers. To address this problem, GFP-labeled 293T cells that express cell surface Env for sorting, called GFP-293T$^{BaL}$, were used recently to isolate antibodies 3BC176 and 3BC315 (10, 25). These antibodies do not bind soluble monomeric gp120 but do bind Env trimer, demonstrating the utility of the approach, but the method was described to be inefficient compared to the use of soluble protein baits (10, 25).

The favorable antigenic profile of the soluble BG505 SOSIP.664 gp140 trimer opens the possibility of its use for isolating quaternary-specific antibodies by single-cell sorting (26). To this end, Applicants used BG505 SOSIP.664 gp140 to select for memory B cells from a donor from whom Applicants previously isolated the trimer-specific bnAbs PGT141-145 (3, 21). Applicants describe the isolation of novel somatic variants that are highly divergent from the PGT145 antibody family and display a range of neutralization breadth and potency, with some being more broad and potent than the previously described PGT145 family members. Overall, the results reveal a mosaic of antibody responses against the trimer-apex site of vulnerability that have important implications for immunogen design in general, as well as for the future optimization of BG505 SOSIP.664 and related native-like trimers as vaccine candidates.

Isolation of PGT145 Antibody Variants by Single-Cell Sorting. A variant of the BG505 SOSIP.664 gp140 trimer (26) bearing an Avi-tag sequence at the C-terminus was designed for site-specific biotinylation (BG505 SOSIP.664-AviB) and subsequent conjugation to streptavidin-fluorophores. After confirming that antigenicity was not affected following biotinylation (FIG. 5), Applicants used the BG505 SOSIP.664-AviB protein as bait to capture antigen-specific memory B cells from the PBMCs of IAVI Protocol G donor 84, who is the elite neutralizer from whom the bnAbs PGT141-145 were isolated (3). The PBMCs were from the same time point used for isolation of PGT141-145. As for previously established methods (6, 8), Applicants first excluded unwanted cell populations (CD3−/CD8−/CD14−) followed by positive selection for IgG memory B cells (CD19+/CD20+/IgG+/IgM−/IgD−). The memory population was simultaneously sorted for binding to BG505 SOSIP.664-AviB and lack of binding to biotinylated monomeric JR-CSF gp120 (JR-CSF gp120-AviB) (FIG. 1A). JR-CSF gp120 was included as a negative bait to select against antibodies binding non-functional trimers or monomers and was used in place of monomeric BG505 gp120 because this latter construct has been shown to bind to some quaternary trimer-apex preferring antibodies to some degree, specifically PG9 (26). The cells of interest were singly sorted into lysis buffer, and mRNA was reverse transcribed and amplified by single-cell polymerase chain reaction (PCR) to generate immunoglobulin G (IgG) heavy and light chain V genes (Table S2) (6, 27).

On average, one vial of 10 million PBMCs yielded approximately 100 cells that bound to BG505 SOSIP.664-AviB but not to JR-CSF gp120-AviB. From two vials, Applicants were able to obtain a total of 62 (31% recovery) heavy and 158 (83% recovery) kappa chain sequences (FIG. 1B). As shown in FIG. 1B, Applicants' sorting strategy strongly enriched for B cells that closely mimic PGT141-

145 (42% of the isolated heavy chain repertoire) in that they have extraordinarily long CDRH3s (33-34aa) and a mutation frequency of 21-27% from the $V_H$1-8 germline gene and 11-22% from the $V_K$2-28 germline gene (FIG. 1C and FIG. 1D and FIG. 6). While Applicants were also able to isolate antibodies deriving from other germline genes, Applicants chose to focus exclusively on those from the $V_H$1-8 gene with long CDRH3s.

Figure 8:
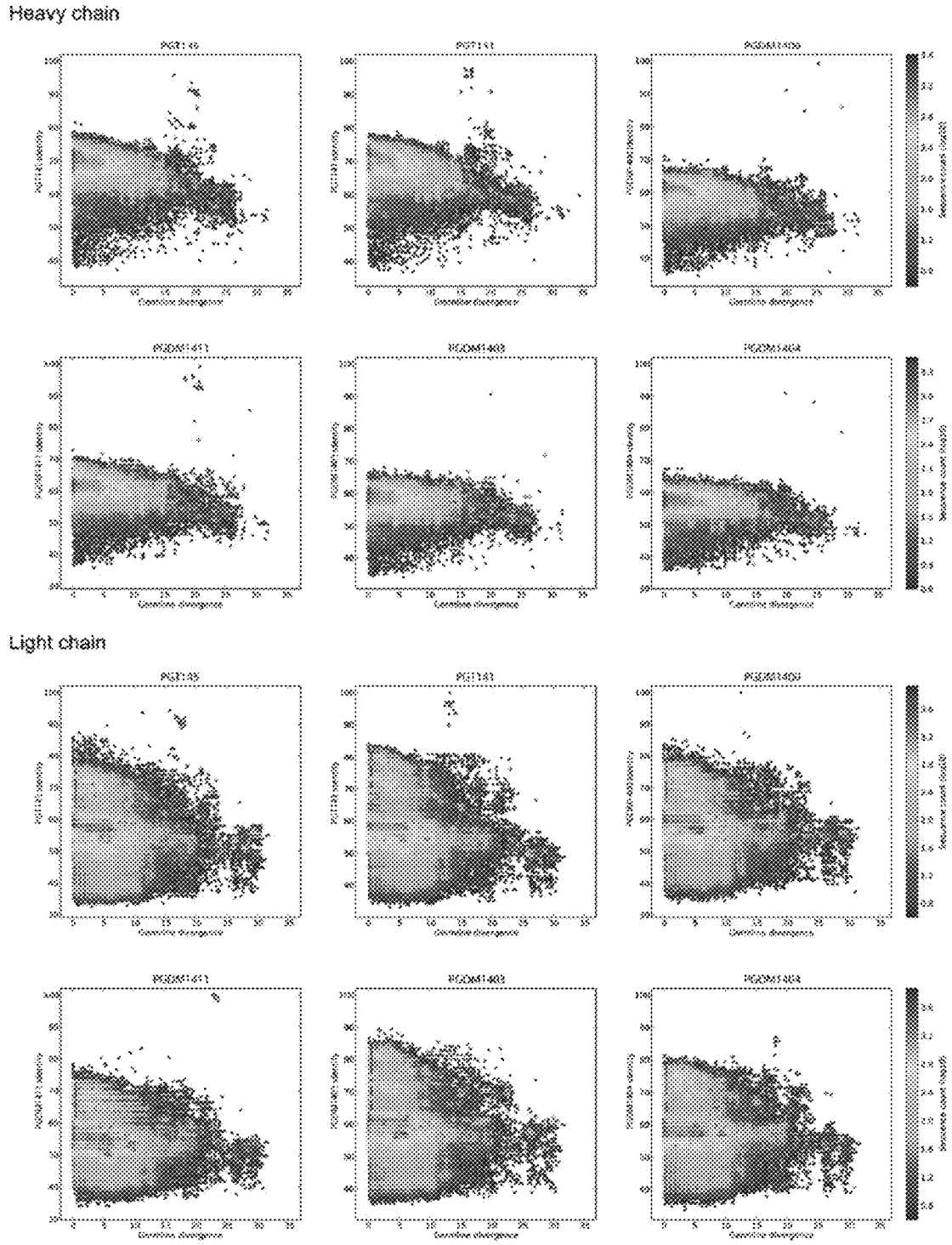
FIG. 8. Sequences of the newly isolated somatic variants can be found in a next-generation sequencing (NGS) dataset. Heavy-chain and light-chain sequences of the newly isolated somatic variants were queried in a previously published NGS dataset (Zhu J, et al.; NISC Comparative Sequencing Program (2013) Mining the antibodyome for HIV-1-neutralizing antibodies with next-generation sequencing and phylogenetic pairing of heavy/light chains. Proc Natl Acad Sci USA 110(16):6470-6475). The frequency of sequences is plotted in terms of percent identity to the listed antibody sequence and percent divergence from the germline gene. The number of sequences is colored according to the key.

Although Applicants noted considerable enrichment for PGT141-145-like heavy and light chain sequences, Applicants chose to clone and characterize only those sequences for which Applicants were able to amplify a heavy and light chain pair. Thus from 26 heavy chain and 35 light chain sequences, Applicants obtained 13 new somatic variants of the PGT145 antibody family that Applicants have named PGDM1400-1412 (FIG. 6). The new variants are highly divergent from the previously isolated PGT141-145 antibodies; they are only 49-67% similar by amino acid sequence (FIG. 7), but nevertheless are members of this family as judged by gene usage, CDRH3 length and CDRH3 sequence (FIG. 6). Interestingly, the somatic variants PGDM1403-1407 and PGDM1409-1412 appear to have developed insertions and deletions (indels) that are not present in the other somatic variants (FIG. 6). The sequences segregate into distinct clusters based on the overall sequence identity (FIG. 7), which is also evident when represented as phylogenetic trees for both heavy chain (FIG. 2A) and light chain (FIG. 2B). To corroborate their findings, Applicants were able to identify similar sequences in a previously published next-generation sequencing data set from the same donor for both heavy and light chain variants (FIG. 8) (28).

Figure 9:
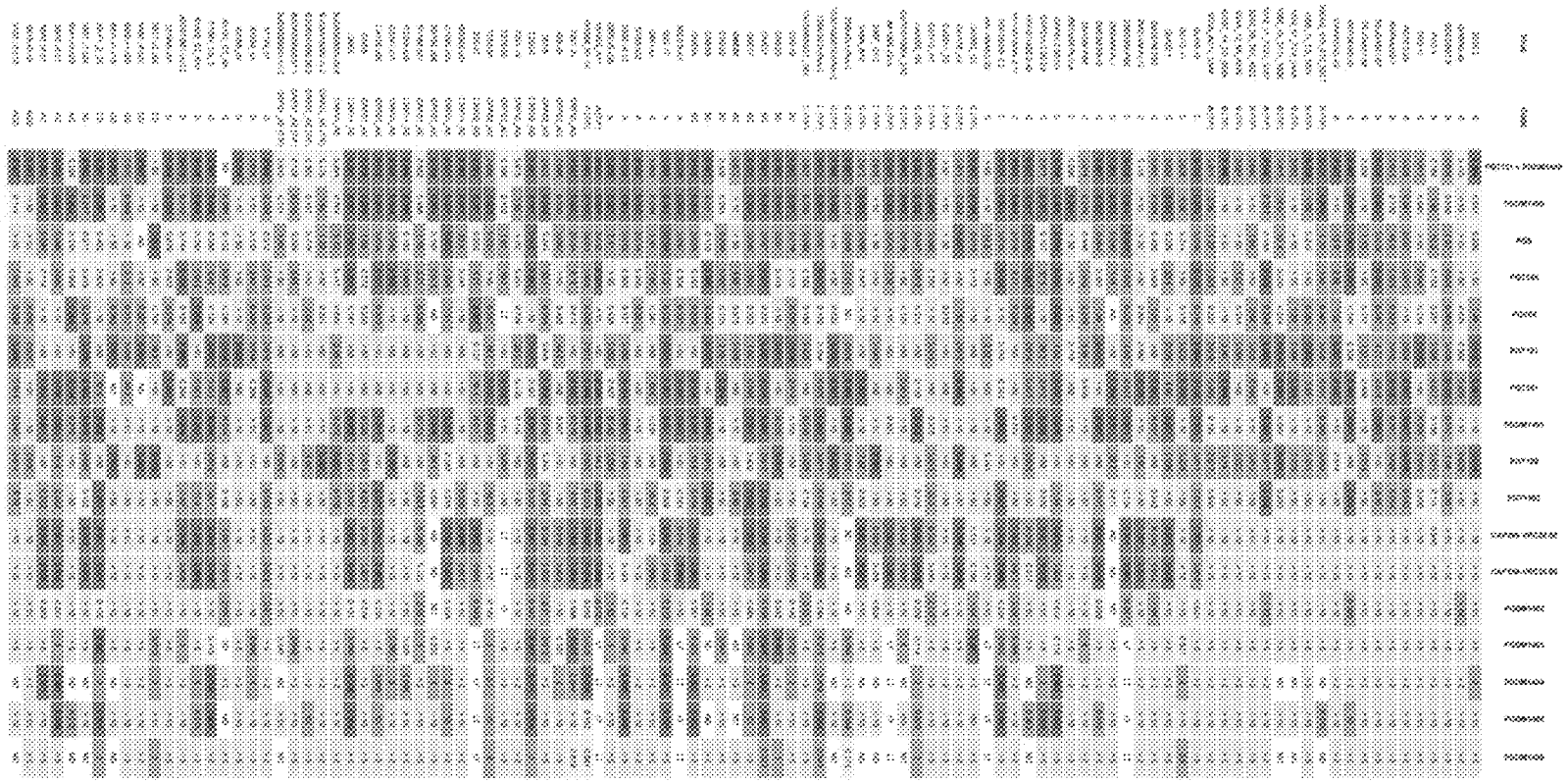
FIG. 9. Neutralization breadth and potency of somatic variants compared with other HIV-1 broadly neutralizing antibodies. Somatic variants were tested on a cross-clade pseudovirus panel. Neutralization IC50 values are colored from highly potent (red) to less potent (green). LT, viruses for which there were low titers; ND, not determined.

New Somatic Variants from the PGT145 Antibody Family Vary in their Neutralization Breadth and Potency. The new somatic variants PGDM1400-PGDM1406 were next tested on a cross-clade 77-pseudovirus panel and the neutralization breadths and median $IC_{50}$ values are presented by clade (FIG. 2C and FIG. 9). PG9 and the somatic variants PGT145 and PGT143 were included for comparison. Strikingly, despite sharing similar long CDRH3s and mutation frequencies, the new variants display a wide range of both neutralization breadth, from 83% to 6% coverage ($IC_{50}$ cut-off of 2 μg/mL due to low production of some variants), and potency, from 0.003 to 0.173 μg/mL in median $IC_{50}$. These results highlight the enormous range of neutralization breadth and potency that can be observed in a single family of related nAbs from a single donor.

Somatic Variant PGDM1400 is More Broad and Potent than Previously Reported bnAbs. Among the somatic variants characterized, the bnAb PGDM1400 stood out as having particularly broad and exceptionally potent neutralization activity. For a better comparison with previously described bnAbs, Applicants measured neutralization breadth and potency on a 106-virus panel (FIG. 9) and calculated neutralization breadth at different $IC_{50}$ cut-offs (FIG. 3A). These analyses confirmed that PGDM1400 is exceptionally potent; its median $IC_{50}$ of 0.003 μg/mL is markedly superior to PGT121 (3), PGT128 (3) or PGT151 (11, 12), which are among the most potent bnAbs described to date (FIG. 3A). Furthermore, PGDM1400 also possesses high neutralization breadth with 83% coverage (FIG. 3A). In addition, the combined neutralization coverage of PGDM1400 with PGT121 reaches an extremely high neutralization breadth and potency with 98% breadth at a median $IC_{50}$ of 0.007 μg/mL, demonstrating the protective potential of a vaccine designed to elicit antibodies against two epitopes (FIG. 3A). Finally, given the incomplete neutralization noted for other trimer-dependent antibodies like PGT151 and PG9, Applicants evaluated the maximum percent neutralization (MPN) of PGDM1400 in comparison to PGT121, PGT151, PG9, and 12A12. The results show that PGDM1400 exhibits complete neutralization for more viruses than PGT151 and is comparable to MPN levels of PGT121 (FIG. 10).

Applicants next wanted to compare possible structural differences between PGDM1400 and the previously isolated somatic variant PGT145 (3, 29). The structure of the PGDM1400 Fab determined at 3.1 Å resolution revealed that the 34-residue CDRH3 protrudes approximately 25 Å above the other residues and adopts an extended β-hairpin conformation similar to the CDRH3 of PGT145 (FIG. 3B) (29). CDR loops L1 and H2 appear to play a critical role in stabilizing the base of the elongated CDRH3 through an extensive network of H-bonding interactions (FIG. 3B). Sulfation is clearly observed in the electron density map for tyrosine at position 100F (Tys100F) (FIG. 3B). Unlike PGT145, which has two sulfated tyrosines exposed to solvent at the tip of the β-hairpin, sulfated Tys100F in PGDM1400 makes salt bridge interactions with Arg100A, evidently providing internal stability to the kinked β-hairpin structure (FIG. 3B). A major difference between PGDM1400 and PGT145 residues occurs at the tip of the CDRH3 in the 100G to 100R residue range, where only two out of 12 residues are identical. A triad of aspartic acid residues provides a highly anionic potential to the tip of the PGDM1400 CDRH3 (FIG. 3C), which likely interacts with cationic residues in the gp120 V1/V2, as seen for PG9 and PG16 (29, 30). The 2D-class averages of the PGDM1400 Fab-BG505 SOSIP gp140 trimer complex obtained by single-particle negative-stain electron microscopy revealed that only a single Fab is bound at the trimer apex and binds predominantly along the 3-fold axis compared to the shallower binding angle described for PG9 (FIG. 3D). PGDM1400, like other trimer-apex targeted bnAbs, such as PG9 (31) and CAP256-VRC26 (2), therefore targets the Env trimer with a stoichiometry of 1. Uncovering the atomic details of this interaction will be illuminating to decipher why PGDM1400 has such exceptional neutralization potency and breadth.

Figures 4, 4A, 4B, 4C, 4D, 4E:
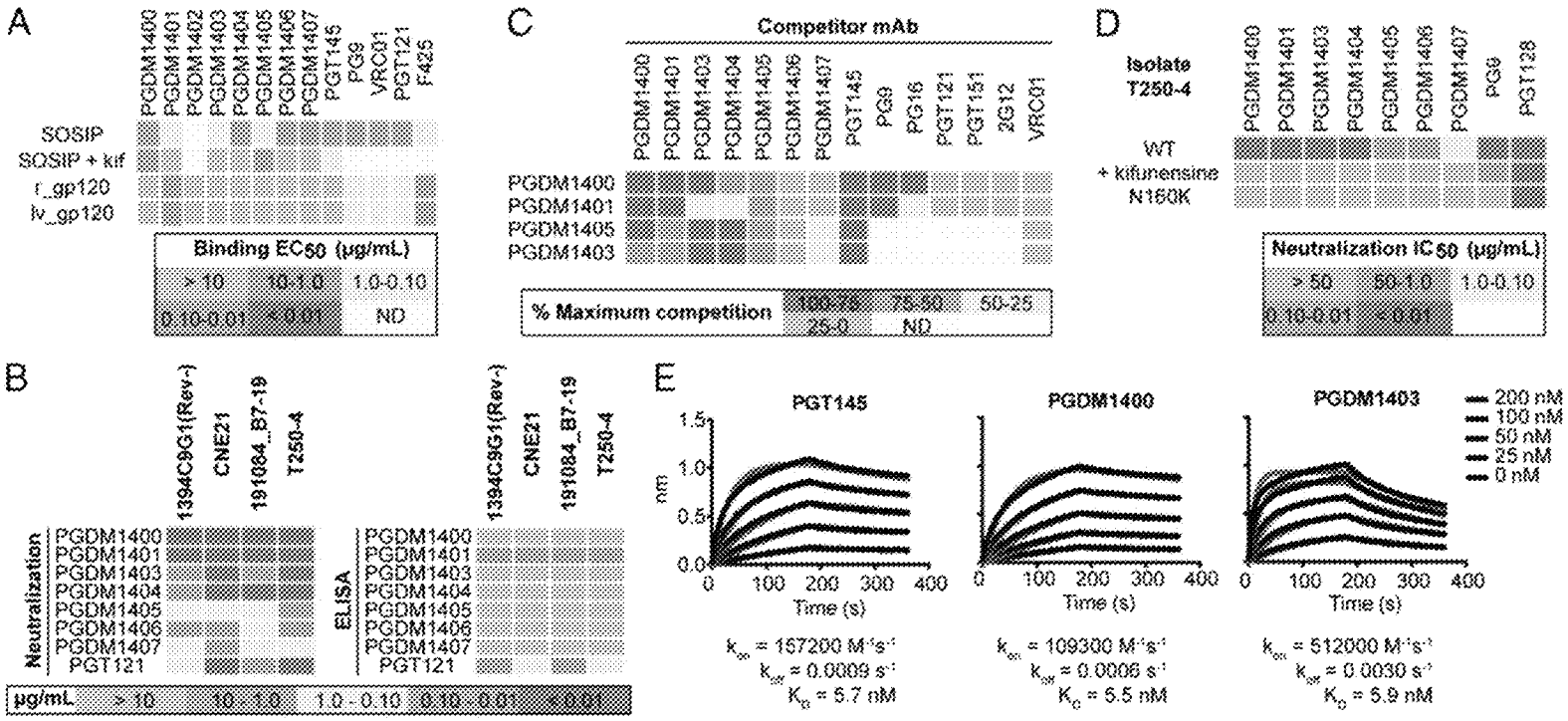
FIGS. 4A-E. Despite differences in neutralization, new somatic variants bind to the same region on Env.

Despite Differences in Neutralization Activity, New Somatic Variants Recognize a Similar Epitope. Considering the range of neutralization breadth and potency and the large sequence divergence between these clusters of somatic variants, Applicants next determined whether they all bound to the same Env region. First, Applicants tested binding to BG505 SOSIP-AviB by ELISA and found that all the somatic variants bound with varying affinities and that this binding was sensitive to the presence of particular glycoforms (FIG. 4A). Strikingly, despite binding to BG505 SOSIP-AviB by ELISA (FIG. 4A) and to cell surface BG505 Env (FIG. 11), some of the new somatic variants did not neutralize the pseudovirus (FIG. 11), suggesting there may be a subset of functional Env on virions that are not targeted by these somatic variants. To determine if the variants are still quaternary-specific, Applicants then tested binding to monomeric gp120. With one exception, PGDM1401, the somatic variants failed to bind to monomeric BG505 gp120 derived from lysed virions (lv_gp120) (FIG. 4A) or made as a recombinant protein in 293F cells (r_gp120) (FIG. 4A). This trimer binding preference was further corroborated for other isolates (FIG. 4B). Hence, Applicants conclude that the somatic variants, regardless of neutralization breadth, have a strong or absolute preference for Env trimers over gp120 monomers.

Figure 12:
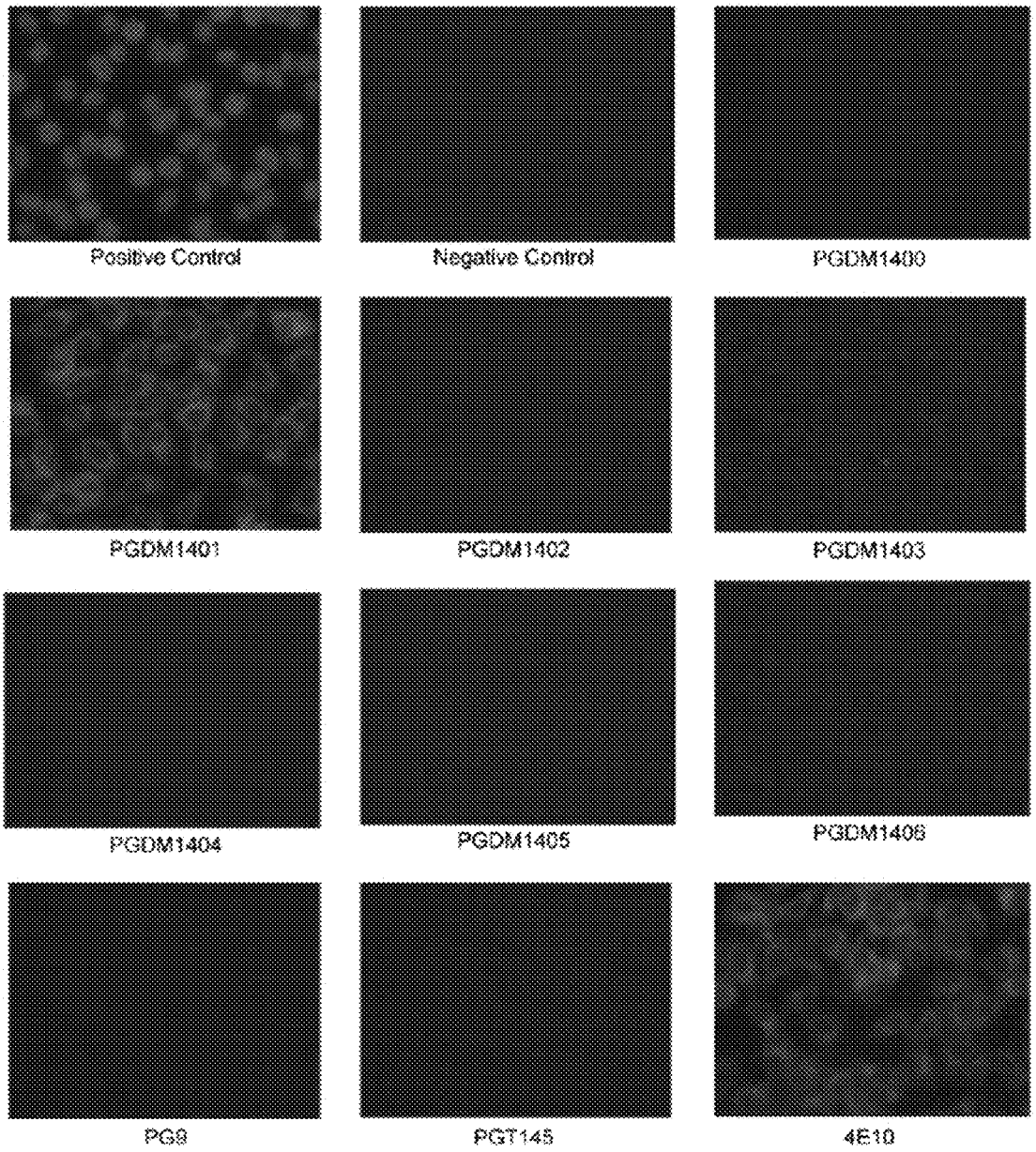
FIG. 12. Among the newly isolated somatic variants, only PGDM1401 is autoreactive by the HEp2 assay. Somatic variants were tested for autoreactivity using the HEp2 cell assay kit according to the manufacturer's protocol. 4E10 was included as a positive control.

To further probe the epitopes of the new somatic variants, Applicants performed competition ELISAs and confirmed that all the somatic variants competed strongly with one another, except for PGDM1406, which did not compete with any of the tested antibodies (FIG. 4C). It is possible that this antibody has a trimer binding affinity that is too weak to compete with the other somatic variants (FIG. 4A). When the most broad and potent somatic variants, PGDM1400 and PGDM1401, were also tested against a wider range of bnAbs, they competed only with those targeting the trimer-apex glycan epitope (FIG. 4C). Finally, as described for PGT141-145, Applicants confirmed that all of the new somatic variants are dependent on the N160 glycan for neutralization and showed reduced potency or loss of neutralization against pseudoviruses produced in the presence of kifunensine (FIG. 4D). Hence, despite differences in their neutralization activity, the overall data pattern strongly suggests that all somatic variants bind to the trimer-apex glycan epitope. Because of their N-linked glycan-dependency, Applicants also tested these new somatic variants for autoreactivity in a HEp2 assay (FIG. 12). With the exception of PGDM1401, none showed evidence of autoreactivity.

Figure 13:
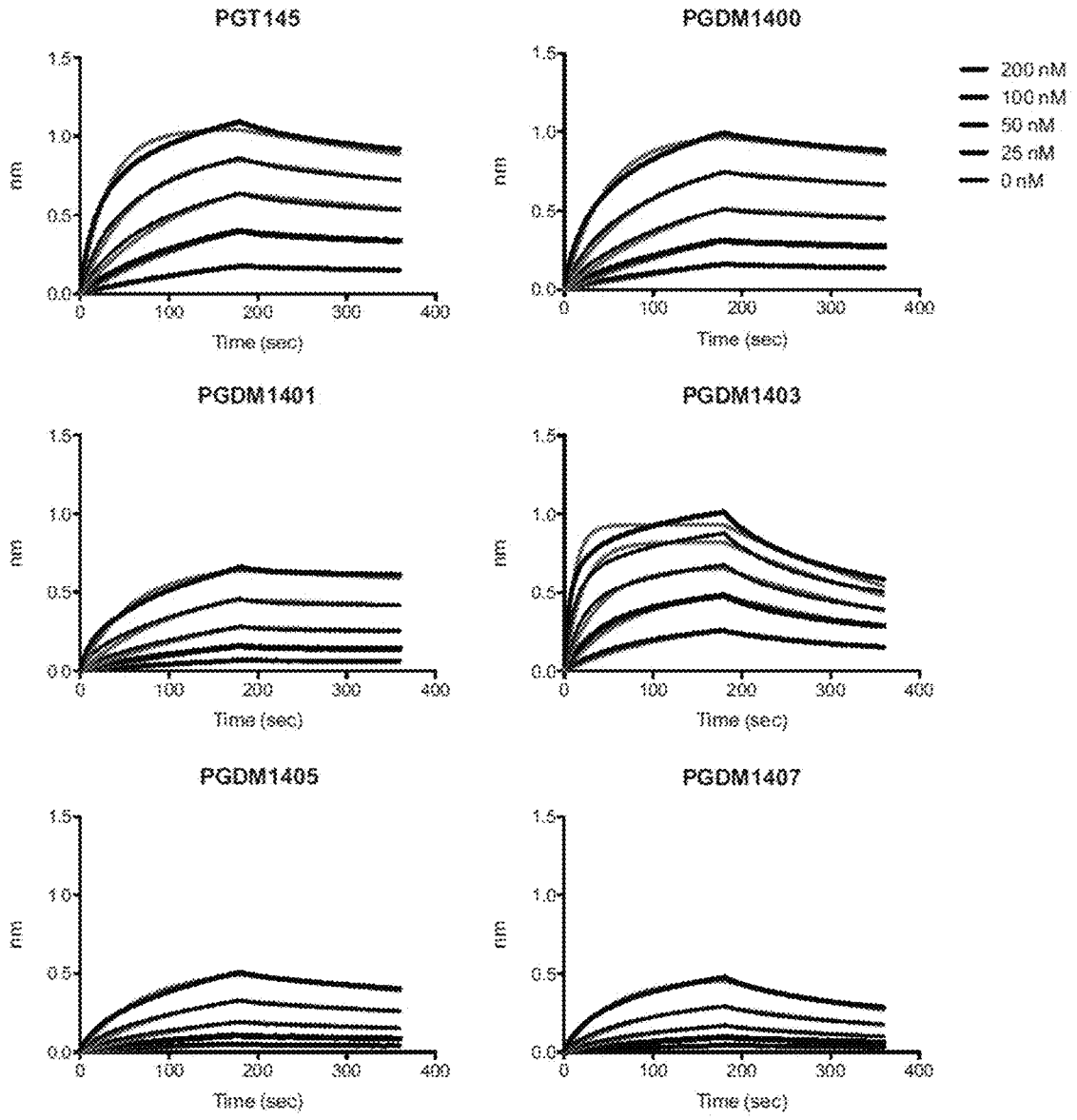
FIG. 13. Binding of mAbs to BG505 SOSIP.664-aviB by Octet. Antibodies PGT145, PGDM1400, PGDM1401, PGDM1403, PGDM1405, and PGDM1407 were analyzed for binding to BG505 SOSIP.664-AviB by Octet. Black curves represent measured data points; red curves represent best-fit lines following analysis.

Less Broadly Neutralizing Variants have Different Binding Kinetics than Broadly Neutralizing Variants. To test for possible explanations for neutralization differences observed between broadly neutralizing and non-broadly neutralizing variants, Applicants performed kinetic binding experiments by Octet (FIG. 4E and FIG. 13). Despite differences in neutralization of BG505 pseudovirus (FIG. 11), the results confirmed binding of both broadly neutralizing (PGT145 and PGDM1400) and non-broadly neutralizing (PGDM1403) antibodies to the BG505 SOSIP.664-AviB construct (FIG. 4E). Interestingly, although these three antibodies show similar overall binding affinities, Applicants measured a faster off-rate for PGDM1403 compared to PGT145 and PGDM1400. These differences in binding kinetics may play a role in differences observed in the neutralization of the BG505 isolate (32).

Broadly neutralizing antibodies are critical for revealing sites of vulnerability on HIV Env, especially in the context of vaccine design. Indeed, a finite number of these sites have been identified and it is becoming apparent that subtle differences in epitope recognition define an antibody's neutralization breadth and potency (33, 34, 35, 36). The results outlined here now present a clear example of fine epitope specificity for the trimer-apex glycan epitope with somatic variants deriving from a common ancestor that yield neutralizing antibodies with breadths that range from exceptional (PGDM1400, 83%) to very limited (PGDM1406, 6%). The neutralization properties of PGDM1400 and especially the combination of PGDM1400 with PGT121 also highlight its potential for delivery as a therapeutic antibody.

Applicants and others have shown positive correlations between the level of somatic hypermutation and neutralization breadth in a number of cases (2, 37, 38). Strikingly, in this case, there is little correlation between the breadth of antibody neutralization and the degree of somatic hypermutation (SHM) among the somatic variants described (FIG. 2 and FIG. 6). The two somatic variants PGDM1400 and PGDM1406, for example, show similar mutation levels from germline, but show demonstrably different neutralization profiles for breadth and potency. It would appear that they have undergone maturation along different pathways. The maturation of PGDM1400 towards great breadth of neutralization is understandable if the antibody is mutating in response to neutralization escape variants and maintains positive interactions with conserved regions while accommodating potentially obstructive variable regions (37), PGDM1406, on the other hand, likely diverged early from PGDM1400 during affinity maturation in response to escape and at some point responded to a particular virus in a way that lost breadth; this antigen must be distinct from classical HIV viral debris because PGDM1406 remains quaternary-specific. Indeed, such a loss of neutralization breadth over the course of infection has also been described previously in the evolution of trimer-apex bnAbs (2).

Overall, these results suggest that antibodies take something of a "random walk" in response to natural infection that can lead either to great breadth of neutralization pr to very limited neutralization. Guiding antibody evolution in the right direction through vaccination may be very difficult through simple mimicry of natural infection: one may need to take a more reductionist approach in which clearly defined stages along the maturation pathway are targeted through the design of specific immunogens and proceed along a more carefully planned route.

The antibodies described here represent the first time that a soluble trimeric Env molecule (BG505 SOSIP.664 gp140) has been used to select quaternary-specific antibodies. Strikingly, antigen sorting with BG505 SOSIP.664 gp140 appears more effective than B cell culturing methods both in recovering higher numbers of bnAbs and also in recovering bnAbs with greater potency. This difference is likely due to the limitations of each approach: antigen sorting is limited by affinity to antigen, while B cell culturing methods are limited by the capacity of memory B cells to secrete sufficient antibody concentrations for functional assays. Indeed, Applicants have seen wide variability in the expression levels of these somatic variants as recombinant antibodies. Low-expression antibodies would likely be missed during screening following B cell culturing methods. In contrast, these same somatic variants can be recovered by antigen sorting provided they have sufficient affinity for the BG505 SOSIP.664 gp140 antigen bait. In addition to isolating new bnAbs to the trimer apex, BG505 SOSIP.664 gp140 can potentially be used to isolate bnAbs targeting other quaternary epitopes (11, 12, 39). Indeed, quaternary epitopes have been described as a major response among elite neutralizers of various cohorts, but 30-50% of these responses are not confirmed to target the trimer apex (21, 40, 41). The isolation of new bnAbs to fully define old and new broadly neutralizing epitopes may continue to facilitate HIV vaccine design efforts.

Single-Cell Sorting by Flow Cytometry. Sorting was performed as described previously (6, 27). In brief, donor PBMCs were stained with primary fluorophore-conjugated antibodies to human CD3, CD8, CD14, CD19, CD20, CD27, IgG and IgM (BD Pharmigen) and 50 nM of BG505 SOSIP-AviB and 50 nM of JR-CSF gp120-AviB coupled to Streptavidin-PE and Streptavidin-APC (Life Technologies) in equimolar ratios, respectively. Staining was performed for 1 h at 4° C. in PBS with 1 mM EDTA and 1% FBS. In their gating strategy, Applicants first excluded unwanted cell populations (CD3−/CD8−/CD14−) followed by selection on BG505 SOSIP-Avi specific memory B cells (CD19+/CD20+/IgG+/IgM−/BG505 SOSIP.664+/JR-CSF gp120−). Cells of interest were single-cell sorted into 96 well plates containing lysis buffer on a BD FACSAria III sorter and immediately stored at −80° C. (6, 27).

Pseudovirus Production and Neutralization Assays. To produce pseudoviruses, plasmids encoding Env were co-transfected with an Env-deficient genomic backbone plasmid (pSG3ΔEnv) in a 1:2 ratio with the transfection reagent Fugene 6 (Promega). Pseudoviruses were harvested 72 h post transfection for use in neutralization assays. Neutralizing activity was assessed using a single round of replication pseudovirus assay and TZM-bl target cells, as described previously (3, 42). Kifunensine-treated pseudoviruses were produced by treating 293T cells with 25 μM kifunensine (TOSCO) on the day of transfection.

References For Example 1

1. Walker L M et al. (2009) Broad and potent neutralizing antibodies from an African donor reveal a new HIV-1 vaccine target. Science 326:285-289.

2. Doria-Rose N A et al. (2014) Developmental pathway for potent V1V2-directed HIV-neutralizing antibodies. Nature 509:55-62.

3. Walker L M et al. (2011) Broad neutralization coverage of HIV by multiple highly potent antibodies. Nature 477: 466-470.

4. Bonsignori M et al. (2011) Analysis of a clonal lineage of HIV-1 envelope V2/V3 conformational epitope-specific broadly neutralizing antibodies and their inferred unmutated common ancestors. J Virol 85:9998-10009.

5. Burton D R et al. (2012) A blueprint for HIV vaccine discovery. Cell Host Microbe 12:396-407.

6. Wu X et al. (2010) Rational design of envelope identifies broadly neutralizing human monoclonal antibodies to HIV-1. Science 329:856-861.

7. Huang J et al. (2012) Broad and potent neutralization of HIV-1 by a gp41-specific human antibody. Nature 491: 406-412.

8. Scheid J F et al. (2011) Sequence and structural convergence of broad and potent HIV antibodies that mimic CD4 binding. Science 333:1633-1637.

9. Mouquet H et al. (2012) Complex-type N-glycan recognition by potent broadly neutralizing HIV antibodies. Proc Natl Acad Sci USA 109:E3268-77.

10. Klein F et al. (2012) Broad neutralization by a combination of antibodies recognizing the CD4 binding site and a new conformational epitope on the HIV-1 envelope protein. J Exp Med 209:1469-1479.

11. Falkowska E et al. (2014) Broadly neutralizing HIV antibodies define a glycan-dependent epitope on the prefusion conformation of gp41 on cleaved envelope trimers. Immunity 40:657-668.

12. Blattner C et al. (2014) Structural delineation of a quaternary, cleavage-dependent epitope at the gp41-gp120 interface on intact HIV-1 Env trimers. Immunity 40:669-680.

13. Burton D R et al. (1994) Efficient neutralization of primary isolates of HIV-1 by a recombinant human monoclonal antibody. Science 266:1024-1027.

14. Muster T et al. (1994) Cross-neutralizing activity against divergent human immunodeficiency virus type 1 isolates induced by the gp41 sequence ELDKWAS. J Virol 68:4031-4034.

15. Burton D R et al. (1991) A large array of human monoclonal antibodies to type 1 human immunodeficiency virus from combinatorial libraries of asymptomatic seropositive individuals. Proc Natl Acad Sci USA 88:10134-10137.

16. Zwick M B et al. (2001) Broadly neutralizing antibodies targeted to the membrane-proximal external region of human immunodeficiency virus type 1 glycoprotein gp41. J Virol 75:10892-10905.

17. Barbas C F et al. (1992) Recombinant human Fab fragments neutralize human type 1 immunodeficiency virus in vitro. Proc Natl Acad Sci USA 89:9339-9343.

18. Trkola A et al. (1996) Human monoclonal antibody 2G12 defines a distinctive neutralization epitope on the gp120 glycoprotein of human immunodeficiency virus type 1. J Virol 70:1100-1108.

19. Conley A J et al. (1994) Neutralization of divergent human immunodeficiency virus type 1 variants and primary isolates by IAM-41-2F5, an anti-gp41 human monoclonal antibody. Proc Natl Acad Sci USA 91:3348-3352.

20. Buchacher A et al. (1994) Generation of human monoclonal antibodies against HIV-1 proteins; electrofusion and Epstein-Barr virus transformation for peripheral blood lymphocyte immortalization. AIDS Res Hum Retroviruses 10:359-369.

21. Simek M D et al. (2009) Human immunodeficiency virus type 1 elite neutralizers: individuals with broad and potent neutralizing activity identified by using a high-throughput neutralization assay together with an analytical selection algorithm. J Virol 83:7337-7348.

22. Gray E S et al. (2011) The neutralization breadth of HIV-1 develops incrementally over four years and is associated with CD4+ T cell decline and high viral load during acute infection. J Virol 85:4828-4840.

23. Wardemann H et al. (2003) Predominant autoantibody production by early human B cell precursors. Science 301: 1374-1377.

24. Scheid J F et al. (2009) Broad diversity of neutralizing antibodies isolated from memory B cells in HIV-infected individuals. Nature 458:636-640.

25. Gaebler C et al. (2013) Isolation of HIV-1-reactive antibodies using cell surface-expressed gp160Δc(BaL.). J Immunol Methods 397:47-54.

26. Sanders R W et al. (2013) A next-generation cleaved, soluble HIV-1 Env Trimer, BG505 SOSIP.664 gp140, expresses multiple epitopes for broadly neutralizing but not non-neutralizing antibodies. PLoS Pathog 9:e1003618.

27. Tiller T et al. (2008) Efficient generation of monoclonal antibodies from single human B cells by single cell RT-PCR and expression vector cloning. J Immunol Methods 329:112-124.

28. Zhu J et al. (2013) Mining the antibodyome for HIV-1-neutralizing antibodies with next-generation sequencing and phylogenetic pairing of heavy/light chains. Proc Natl Acad Sci USA 110:6470-6475.

29. McLellan J S et al. (2011) Structure of HIV-1 gp120 V1/V2 domain with broadly neutralizing antibody PG9. Nature 480:336-343.

30. Pancera M et al. (2013) Structural basis for diverse N-glycan recognition by HIV-1-neutralizing V1-V2-directed antibody PG16. Nat Struct Mol Biol 20:804-813.

31. Julien J-P et al. (2013) Asymmetric recognition of the HIV-1 trimer by broadly neutralizing antibody PG9. Proc Natl Acad Sci USA 110:4351-4356.

32. Yasmeen A et al. (2014) Differential binding of neutralizing and non-neutralizing antibodies to native-like soluble HIV-1 Env trimers, uncleaved Env proteins, and monomeric subunits. Retrovirology 11:41.

33. Lyumkis D et al. (2013) Cryo-EM structure of a fully glycosylated soluble cleaved HIV-1 envelope trimer. Science 342:1484-1490.

34. Tran K et al. (2014) Vaccine-elicited primate antibodies use a distinct approach to the HIV-1 primary receptor binding site informing vaccine redesign. Proc Natl Acad Sci USA 111:E738-47.

35. Kong L et al. (2013) Supersite of immune vulnerability on the glycosylated face of HIV-1 envelope glycoprotein gp120. Nat Struct Mol Biol 20:796-803.

36. Julien J-P et al. (2013) Crystal structure of a soluble cleaved HIV-1 envelope trimer. Science 342:1477-1483.

37. Sok D et al. (2013) The effects of somatic hypermutation on neutralization and binding in the PGT121 family of broadly neutralizing HIV antibodies. PLoS Pathog 9:e1003754.

38. Liao H-X et al. (2013) Co-evolution of a broadly neutralizing HIV-1 antibody and founder virus. Nature 496: 469-476.

39. Scharf L et al. (2014) Antibody 8ANC195 reveals a site of broad vulnerability on the HIV-1 envelope spike. Cell Rep 7:785-795.

40. Gray E S et al. (2007) Neutralizing antibody responses in acute human immunodeficiency virus type 1 subtype C infection. J Virol 81:6187-6196.

41. Walker L M et al. (2010) A limited number of antibody specificities mediate broad and potent serum neutralization in selected HIV-1 infected individuals. PLoS Pathog 6:e1001028.

42. Li M et al. (2005) Human immunodeficiency virus type 1 env clones from acute and early subtype B infections for standardized assessments of vaccine-elicited neutralizing antibodies. J Virol 79:10108-10125.

43. Sievers F et al. (2011) Fast, scalable generation of high-quality protein multiple sequence alignments using Clustal Omega. Mol Syst Biol 7:539.

44. Schrodinger, LLC (2010) The PyMOL Molecular Graphics System, Version 1.3r1.

45. Pettersen E F et al. (2004) UCSF Chimera—a visualization system for exploratory research and analysis. J Comput Chem 25:1605-1612.

Example 2

Supporting Information

Antibody Nomenclature. The previously isolated PGT antibodies from the Protocol G cohort were isolated through Theraclone screening, and thus were named "PGT." To distinguish between antibodies isolated from Theraclone (by B-cell culture) and antibodies isolated by investigators of this study (by antigen selection), Applicants have named the newly isolated variants "PGDM." Applicants start the series with "14" to indicate that they are related to the PGT140 series, but Applicants have added an extra digit to the end of the name because Applicants have >10 antibodies. The somatic variants therefore are named PGDM1400-1412.

Human Specimens. PBMCs were obtained from donor 84, an HIV-1-infected donor from the IAVI Protocol G cohort (1). All human samples were collected with written informed consent under clinical protocols approved by the Republic of Rwanda National Ethics Committee, the Emory University Institutional Review Board, the University of Zambia Research Ethics Committee, the Charing Cross Research Ethics Committee, the Uganda Virus Research Institute Science and Ethics Committee, the University of New South Wales Research Ethics Committee, St. Vincent's Hospital and Eastern Sydney Area Health Service, Kenyatta National Hospital Ethics and Research Committee, University of Cape Town Research Ethics Committee, the International Institutional Review Board, the Mahidol University Ethics Committee, the Walter Reed Army Institute of Research Institutional Review Board, and the Ivory Coast Comité National d'Éthique des Sciences de la Vie et de la Santé.

Data and Materials Availability. Gene sequences of the reported antibodies have been deposited in GenBank under the accession numbers KP006370-KP006382 for heavy-chain sequences and KP006383-KP006395 for kappa-chain sequences.

Construct Design. For this study, a variant of the recombinant envelope protein BG505 SOSIP.664 gp140 trimer (2) bearing an avi tag at the C terminus of the gp41 ectodomain (gp41ECTO) was made by adding the amino acid sequence GSGLNDIFEAQKIEWHE (SEQ ID NO: 27) after residue 664 in gp41ECTO and preceding the stop codon. This protein is designated "SOSIP.664-Avi gp140." A monomeric BG505 gp120 with a sequence identical to the gp120 components of the gp140 trimer also was constructed with an avi tag, designated "BG505-avi" and includes the L111A substitution to decrease gp120 dimer formation (3, 4). BG505 SOSIP.664 containing a polyhistidine tag (BG505 SOSIP.664-His gp140) was used as described previously (2).

Recombinant Env Trimer Expression. The recombinant envelope proteins BG505 SOSIP.664-avi gp140, BG505 SOSIP.664-His gp140, and BG505-avi gp120 were expressed in HEK293F cells (Invitrogen) as described previously (2). Briefly, HEK293F cells were maintained in FreeStyle medium (Invitrogen). For gp140 trimer production, HEK293F cells were seeded at a density of $0.5\times10^6$/mL. After 24 h, cells were transfected with 1 mg of 293Fectin (Invitrogen) with 300 μg of Env plasmid and 75 μg of furin plasmid in Opti-MEM (Life Technologies) according to the manufacturer's protocol. Kifunensine-treated proteins were produced by adding kifunensine (Tocris) to HEK293F cells at a final concentration of 25 μM on the day of transfection. Cultur supernatants were harvested 6-7 d after transfection. SDS/PAGE and Blue Native-PAGE were performed as described previously (2).

Recombinant Env Trimer Purification. BG505 SOSIP.664-avi gp140 and BG505 SOSIP.664-His gp140 were purified by affinity chromatography using a 2G12 column as described previously (2). BG505-avi gp120 proteins were purified using a Galanthus nivalis lectin (Vector Labs) column (2). Briefly, transfection supernatants were vacuum-filtered through 0.2-μm filters and then passed over the column at a 0.5-1 mL/min flow rate. The 2G12 column was made from cyanogen bromide-activated Sepharose 4B beads (GE Healthcare) coupled to the bnAb 2G12 (Polymun Sciences). Purification using this column was performed as follows: The beads were washed with two column volumes of buffer [0.5 M NaCl, 20 mM Tris (pH 8.0)] before eluting bound Env proteins using one column volume of 3 M $MgCl_2$ into one column volume of 75 mM NaCl, 10 mM Tris (pH 8.0). The eluted Env proteins were concentrated using Vivaspin columns with a 100-kDa cut off (GE Healthcare). The affinity-purified Env proteins were purified further to size homogeneity using size exclusion chromatography on a Superose 6 10/300 GL column (GE Healthcare) in PBS. The trimer fractions were collected and pooled, and protein concentrations were determined using either a bicinchonic acid-based assay (Thermo Scientific) or UV280 absorbance using theoretical extinction coefficients (5). The Env proteins were biotinylated in vitro using the BirA enzyme (Aviditiy) according to the manufacturer's protocol.

ELISA for Monomeric and Trimeric BG505 Env Proteins. ELISAs were performed as described previously (2) with minor modifications. Microlon 96-well plates (Corning) were coated overnight with streptavidin (Thermo Scientific), anti-biotin antibody (Roche), or anti-His antibody (Thermo Scientific) at 2.5 μg/mL in PBS (50 μt, per well). After washing and blocking with 3% BSA for 1 h at room temperature, biotinylated BG505 SOSIP.664-Avi gp140, BG505 SOSIP.664-His gp140, or BG505-avi gp120 proteins were added at 1 μg/mL in PBS/1% BSA for 2 h at 37° C. Unbound Env proteins were washed away, and serially diluted mAbs in PBS/1% BSA then were added for 2 h at room temperature. Unbound mAbs were washed away, and alkaline phosphataselabeled goat anti-human IgG (Jackson ImmunoResearch) was added for 1 h at a 1:1,000 dilution (final concentration 0.33 μg/mL) in PBS/1% BSA at room temperature. After washing, absorption was measured at 405 nm. For binding to gp120 extracted from lysed virions, plates were coated with 5 ng/uL of sheep D7324 anti-gp120 antibody (Aalto Bioreagents). Virus supernatants were lysed using a final concentration of 1% Nonidet P-40 and incubated on coated plates for 2 h at 37° C. Detection was measured using goat anti-human IgG $F(ab')_2$ conjugated to alkaline phosphatase (Pierce). Antibody concentration was calculated by linear regression using a standard concentration curve of purified IgG protein.

Competition ELISA. For competition ELISA experiments, competing antibodies were biotinylated using an antibody biotinylation kit (Thermo Scientific). Plates were coated with an anti-His antibody (Roche) at 5 μg/mL overnight. After washing, plates were blocked with 3% BSA for 1 h at room temperature. BG505 SOSIP.664-His gp120 then was captured at 2.5 μg/mL in PBS (50 μL per well) for 2 h at 37° C. After washing, serially diluted antibodies in PBS/1% BSA were added for 30 min. The biotinylated antibody was added at a constant EC70 concentration for 1 h. Plates were washed, and detection was measured using alkaline phosphatase-conjugated streptavidin (Pierce) at 1:1,000 for 1 h at room temperature. Absorption was measured at 405 nm.

Flow Cytometry Staining of WEHI B-Cell Lines. Previously described mouse B-cell WEHI cell lines (6), which express cell-surface bnAbs, were used in flow cytometric binding assays to evaluate the antigenicity of BG505 SOSIP-AviB trimers. The bnAb expressing cells were induced by overnight incubation with doxycycline (1 μg/mL) as described previously (6). Cells ($1\times10^6$) were stained simultaneously with 50 nM of BG505 SOSIP-AviB conjugated to streptavidin-PE (Invitrogen) and 50 nM of JRCSF gp120-AviB conjugated to streptavidin-APC (Invitrogen). Staining was performed in a final volume of 100 μL at 4° C. in 1×PBS with 1 mM EDTA and 1% FBS, before washing and was analyzed on a BD LSR II FACS machine.

Single B-Cell RT-PCR, Gene Amplification, and Cloning.

Reverse transcription and subsequent PCR amplification of heavy- and light-chain variable genes were performed according to previous protocols (7, 8). All PCR reactions were performed in a 25-μL volume with 2.5 μL of cDNA transcript using HotStar Taq DNA polymerase master mix (Qiagen). Previous primer mixes were supplemented with additional specific VH1-8 primers and VK2-28 primers: heavy-chain PCR 1 (ATGGACTGGATTTGGAGGAT) (SEQ ID NO: 28), heavy-chain PCR 2 (ATGGACTGGATTTGGAGGATCCTCTTCTTGG) (SEQ ID NO: 29), kappa-chain PCR 1 (ATGAGGCTCCCTGCTGCCATCCTGGGGCTGCTAATGC) (SEQ ID NO: 30), and kappa-chain PCR 2 (GCTCCTGGGGCTGCTAATGCTCTGGGTCTCTGG) (SEQ ID NO: 31). Amplified IgG heavy- and light-chain variable regions were sequenced and analyzed using the international ImMunoGeneTics information system (IMGT) V-quest webserver (www.IMGT.org) (9). Wells for which heavy-chain (VH1-8 gene) and light-chain (VK2-28) sequences were deemed productive rearrangements by IMGT analysis were selected for cloning into corresponding Igγ1, Igκ, and Igλ expression vectors as previously described (7).

Antibody Production. Heavy- and light-chain plasmids were cotransfected (1:1 ratio) in either HEK 293T or 293 FreeStyle cells using Fugene 6 (Promega) or 293fectin (Invitrogen), respectively. Transfections were performed according to the manufacturer's protocol, and antibody supernatants were harvested 4 d after transfection. Antibodies produced in 293T cells were quantified by ELISA and used directly in neutralization assays. Antibodies produced in 293 freestyle cells were purified over a protein A column as described previously (10).

Cell Surface-Binding Assays. Titrating amounts of mAbs were added to HIV-1 Env-transfected 293T cells and were incubated for 1 h at 4° C. in 1×PBS. After washing, cells were fixed with 2% paraformaldehyde (PolySciences) for 20 min at room temperature. The cells then were washed and stained with a 1:200 dilution of PE-conjugated goat anti-human IgG $F(ab')_2$ (Jackson) for 1 h at room temperature. Binding was analyzed using flow cytometry. Binding competitions were performed by titrating amounts of competitor mAbs before adding biotinylated antibody at the concentration required to achieve $IC_{70}$ and then measuring binding with PE-labeled streptavidin (Invitrogen). FlowJo software was used for data interpretation.

Autoreactivity Assays. Antibodies were assayed at 100 μg/mL for autoreactivity to HEp-2 cells (Aesku Diagnostics) by immunofluorescence according to the manufacturer's instructions. Briefly, 2.5 μg or 25 μL of 100 μg/mL mAb was incubated on HEP-2 slides in a moist chamber at room temperature for 30 min. The slides then were placed in staining dishes and washed with PBS. FITC-conjugated goat anti-human IgG (20 μL) was applied to each well, and slides were incubated for another 30 min. After washing, slides were photographed on an EVOS fl fluorescence microscope at a 250-ms exposure with 70% intensity. Reactivity to HIV-1-human epithelial HEp-2 cells was interpreted by the staining patterns. Positive and negative control sera were provided by the vendor. ELISAs were performed as described previously (11). Briefly, human placental dsDNA (Sigma) and ganglioside GD1a (Sigma) in 96% ethanol were coated at 37° C. overnight onto ELISA wells. BSA (Sigma), ovalbumin (Sigma), apo transferrin, and histone (Sigma) were resuspended in PBS and coated overnight at 4° C. All antigens were coated at 50 ng per well. Then the wells were washed and blocked for 1 h at room temperature with 3% BSA. Serial dilutions of antibodies were added for 1 h at room temperature. After washing, bound antibody was detected by using an alkaline phosphatase-conjugated goat anti-human IgG $F(ab')_2$ antibody (Pierce) diluted 1:1,000 in 1% BSA/PBS.

Octet Measurements. Binding curves were determined by bio-layer interferometry using an Octet RED instrument (ForteBio, Inc.) as previously described (12, 13). Briefly, IgG antibodies were immobilized onto anti-human IgG Fc biosensors. Varying concentrations of BG505-SOSIP.664-AviB were flowed as analyte in solution. Binding-affinity constants ($K_D$; on-rate, $k_a$; off-rate, $k_d$) were determined using Octet Analysis version 7 software (ForteBio; Pall Life Sciences).

Determination of PGDM1400 Fab Crystal Structure. Expression and purification of the PGDM1400 Fab was executed following a protocol similar to that previously described (14). Briefly, the Fab was produced by cotransfection of the heavy- and light-chain genes into HEK 293F cells. Six days after transfection, the supernatant was recovered and flowed over an anti-human kappa light-chain affinity matrix (CaptureSelect Fab κ; BAC). The eluted fraction containing the Fab was purified further by MonoS cation exchange chromatography (GE Healthcare). PGDM1400 Fab at a concentration of 6 mg/mL in 20 mM sodium acetate (pH 5.6) was crystallized from nonbuffered mother liquor containing 0.04 M potassium dihydrogen phosphate, 16% (wt/vol) polyethylene glycol 8000, and 20% (vol/vol) glycerol. Crystals were flash cooled in liquid nitrogen, and data were collected at the Stanford Synchrotron Radiation Lightsource (SSRL) beamline 11-1. Statistics for data collection and data processing in XDS (15) are summarized in Table 1. The monoclinic space group P21 and the structure was solved by molecular replacement using the program Phaser (16) with the PGT145 Fab structure (PDB ID code 3U1S) as a search model. Refinement of three Fab copies in the asymmetric unit was performed using a combination of Phenix (17) and Coot (18). Final refinement statistics are reported in Table 1.

Electron Microscopy. Sample grids were prepared as described previously (19). Data were collected on an FEI Tecnai T12 electron microscope operating at 120 keV coupled with a 4×4 k Tietz TemCam-F416 camera. Images were taken using the LEGINON interface (20). The imaging magnification was 52,000× with a pixel size of 2.05 Å at the specimen plane. The data were collected using an electron dose of ~30 e-/Å2. Particles were picked using DoG picker in the Appion interface (21, 22), and class averages were generated using the SPARX software package (23).

TABLE 1

Primers_(SEQ ID NOS 32-39, respectively, in order of appearance) used for amplification of variable heavy- and light-chain genes

| Nested PCR reaction | 5' to 3' sequence |
|---|---|
| Heavy chain ($V_H$1-8) | |
| PCR 1 Forward | ATGGACTGGATTTGGAGGAT |
| PCR 1 Reverse | GGAAGGTGTGCACGCCGCTGGTC |
| PCR 2 Forward | ATGGACTGGATTTGGAGGATCCTCTTCT TGG |
| PCR 2 Reverse | GTTCGGGGAAGTAGTCCTTGAC |
| Light chain ($V_\kappa$2-28) | |
| PCR 1 Forward | ATGAGGCTCCCTGCTCAGCTCCTGGGGC TGCTAATGC |
| PCR 1 Reverse | GTTTCTCGTAGTCTGCTTTGCTCA |
| PCR 2 Forward | GCTCCTGGGGCTGCTAATGCTCTGGGTC TCTGG |
| PCR 2 Reverse | GTGCTGTCCTTGCTGTCCTGCT |

TABLE 2

Data collection and refinement statistics for SSRL 11-1

| Data collection | |
|---|---|
| Wavelength, Å | 0.97947 |
| Space group | $P2_1$ |
| Unit cell a, b, c, Å | 55.7, 149.2, 109.9 |
| α, β, γ, ° | 90, 100.9, 90 |
| Resolution (Å)* | 40-3.1 (3.2-3.1) |

TABLE 2-continued

Data collection and refinement statistics for SSRL 11-1

| | |
|---|---|
| Completeness* | 96.7 (98.6) |
| Redundancy* | 3.4 (3.5) |
| No. total reflections | 108,438 |
| No. unique reflections | 30,950 |
| I/σ* | 6.8 (1.7) |
| $R_{merge}$*,† | 16.7 (58.4) |
| $R_{pim}$*,‡ | 10.4 (35.7) |
| $CC_{1/2}$*,§ | 97.4 (50.1) |
| Refinement statistics | |
| Resolution, Å | 40-3.1 |
| No. reflections total/$R_{free}$ | 30,926/1,544 |
| $R_{cryst}$¶/$R_{free}$‖ | 22.1/25.3 |
| Rmsd bond length, Å | 0.003 |
| Rmsd bond angles, ° | 0.8 |
| Protein atoms | 10,427 |
| Wilson B-value, $Å^2$ | 57.7 |
| B-value overall, $Å^2$ | 61.5 |
| Ramachandran favored, % | 95.4 |
| Ramachandran allowed, % | 99.9 |
| Molprobity all-atom clashscore | 7.8 |
| PDB ID code | 4RQQ |

*Values in parentheses are for the highest resolution shell.

†Rmerge = Σ|I − <I>|/Σ<I>, where I is the observed intensity, and <I> is the average intensity of multiple observations of related relections.

‡$R_{pim}$ = Σhkl (1/(n − 1))½ Σi | Ihkl, i − <Ihkl> |/Σhkl Σi Ihkl, I, where Ihkl, i is the scaled intensity of the $i^{th}$ measurement of reflection h, k, l, <Ihkl > is the average intensity for that reflection, and n is the redundancy.

§$CC_{1/2}$ = correlation coefficient of half-datasets (1).

¶$R_{cryst}$ = Σhkl||Fobs| − |Fcalc||/Σhkl|Fobs|.

‖$R_{free}$ calculated as for $R_{cryst}$ but for 5% of the reflections excluded from refinement.

(1) Karplus P A, Diederichs K (2012) Linking crystallographic model and data quality. Science 336(6084): 1030-1033.

References For Example 2

1. Simek M D, et al. (2009) Human immunodeficiency virus type 1 elite neutralizers: Individuals with broad and potent neutralizing activity identified by using a high throughput neutralization assay together with an analytical selection algorithm. J Virol 83(14):7337-7348.

2. Sanders R W, et al. (2013) A next-generation cleaved, soluble HIV-1 Env Trimer, BG505 SOSIP.664 gp140, expresses multiple epitopes for broadly neutralizing but not non neutralizing antibodies. PLoS Pathog 9(9): e1003618.

3. Hoffenberg S, et al. (2013) Identification of an HIV-1 clade A envelope that exhibits broad antigenicity and neutralization sensitivity and elicits antibodies targeting three distinct epitopes. J Virol 87(10):5372-5383.

4. Finzi A, et al. (2010) Conformational characterization of aberrant disulfide-linked HIV-1 gp120 dimers secreted from overexpressing cells. J Virol Methods 168(1-2):155-161.

5. Gasteiger J (2006) Chemoinformatics: A new field with a long tradition. Anal Bioanal Chem 384(1):57-64.

6. Ota T, et al. (2012) Anti-HIV B Cell lines as candidate vaccine biosensors. J Immunol 189(10):4816-4824.

7. Wu X, et al. (2010) Rational design of envelope identifies broadly neutralizing human monoclonal antibodies to HIV-1. Science 329(5993):856-861.

8. Tiller T, et al. (2008) Efficient generation of monoclonal antibodies from single human B cells by single cell RT-PCR and expression vector cloning. J Immunol Methods 329(1-2):112-124.

9. Lefranc M-P, et al. (2009) IMGT, the international ImMunoGeneTics information system. Nucleic Acids Res 37(Database issue):D1006-D1012.

10. Sok D, et al. (2013) The effects of somatic hypermutation on neutralization and binding in the PGT121 family of broadly neutralizing HIV antibodies. PLoS Pathog 9(11): e1003754.

11. Walker L M, et al.; Protocol G Principal Investigators (2009) Broad and potent neutralizing antibodies from an African donor reveal a new HIV-1 vaccine target. Science 326(5950):285-289.

12. Ekiert D C, et al. (2011) A highly conserved neutralizing epitope on group 2 influenza A viruses. Science 333(6044):843-850.

13. Tran K, et al. (2014) Vaccine-elicited primate antibodies use a distinct approach to the HIV-1 primary receptor binding site informing vaccine redesign. Proc Natl Acad Sci USA 111(7):E738-E747.

14. Pejchal R, et al. (2010) Structure and function of broadly reactive antibody PG16 reveal an H3 subdomain that mediates potent neutralization of HIV-1. Proc Natl Acad Sci USA 107(25):11483-11488.

15. Kabsch W (2010) Xds. Acta Crystallogr D Biol Crystallogr 66(Pt 2):125-132.

16. McCoy A J, et al. (2007) Phaser crystallographic software. J Appl Cryst 40(Pt 4):658-674.

17. Adams P D, et al. (2010) PHENIX: A comprehensive Python-based system for macromolecular structure solution. Acta Crystallogr D Biol Crystallogr 66(Pt 2):213-221.

18. Emsley P, Cowtan K (2004) Coot: Model-building tools for molecular graphics. Acta Crystallogr D Biol Crystallogr 60(Pt 12 Pt 1):2126-2132.

19. Julien J-P, et al. (2013) Asymmetric recognition of the HIV-1 trimer by broadly neutralizing antibody PG9. Proc Natl Acad Sci USA 110(11):4351-4356.

20. Suloway C, et al. (2005) Automated molecular microscopy: The new Leginon system. J Struct Biol 151(1): 41-60.

21. Voss N R, Yoshioka C K, Radermacher M, Potter C S, Carragher B (2009) DoG Picker and TiltPicker: Software tools to facilitate particle selection in single particle electron microscopy. J Struct Biol 166(2):205-213.

22. Lander G C, et al. (2009) Appion: An integrated, database-driven pipeline to facilitate EM image processing. J Struct Biol 166(1):95-102.

23. Hohn M, et al. (2007) SPARX, a new environment for Cryo-EM image processing. J Struct Biol 157(1):47-55.

The invention is further described by the following numbered paragraphs:

1. An isolated fully human anti-HIV-1 monoclonal antibody, designated PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412, comprising a heavy chain sequence and a light chain sequence, each corresponding to PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412.

2. The isolated fully human anti-HIV-1 monoclonal antibody of paragraph 1, wherein the antibody is PGDM 1400.

3. A composition comprising the antibody of paragraph 1 or 2.

4. A pharmaceutical composition comprising the antibody of paragraph 1 or 2 and a pharmaceutically acceptable carrier.

5. A method of inhibiting HIV in a host comprising administering to the host an antibody as in paragraphs 1 or 2, or a composition as in paragraphs 3 or 4.

6. An expression vector that encodes and stably expresses in vivo an antibody comprising each of a heavy chain sequence of PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412 and a light chain sequence of PGDM 1400, PGDM 1401, PGDM 1402, PGDM 1403, PGDM 1404, PGDM 1405, PGDM 1406, PGDM 1407, PGDM 1408, PGDM 1409, PGDM 1410, PGDM 1411 or PGDM 1412.

7. The expression vector of paragraph 6 wherein the vector contains and expresses in vivo an antibody comprising a heavy chain sequence of PGDM 1400 and a light chain sequence of PGDM 1400.

8. A composition comprising the expression vector of paragraph 6 or 7.

9. A pharmaceutical composition comprising the expression vector of paragraph 6 or 7 and a pharmaceutically acceptable carrier.

10. The expression vector of paragraph 6 or 7 wherein the expression vector comprises a viral based vector.

11. The composition of paragraph 10 wherein the vector is viral based.

12. The pharmaceutical composition of paragraph 9 wherein the vector is viral based.

13. The vector, composition or pharmaceutical composition of paragraph 10, 11 or 12, wherein the virus is an adeno-associated virus (AAV).

14. A method of inhibiting HIV in a host comprising administering to the host the expression vector as in paragraph 6, 7, 10, 12 or 13 under conditions whereby the vector expresses the antibody.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

SEQUENCE LISTING

```
<160> NUMBER OF SEQ ID NOS: 75

<210> SEQ ID NO 1
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

caggtgcatc tgacgcagtc tgggcctgag gtgaggaagc ctgggacctc cgtaaaggtc      60

tcctgcaagg cccctggaaa cacattgaag acttatgatc tacactgggt gcgcagcgtc     120
```

```
cctggacaag gccttcagtg gatgggatgg ataagccatg agggcgacaa gaaggtcatt    180

gtggaaagat tcaaggccaa agtcaccatt gattgggaca ggtccaccaa tacggcctat    240

ctccaactga gcggcctcac atctggcgac acggccgtct attattgtgc gaaaggctca    300

aaacacaggc tgcgagatta cgctctctac gacgacgacg gcgcattgaa ttgggctgtc    360

gatgttgact acctttcgaa cttggaattc tggggccaag ggaccgccgt caccgtctct    420

tca                                                                  423


<210> SEQ ID NO 2
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

caggcgcaac tggtgcagtc tgggcctgag atgaggaaac ctggggcctc cgtaaaggtc     60

tcctgcaagg cccctggaaa tacattgaag aatcatgatc tacactgggt gcgcaacgtc    120

cctggacagg ggcttgagtg ggtggggtgg gtgagtcacg agggcgacaa aaaggtcatt    180

gtagagaaat tcaaggccag cgtcaccatt gattgggaca ggtccctgaa tacggcctat    240

cttcaactgc gcggcctcag gtctgaagac acggccgtct attattgtgc gagagggtca    300

aaacacaggc tgcgagacta cgttatgtac gacgactacg gcgcattgca gtgggctgtc    360

tatgttgact atctttcgaa cttggacgtc tggggccaag ggaccgccgt caccgtctct    420

cca                                                                  423


<210> SEQ ID NO 3
<211> LENGTH: 423
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

caggtgcaac tggcgcagtc tgggcctgag gtgaggaagc ctggggcctc cgtaaaggtc     60

tcctgcaagg cccctggaaa tacattgaag acttatgatc tacactgggt gcgagacgtc    120

cctggacagg gcctgcagtg gatgggatgg gtgagccacg agggcgacaa gaaggtcatt    180

gtggagagat tcaaggccaa agtcagcatt gattgggaca ggtccacaaa tacggcctat    240

ctacaactga gcggcctcac atctgaagac acggccgtct attattgtgc gaaaggctca    300

aaacacaggc tgcgagacta cgctctgtac gacgacatcg gcgcattgca atgggctgtc    360

gatgttgact acctttcgac cttggaattt tggggccaag ggaccgccgt caccgtctct    420

tca                                                                  423


<210> SEQ ID NO 4
<211> LENGTH: 420
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

gaggtgcttc tggagcagtc cgggggtgaa gtgaagcagc ctggggcctc agtgaagatc     60
```

tcctgcaaag cctctggatt caattttaac aatgaagatg tgcactgggt gcgacaggcc 120 gctggacaag gtctggagtg gatggcatgg tcgaaacatg acgatcaaaa tgttttgtat 180 gcacaagaat ttaaggacag ggtcaccgtg acgagggaca ccgccgcaaa tacagtctac 240 attcagatga ccggtctgag atttgaagac acggccctct attattgtgt taagggctca 300 aagtttaggc tgagggagtg ggctgattac aatgaatggg gcctagtttc ggctcaacat 360 ggagactacg tgacgcagtt gggcatctgg ggccagggga ccgcgatcta cgtctcgtca 420

<210> SEQ ID NO 5
<211> LENGTH: 423
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 5 caggtgtttt tggaacagtc tgggggtgag gtgaggaggc ctggggcctc agtgaaggtc 60 tcctgcaagg ccactggatt caccttccgt aatgatgatg ttcactgggt gcgacaggcc 120 actggccaag ggcctgagtg cgtggcttgg atgaagcatg acgatcaaag tacagtcttt 180 ccaaagaagt tccagggcag agtcatcgtg acaacggaca cctccgcaac aacagtctac 240 atggagatgg ggggcctgat gcctgaagac acggccattt attactgtgt aagaggcgca 300 aaatttcggt tgagacatga cgccacttat gattactgga acgacttact ttgggctgac 360 gaccgtgact acgtgacgca gttagacctt tggggcccag ggaccgctat cattgtctcc 420 gca 423

<210> SEQ ID NO 6
<211> LENGTH: 423
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 6 caggtgtttt tggaacaatc tgggggtgaa ataaagaggc ctggggcctc agtgaaggtc 60 tcctgcaagg ccactggatt caccttccat cacgatgatg ttcactgggt gcgacaggcc 120 actggccaag ggcctgagtg cgtggcttgg atgaaacatg acgatcaaag tacagtctat 180 ccacagaagt tccagggcag agtcaccgtg acaagcgaca cctccggtac aacagtctat 240 atggagatgg ggggactgat gcctgaagac acggccattt attactgtgt cagaggcgca 300 aagttcaggt tgagacatga cgcaacatat gattactaca atgacttgct ttgggctgac 360 gaccgtgact acgtgacgca gttggacctt tggggccaag ggaccgcgat catcgtctcc 420 gca 423

<210> SEQ ID NO 7
<211> LENGTH: 420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 7 caagtccagg tggaccagtc cgggggtgag gtgaagaagc ctggggcctc agtgagggtc 60 tcctgcaagg cctcgggatt ctcttttaag agtgaagata tgcactgggt gcgacaggcc 120 gctggacgag ggctggagtg gatggcatgg gtaaaacatg acagtgatga aatattatat 180 tcagaaaagt ttaaggacag ggtcatcgtg accaggaaca ccgcctcaaa cacaatctcc 240 atggacatga ccggtctgac atctgaagac acggcccgat attattgtgt gaaaggccaa 300 aagttcaggc tgacagagtg ggctgactac aatgaattcg gcctagtggc ggctcaaaaa 360 ggagactacg tgacacagct ggacgtctgg ggccagggga ccgacatcat cgtctcgtca 420

<210> SEQ ID NO 8
<211> LENGTH: 420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 8 caagtcaagt tggaccagtc cgggggtgag gtgaagaagc ctggggcctc agtgacggtc 60 tcctgcaagg cctctggatt tagttttgga agtgaagatg tacactgggt gcgacaggcc 120 gctaggggag ggctggactg gatggcatgg gtgaaacatg acagtcatga aattttatac 180 gcacagaaat ttaagggcag ggtcaccgtg accaggaaca ccgcctcaaa cacagtcttc 240 atggagatga ccggtctgac atctgaagac acggcccgat attattgtgt gaaaggtcaa 300 aagtttcggc tgacagagtg ggctgactat aatgaattcg gcctggtggc ggctgaaaaa 360 ggagactacg tgacacaact ggacgtctgg ggccagggga ccgcgatcat cgtctcgtca 420

<210> SEQ ID NO 9
<211> LENGTH: 423
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 9 caggcgcaac tggtacagtc tgggcctgag atgaggagtc ctggggcctc cgtaaaggtc 60 tcctgcaagg cccctggaaa tacattgaag aatcatgatc tacactgggt gcgcaacgtc 120 cctggacagg ggcttgagtg ggtggggtgg gtgagtcacg agggcgacaa aaacgtcatt 180 atagagaaat tcaaggccag agtcaccatt gattgggaca ggtccctgaa tacggcctat 240 ctgcaactgc gcggcctcag gtctgaggac acggccgtct attattgtgc gagagggtca 300 aaacacaagc tgcgagacta cgttatgtac gacgactatg gcgcattgca gtgggctgtt 360 tatgttgact atctttcgaa cttggacgtc tggggccagg ggaccgccgt caccgtctct 420 cca 423

<210> SEQ ID NO 10
<211> LENGTH: 422
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 10 caggtgtttt tggaacaatc tgggggtgaa gtaaagaggc ctggggcctc agtgaaggtc 60 tcctgcaagg ccactggatt caccttccgt caaaatgatg ttcactgggt gcgacaggcc 120 actggccaag ggcctgagtg cgtggcttgg atgaaacatg acgatcaaag tacagtcctt 180 ccacagaagt tccagggcag agtcaccgtg acaagcgaca cctccgctac aacagtctat 240 atggagatgg ggggactgat gcctgaagac acggccattt attactgtgt cagaggcgca 300 aagttcaggt tgagacatga cgcaacatat gattactgga atgacttgct ttgggctgac 360 gaccgtgact acgtgacgca gttggacctt tggggccaag ggaccgcgat catcgtctcc 420 gc 422

<210> SEQ ID NO 11
<211> LENGTH: 423
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 11 caggtgtttt tggagcagtc tgggggtgag gtgaggaggc ctggggcctc agtaaacgtc 60 tcctgcaagg ccactggatt caccttccat catcatgatg ttcattgggt gcgacaggcc 120 actggccaag ggcctgagtg tgtggcgtgg atgaaacatg acgatcaaag tacagtcttt 180 ccacagaagt tccagggcag agtcaccgtg acaagggaca cctccgctaa aatagtttat 240 atgcagatgg ggggactgat gcctgaagac acggccatat attattgtgt gagaggctca 300 aaatttaggt tgagaaatga cgctatctac gattattgga acgacttact ttgggctgac 360 gacggtgact acgtgacgaa gttggacctt tggggccatg ggaccgcgat catcgtctcc 420 tca 423

<210> SEQ ID NO 12
<211> LENGTH: 420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 12 caggtgcaat tggtgcagtc tggagccgag gtgaggaagc ctgggacctc agtgaaaatc 60 tcctgcacga cctctggata ttctttcaac agtcatcata tccactgggt gcgacacggc 120 accggacaag gacttgagtg gattgggtgg gtggacccaa ataatggtaa tacaggatat 180 acaccaaaat tcaaggacag agtcaccttt gtcaagaata cctccacaca gacggtgttc 240 atggaagtga ccagtctaaa atctgaggac acgggcgtct attattgtgc gagacggaca 300 gaaaaacaac tgagagcaga gtatgttctg gaccaagaag acggctttta tcgtgaagag 360 gccatttaca tcacagtcct ggacgtctgg ggccaaggga ccgcggtcgc cgtctcctca 420

<210> SEQ ID NO 13
<211> LENGTH: 420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 13 caggtacatc tggagcagtc cgggggtgag gtgaagaagc ctggggcgtc ggtgaaggtc 60 tcctgcaagg cctctggatt cacttttagt agtgatgata tgcactgggt gcgacaggcc 120 gctggacaag ggctggagtg gatgtcatgg gtgaaacatg acagtcatga aatattggtt 180 ggacaaaagt ttaaggaccg ggtcatcgtg accaggaaca ccgccgcaaa cacagtctac 240 ttggaaatga ccggtctgag atctgaagac acggccacat attattgtgt aaaaggtcta 300 aaatttaggc tgagagagtg gtcagactat aatgaattcg gcctagtggc ggctcaacat 360 ggagactacg tgacacaaat ggaggtctgg ggccagggga ccgcgatcag cgtctcctca 420

<210> SEQ ID NO 14
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 14 gattttgtcc tgactcagtc tccacactct ctgtccgtca cccctggaga gtcggcctcc 60 atctcctgca agtctagtca cagcctcatt catggtgata ggaacaatta tttggcttgg 120 tacgtacaga agccagggcg gtctccacaa ctcctgatct atttggcttc cagtcgggcc 180 tccggggtcc ctgacaggtt cagtggcagt ggatcggaca aagattttac actgaagatc 240 agcagagtgg agactgagga tgttgggacg tattactgca tgcaaggtcg agaaagtccc 300 tggacgttcg gccaagggac caaggtggac atcaaa 336

<210> SEQ ID NO 15
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 15 gattttgtcc tgactcagtc tccacactct ctatccgtca ccccgggaga gccggcctcc 60 atctcctgca ggtctagtca gagcctcctt catggtgata aaaacaacta tttggcttgg 120 tatctccaga agccagggca ctctccacaa ctgctgatct atatggcttc tagtcggccc 180 tcaggggtcc ctgacaggtt cagtggcagt ggctcgggca cacattttac actgaaaatc 240 agtagagtgg agactgaaga tgttgggatg tactactgca tgcaaggtcg agaaagtccc 300 tggacgtttg gccaagggac caaggtggaa atcaaa 336

<210> SEQ ID NO 16
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 16 gactttgtcc tgactcagtc tccacactct ctgtccgtca cccctggaga gccggcctcc 60 atctcctgca agtctagtca cagcctcatt catggtgata agaacaacta tttggcttgg 120 tacgttcaga agccagggcg gtctccacaa ctcctgatct atttggcttc cagtcgggcc 180 tccggggtcc ctgacaggtt cagtggcagt ggatcggaca aagattttac actgaagatc 240 agcagagtgg agactgagga tgttgggacc tattactgca tgcaaggtcg agaaagtccc 300 tggacgttcg gccaggggac caaggtggaa atcaaa 336

<210> SEQ ID NO 17
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 17 aaaattgcgt tgactcagtc tccactctcc ctggccgtca cccctggaga gccggcctcc 60 atttcctgca ggtcaagtca gagcctcctt tataagaatg aacacaatga tgcatatatc 120 gaatatacct tcttgagttg gtatctgcag aggccaggcc agtctccaca actcctgatc 180 tatttgggtt ctaagcgggc ctccggggtc cctggcaggt tcagtggcgg tggatcaggc 240 acagatttca cactgaaaat cagcagagtg gaggctgacg atgtgggcac atattactgc 300 atgcaaggtc tacaaagtcc cacgacgttc ggccaaggga ccaagttgca gatcaaa 357

<210> SEQ ID NO 18
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 18 gatgttgtgc tgactcaatc tccactgtcc ctgtccgtca gtcctggaga gccggcctct 60 atctcctgca ggtccagtca gagtctcctg tggagtaagg atgacacaag atatgacttt 120 ttgggatggt atttgcagaa gcctgggcag cctccacgac tcctcatcta tttgggttct 180 cgtcgggcct ccggggtccc tgacaggttc agcgccagtg gatcaggcac agacttcaca 240 ctgagaatta acagagtgga ggctgccgat ttcggaactt attactgcat gcaagggcga 300 cacattccct tgacgttcgg ccaagggacc agggtggaaa tcaat 345

<210> SEQ ID NO 19
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19 gatgttgtgc tgactcaatc tccactctcc ctgtccgtta gccctggaga gccggcctcg 60 atctcctgca ggtccagtca gagtctcctg tggactaaag accatcaaag ttataacttt 120 ctgggatggt atttgcagaa gcctgggcag cctccacgat tcctaatttc tttgggttct 180 cgtcgggcca acggggtccc tgtcaggttc agcgccagtg gatcaggcac agatttcaca 240 ctgaaaatta gcagagtgca gactgacgat gttggaattt actactgcat gcaaggtcga 300 cacattccct tgaccttcgg ccaagggacc aaggtggaaa tcaat 345

<210> SEQ ID NO 20
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20 gaaatcgtgc tgactcagtc tccactctcc ctgggcgtct cccctggaga ggcggcctcc 60 atctcctgca ggtctaatca ggacctcttg tataagaatg accacaatca ggtttataag 120 gaatacacct ttgtgagttg gtacgtgcag aggccgggcc agtctccaca actcctgatc 180 tatttggctt ctcagcgggc cgccggggtc cctgacaggt tcagtggcgg tggatcaggc 240 acaaatttca ctctaaagat caacaaagtg gaggctgacg atgtgggcat ttactactgc 300 atgcaaggtc tgcgaactcc catgacgttc ggccgaggga ccaaggtgga catcagg 357

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21 gagatcgtcc tgactcagtc tccgctctcc ctaggcgtct cccctggaga gacggccacc 60 atctcctgca ggtctaatca ggacctcttg tataagaata accacaacca ggtttatagg 120 gagtacacct ttgtgagttg gtacctgcag aggccgggcc agtctccaca actcctgatc 180 tatttggctt ctacgcgggc cgccggggtc cctgacaggt tcagtggcgg tggatcaggc 240 acaaatttca ctctaaaaat caacaaggtg gaggctgacg acgtgggcat ttactactgc 300 atgcaaggtc tacgaactcc catgacgttc ggccgaggga cccagctgga catcagg 357

<210> SEQ ID NO 22
<211> LENGTH: 336
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22 gattttgtcc tgactcagtc tccacattct ctatccgtca ccccgggaga gccggcctcc 60 atctcctgca ggtctagtca gagcctcctt catggtgata aaaacaacta tttggcttgg 120 tatctccaga agccagggca ctctccacag ctgctgatct atatggcttc tagtcggccc 180 tcaggggtcc ctgacaggtt cagtggcagt ggctcgggca cacattttac actgaaaatc 240 agtagagtgg agactgaaga tgttgggatg tactactgca tgcaaggtcg agaaagtccc 300 tggacgtttg gccaagggac caaggtggaa atcaaa 336

<210> SEQ ID NO 23
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23 gatgttgtgc tgactcaatc tccactctcc ctgtccgtta gccctggaga gccggcctcg 60 atctcctgta ggtccagtca gagtctcctg tggactaaag accatcaaag ttataacttt 120 ctgggatggt atttgcagaa gcctgggcag cctccacgat tcctaatctc tttgggttct 180 catcgggcct ccggagtccc tgacaggttc agcgccagtg gctcaggcac agatttcaca 240 ctgaaaatta gcagagtgca gactgacgat gttggaactt attactgcat gcaaggtcga 300 cacattccct tgacgttcgg ccaagggacc aaggtggaaa tcaag 345

<210> SEQ ID NO 24
<211> LENGTH: 345
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24 gatgttgtga tgactcagtc tccactctcc ctgtccgtca cccctggaga gccggcctct 60 atctcctgca ggtccagtca gagcctcctg tggaataagg gtgatcaaag atataatttt 120 ctgggatggt atttgcagaa gcctgggcag cctccacgac tcctaatgta tttggcttcc 180 agtcgggcct ccggggtccc tgacaggttc agcggcagag gatcaggcac agacttcaca 240 ctgaaaatta acagagtgga ggctgacgat gtcggaactt attactgctt ccaaggtcga 300 cacactccct tgacgttcgg ccaagggacc aaggtggaaa tcaat 345

<210> SEQ ID NO 25
<211> LENGTH: 333
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 25 cagactgttc tgactcagtc gccactctcc ctggccgtca cccctggcga gccggcctcc 60 atctcctgta agtgttctca gaacttaaac gttcagggat acgattttgt gagttggtat 120 gtacagaaac caggccaatc tccacgtctc ctgatgtact cgtcttccct gcgggcctcc 180 ggggtccctg acagatttag tggcagtgga tccgccacat cttttacact taaaatcaag 240 agagtcgagc cggaagatct ggggacttat tactgcatgg acactctacg ccctccctac 300 gccttcggcc aggggaccaa gctggagatc aga 333

<210> SEQ ID NO 26
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 26 gagattgtgc tgagtcagtc tccactctcc ctggccgtca cccctggaga gccggcctcc 60 atctcctgca ggtctagcca gagcctcctc tataagaatg aacacaatgg tgtgtacaaa 120 gaatatacct ttttgagctg gtacttgcag aagccaggcc agtccccaca actcctgatg 180 tatttgggtt ctacgcgggc gtccggggtc cctggcaggt tcagtggcgg tggatcaggc 240 acagatttca cactgaaaat cagcagagtg gaggctgacg atgtgggcac ttatttctgc 300 atgcaaggtc ttcaggttcc catgacgttc ggccaaggga ccaaggtgga gatcaaa 357

<210> SEQ ID NO 27
<211> LENGTH: 17
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 27

Gly Ser Gly Leu Asn Asp Ile Phe Glu Ala Gln Lys Ile Glu Trp His
1 5 10 15

Glu

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28 atggactgga tttggaggat 20

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29 atggactgga tttggaggat cctcttcttg g 31

<210> SEQ ID NO 30
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 30 atgaggctcc ctgctgccat cctggggctg ctaatgc 37

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 31 gctcctgggg ctgctaatgc tctgggtctc tgg 33

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 32 atggactgga tttggaggat 20

<210> SEQ ID NO 33
<211> LENGTH: 23
<212> TYPE: DNA

<213> ORGANISM: Artificial Sequence
<220> FEATURE:
<223> OTHER INFORMATION: Description of Artificial Sequence: Synthetic
primer

<400> SEQUENCE: 33 ggaaggtgtg cacgccgctg gtc 23

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 34 atggactgga tttggaggat cctcttcttg g 31

<210> SEQ ID NO 35
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 35 gttcggggaa gtagtccttg ac 22

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
primer

<400> SEQUENCE: 36 atgaggctcc ctgctcagct cctggggctg ctaatgc 37

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 37 gtttctcgta gtctgctttg ctca 24

<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: Synthetic
primer

<400> SEQUENCE: 38 gctcctgggg ctgctaatgc tctgggtctc tgg 33

<210> SEQ ID NO 39
<211> LENGTH: 22
<212> TYPE: DNA
<213> ORGANISM: Artificial Sequence <220> FEATURE:
<223> OTHER INFORMATION: Description of Artificial Sequence: Synthetic
primer

<400> SEQUENCE: 39 gtgctgtcct tgctgtcctg ct 22

<210> SEQ ID NO 40
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 40

Cys Ala Lys Gly Ser Lys His Arg Leu Arg Asp Tyr Ala Leu Tyr Asp
1 5 10 15

Asp Asp Gly Ala Leu Asn Trp Ala Val Asp Val Asp Tyr Leu Ser Asn
20 25 30

Leu Glu Phe Trp
35

<210> SEQ ID NO 41
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 41

Cys Ala Arg Gly Ser Lys His Arg Leu Arg Asp Tyr Val Met Tyr Asp
1 5 10 15

Asp Tyr Gly Ala Leu Gln Trp Ala Val Tyr Val Asp Tyr Leu Ser Asn
20 25 30

Leu Asp Val Trp
35

<210> SEQ ID NO 42
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

Cys Ala Lys Gly Ser Lys His Arg Leu Arg Asp Tyr Ala Leu Tyr Asp
1 5 10 15

Asp Ile Gly Ala Leu Gln Trp Ala Val Asp Val Asp Tyr Leu Ser Thr
20 25 30

Leu Glu Phe Trp
35

<210> SEQ ID NO 43
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Cys Val Lys Gly Ser Lys Phe Arg Leu Arg Glu Trp Ala Asp Tyr Asn
1               5                   10                  15

Glu Trp Gly Leu Val Ser Ala Gln His Gly Asp Tyr Val Thr Gln Leu
            20                  25                  30

Gly Ile Trp
        35


<210> SEQ ID NO 44
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Cys Val Arg Gly Ala Lys Phe Arg Leu Arg His Asp Ala Thr Tyr Asp
1               5                   10                  15

Tyr Trp Asn Asp Leu Leu Trp Ala Asp Asp Arg Asp Tyr Val Thr Gln
            20                  25                  30

Leu Asp Leu Trp
        35


<210> SEQ ID NO 45
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Cys Val Arg Gly Ala Lys Phe Arg Leu Arg His Asp Ala Thr Tyr Asp
1               5                   10                  15

Tyr Tyr Asn Asp Leu Leu Trp Ala Asp Asp Arg Asp Tyr Val Thr Gln
            20                  25                  30

Leu Asp Leu Trp
        35


<210> SEQ ID NO 46
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Cys Val Lys Gly Gln Lys Phe Arg Leu Thr Glu Trp Ala Asp Tyr Asn
1               5                   10                  15

Glu Phe Gly Leu Val Ala Ala Gln Lys Gly Asp Tyr Val Thr Gln Leu
            20                  25                  30

Asp Val Trp
        35


<210> SEQ ID NO 47
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47
```

```
Cys Val Lys Gly Gln Lys Phe Arg Leu Thr Glu Trp Ala Asp Tyr Asn
1               5                   10                  15

Glu Phe Gly Leu Val Ala Ala Glu Lys Gly Asp Tyr Val Thr Gln Leu
            20                  25                  30

Asp Val Trp
        35


<210> SEQ ID NO 48
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Cys Ala Arg Gly Ser Lys His Lys Leu Arg Asp Tyr Val Met Tyr Asp
1               5                   10                  15

Asp Tyr Gly Ala Leu Gln Trp Ala Val Tyr Val Asp Tyr Leu Ser Asn
            20                  25                  30

Leu Asp Val Trp
        35


<210> SEQ ID NO 49
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Cys Val Arg Gly Ala Lys Phe Arg Leu Arg His Asp Ala Thr Tyr Asp
1               5                   10                  15

Tyr Trp Asn Asp Leu Leu Trp Ala Asp Asp Arg Asp Tyr Val Thr Gln
            20                  25                  30

Leu Asp Leu Trp
        35


<210> SEQ ID NO 50
<211> LENGTH: 36
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Cys Val Arg Gly Ser Lys Phe Arg Leu Arg Asn Asp Ala Ile Tyr Asp
1               5                   10                  15

Tyr Trp Asn Asp Leu Leu Trp Ala Asp Asp Gly Asp Tyr Val Thr Lys
            20                  25                  30

Leu Asp Leu Trp
        35


<210> SEQ ID NO 51
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 51

Cys Ala Arg Arg Thr Glu Lys Gln Leu Arg Ala Glu Tyr Val Leu Asp
1 5 10 15

Gln Glu Asp Gly Phe Tyr Arg Glu Glu Ala Ile Tyr Ile Thr Val Leu
20 25 30

Asp Val Trp
35

<210> SEQ ID NO 52
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 52

Cys Val Lys Gly Leu Lys Phe Arg Leu Arg Glu Trp Ser Asp Tyr Asn
1 5 10 15

Glu Phe Gly Leu Val Ala Ala Gln His Gly Asp Tyr Val Thr Gln Met
20 25 30

Glu Val Trp
35

<210> SEQ ID NO 53
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 53

Cys Thr Arg Gly Ser Lys His Arg Leu Arg Asp Tyr Val Leu Tyr Asp
1 5 10 15

Asp Tyr Gly Leu Ile Asn Tyr Gln Glu Trp Asn Asp Tyr Leu Glu Phe
20 25 30

Leu Asp Val Trp
35

<210> SEQ ID NO 54
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 54

Cys Thr Arg Gly Ser Lys His Arg Leu Arg Asp Tyr Val Leu Tyr Asp
1 5 10 15

Asp Tyr Gly Leu Ile Asn Tyr Gln Glu Trp Asn Asp Tyr Leu Glu Phe
20 25 30

Leu Asp Val Trp
35

<210> SEQ ID NO 55
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 55

Cys Thr Arg Gly Ser Lys His Arg Leu Arg Asp Tyr Val Leu Tyr Asp
1 5 10 15

Asp Tyr Gly Leu Ile Asn Tyr Gln Glu Trp Asn Asp Tyr Leu Glu Phe
20 25 30

Leu Asp Val Trp
35

<210> SEQ ID NO 56
<211> LENGTH: 36
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 56

Cys Thr Gly Gly Ser Lys His Arg Leu Arg Asp Tyr Val Leu Tyr Asp
1 5 10 15

Asp Tyr Gly Leu Ile Asn Gln Gln Glu Trp Asn Asp Tyr Leu Glu Phe
20 25 30

Leu Asp Val Trp
35

<210> SEQ ID NO 57
<211> LENGTH: 35
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

Cys Leu Thr Gly Ser Lys His Arg Leu Arg Asp Tyr Phe Leu Tyr Asn
1 5 10 15

Glu Tyr Gly Pro Asn Tyr Glu Glu Trp Gly Asp Tyr Leu Ala Thr Leu
20 25 30

Asp Val Trp
35

<210> SEQ ID NO 58
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Cys Met Gln Gly Arg Glu Ser Pro Trp Thr Phe
1 5 10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 59

Cys Met Gln Gly Arg Glu Ser Pro Trp Thr Phe
1 5 10

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 60

Cys Met Gln Gly Arg Glu Ser Pro Trp Thr Phe
1 5 10

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Cys Met Gln Gly Leu Gln Ser Pro Thr Thr Phe
1 5 10

<210> SEQ ID NO 62
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 62

Cys Met Gln Gly Arg His Ile Pro Leu Thr Phe
1 5 10

<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Cys Met Gln Gly Arg His Ile Pro Leu Thr Phe
1 5 10

<210> SEQ ID NO 64
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 64

Cys Met Gln Gly Leu Arg Thr Pro Met Thr Phe
1 5 10

<210> SEQ ID NO 65
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 65

Cys Met Gln Gly Leu Arg Thr Pro Met Thr Phe
1 5 10

<210> SEQ ID NO 66
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 66

Cys Met Gln Gly Arg Glu Ser Pro Trp Thr Phe
1 5 10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 67

Cys Met Gln Gly Arg His Ile Pro Leu Thr Phe
1 5 10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 68

Cys Phe Gln Gly Arg His Thr Pro Leu Thr Phe
1 5 10

<210> SEQ ID NO 69
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 69

Cys Met Asp Thr Leu Arg Pro Pro Tyr Ala Phe
1 5 10

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 70

Cys Met Gln Gly Leu Gln Val Pro Met Thr Phe
1 5 10

<210> SEQ ID NO 71
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Cys Met Gln Gly Leu Asn Arg Pro Trp Thr Phe
1               5                   10


<210> SEQ ID NO 72
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Cys Met Gln Gly Leu Asn Arg Pro Trp Thr Phe
1               5                   10


<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Cys Met Gln Gly Leu Asn Arg Pro Trp Thr Phe
1               5                   10


<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Cys Met Gln Gly Leu Asn Arg Pro Trp Thr Phe
1               5                   10


<210> SEQ ID NO 75
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Cys Met Gln Gly Leu His Ser Pro Trp Thr Phe
1               5                   10
```

What is claimed is:

1. A non-naturally occurring anti-HIV-1 monoclonal antibody or antigen binding portion thereof, comprising (a) a heavy chain sequence comprising an amino acid sequence encoded by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13 and (b) a light chain sequence comprising an amino acid sequence encoded by SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.

2. The non-naturally occurring anti-HIV-1 monoclonal antibody *or antigen binding portion* of claim 1, wherein the heavy chain sequence is encoded by SEQ ID NO: 1 and the light chain sequence is encoded by SEQ ID NO: 14.

3. A composition comprising the antibody *or antigen binding portion* of claim 1.

4. A pharmaceutical composition comprising the antibody *or antigen binding portion* of claim 1 and a pharmaceutically acceptable carrier.

5. The antibody or antigen binding portion of claim 1, wherein the heavy chain sequence comprises a third complementarity determining region (CDRE3) of 33 to 34 amino acid residues.

6. The antibody or antigen binding portion of claim 5, wherein a triad of aspartic acid residues at the tip of CDRH3 provides an anionic potential to the CDRH3.

*7. A non-naturally occurring anti-HIV-1 monoclonal antibody or antigen binding portion thereof, comprising*

*(a) the heavy chain CDRs of a heavy chain sequence encoded by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, or SEQ ID NO: 13, and*

*(b) the light chain CDRs of a light chain sequence encoded by SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, or SEQ ID NO: 26.*

*8. The antibody or antigen binding portion of claim 7 comprising the heavy chain CDR3 of any one of SEQ ID NO: 40-52 and the light chain CDR3 of any one of SEQ ID NO: 58-70.*

*9. The antibody or antigen binding portion of claim 7, wherein the heavy chain CDR3 comprises the amino acid sequence of SEQ ID NO: 40, and the light chain CDR3 comprises the amino acid sequence of SEQ ID NO: 58.*

*10. The antibody or antigen binding portion of claim 8, wherein a triad of aspartic acid residues at the tip of heavy chain CDR3 provides an anionic potential to the heavy chain CDR3.*

*11. A non-naturally occurring anti-HIV-1 monoclonal antibody or antigen binding portion thereof comprising*

*(a) a heavy chain variable region comprising an amino acid sequence with at least 90% identity to the amino acid sequence encoded by SEQ ID NO:1, and*

*(b) a light chain variable region comprising an amino acid sequence with at least 90% identity to the amino acid sequence encoded by SEQ ID NO: 14.*

*12. The antibody or antigen binding portion of claim 11, wherein the heavy chain CDR3 comprises the amino acid sequence of SEQ ID NO: 40, and the light chain CDR3 comprises the amino acid sequence of SEQ ID NO: 58.*

*13. The antibody or antigen binding portion of claim 11, wherein the heavy chain variable region comprises an amino acid sequence with at least 95% identity to the amino acid sequence encoded by SEQ ID NO: 1, and the light chain variable region comprises an amino acid sequence with at least 95% identity to the amino acid sequence encoded by SEQ ID NO: 14.*

*14. A non-naturally occurring anti-HIV-1 monoclonal antibody or antigen binding portion thereof comprising*

*(a) a heavy chain variable region comprising an amino acid sequence with at least 90% identity to the amino acid sequence encoded by SEQ ID NO:1, and*

*(b) a light chain variable region comprising an amino acid sequence with at least 90% identity to the amino acid sequence encoded by SEQ ID NO: 14,*

*wherein the antibody interacts with HIV gp120 V1/V2 domain of BG505.*

*15. The antibody or antigen binding portion of claim 14, wherein the heavy chain variable region comprises an amino acid sequence with at least 95% identity to the amino acid sequence encoded by SEQ ID NO: 1, and the light chain variable region comprises an amino acid sequence with at least 95% identity to the amino acid sequence encoded by SEQ ID NO: 14.*

*16. The antibody or antigen binding portion of claim 14, wherein the heavy chain CDR3 comprises the amino acid sequence of SEQ ID NO: 40, and the light chain CDR3 comprises the amino acid sequence of SEQ ID NO: 58.*

*17. A non-naturally occurring anti-HIV-1 monoclonal antibody or antigen binding portion thereof comprising*

*(a) a heavy chain variable region comprising an amino acid sequence with at least 90% identity to the amino acid sequence encoded by SEQ ID NO:1, and*

*(b) a light chain variable region comprising an amino acid sequence with at least 90% identity to the amino acid sequence encoded by SEQ ID NO: 14,*

*wherein the antibody has a minimal cross-clade neutralization coverage of 80% on the 106-virus panel shown in FIG. 9.*

*18. The antibody or antigen binding portion of claim 17, wherein the heavy chain variable region comprises an amino acid sequence with at least 95% identity to the amino acid sequence encoded by SEQ ID NO: 1, and the light chain variable region comprises an amino acid sequence with at least 95% identity to the amino acid sequence encoded by SEQ ID NO: 14.*

*19. The antibody or antigen binding portion of claim 17, wherein the heavy chain CDR3 comprises the amino acid sequence of SEQ ID NO: 40, and the light chain CDR3 comprises the amino acid sequence of SEQ ID NO: 58.*

*20. A non-naturally occurring anti-HIV-1 monoclonal antibody or antigen binding portion thereof comprising*

*(a) a heavy chain variable region comprising an amino acid sequence with at least 90% identity to the amino acid sequence encoded by SEQ ID NO: 1, wherein the heavy chain CDR3 comprises the amino acid sequence of SEQ ID NO: 40, and*

*(b) a light chain variable region comprising an amino acid sequence with at least 90% identity to the amino acid sequence encoded by SEQ ID NO: 14, wherein the light chain CDR3 comprises the amino acid sequence of SEQ ID NO: 58,*

*wherein the antibody interacts with HIV gp120 V1/V2 domain of BG505, and has a minimal cross-clade neutralization coverage of 80% on the 106-virus panel shown in FIG. 9, and*

*wherein a triad of aspartic acid residues at the tip of the heavy chain CDR3 provides an anionic potential to the heavy chain CDR3.*

*21. A pharmaceutical composition comprising the antibody or antigen binding portion of claim 7 and a pharmaceutically acceptable carrier.*

*22. A pharmaceutical composition comprising the antibody or antigen binding portion of claim 11 and a pharmaceutically acceptable carrier.*

*23. An isolated polypeptide comprising the amino acid sequence of any one of SEQ ID NO: 40-52.*

* * * * *